(12) United States Patent
Popowski

(10) Patent No.: US 12,370,382 B2
(45) Date of Patent: Jul. 29, 2025

(54) WEARABLE INSERTER FOR REPRODUCABLE ALIGNMENT OF BODILY TISSUE FOR PROGRAMME OF EXTERNAL RADIOTHERAPY TREATMENT

(71) Applicant: PELVIRAY IP LTD, Limassol (CY)

(72) Inventor: Georg Popowski, Geneva (CH)

(73) Assignee: PELVIRAY IP LTD, Limassol (CY)

( * ) Notice: Subject to any disclaimer, the term of this patent is extended or adjusted under 35 U.S.C. 154(b) by 335 days.

(21) Appl. No.: 18/033,437

(22) PCT Filed: Nov. 24, 2021

(86) PCT No.: PCT/EP2021/082759
§ 371 (c)(1),
(2) Date: Apr. 24, 2023

(87) PCT Pub. No.: WO2022/112289
PCT Pub. Date: Jun. 2, 2022

(65) Prior Publication Data
US 2023/0414967 A1    Dec. 28, 2023

(30) Foreign Application Priority Data
Nov. 24, 2020   (EP) .................................... 20209522

(51) Int. Cl.
*A61N 5/10*        (2006.01)
(52) U.S. Cl.
CPC .... *A61N 5/1049* (2013.01); *A61N 2005/1092* (2013.01)
(58) Field of Classification Search
CPC ...................... A61N 5/1049; A61N 2005/1092
See application file for complete search history.

(56) References Cited

U.S. PATENT DOCUMENTS 6,024,738 A * 2/2000 Daikuzono .......... A61B 18/245
606/7
6,045,495 A * 4/2000 Weinberger .......... A61N 5/1002
600/3

(Continued)

FOREIGN PATENT DOCUMENTS

WO    2022/112295 A1    6/2022
WO    2022/112297 A1    6/2022

OTHER PUBLICATIONS

International Search Report and Written Opinion mailed on Feb. 24, 2022, issued in PCT International Patent Application No. PCT/EP2021/082759.

*Primary Examiner* — Nicole M Ippolito
(74) *Attorney, Agent, or Firm* — Amster, Rothstein & Ebenstein LLP

(57) ABSTRACT

Positioning tool (200) for assisting treatment of a subject in an external radiotherapy programme comprising one or more external radiotherapy treatment sessions comprising: an inserter (204) having a proximal (40) and distal (20) end which inserter comprises: an elongated member (210) configured for insertion through an entrance to a canal (602) in connection with bodily tissue (610) of the subject, and provided with an elongated member lumen (214) configured for receiving an effector shaft (310) of a steering guide (300); and a guiding strand (218) for guiding the effector shaft (310) into the lumen (214) from outside the entrance to the canal, wherein the guiding strand (218) is disposed at least partially within the lumen (214) and is restrained at or towards a distal end (20) of the guiding strand (218) to limit or prevent sliding of the guiding strand (218) in a proximal direction relative to the lumen (214), wherein the positioning tool (200) is configured to move and/or fix the canal (602) and the bodily tissue (610) of the subject relative to an (Continued)

ionising radiotherapy beam for the external radiotherapy treatment session.

18 Claims, 19 Drawing Sheets

(56) References Cited

U.S. PATENT DOCUMENTS

| | | | |
|---|---|---|---|
| 2005/0203440 A1* | 9/2005 | Gellman | A61B 10/0275 600/567 |
| 2008/0097471 A1 | 4/2008 | Adams et al. | |
| 2008/0293994 A1 | 11/2008 | Francescatti et al. | |
| 2009/0227827 A1 | 9/2009 | Hausen et al. | |
| 2013/0317276 A1 | 11/2013 | D'Andrea | |
| 2015/0038767 A1 | 2/2015 | Isham | |
| 2017/0312546 A1 | 11/2017 | Ravi et al. | |
| 2020/0170723 A1 | 6/2020 | Crawford et al. | |
| 2023/0398375 A1 | 12/2023 | Popowski | |
| 2024/0001143 A1 | 1/2024 | Popowski | |

\* cited by examiner

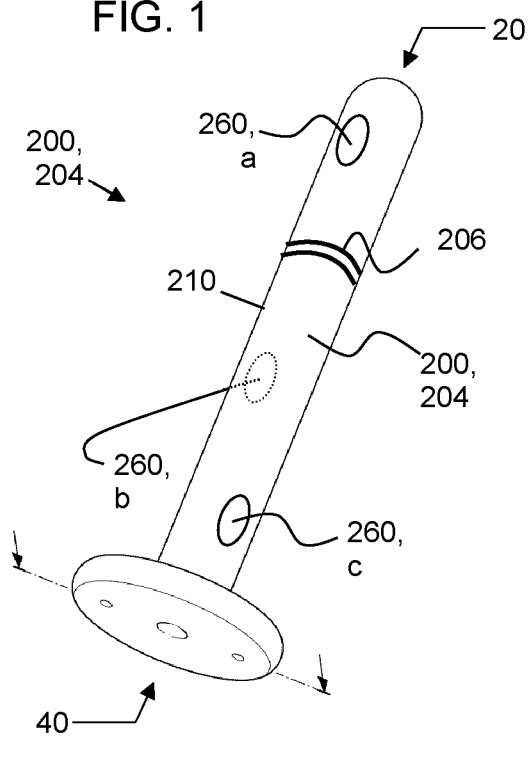
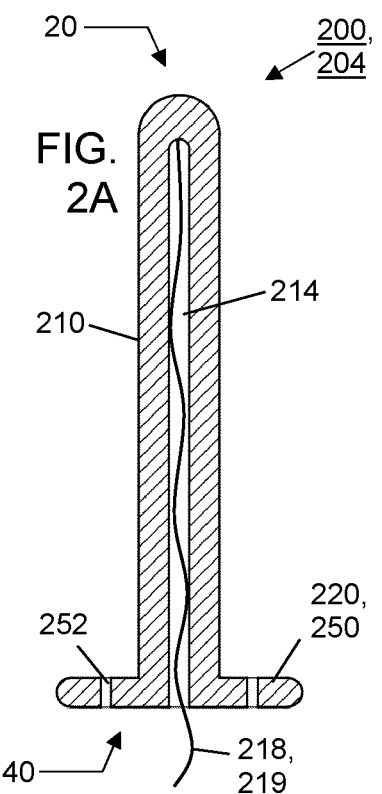
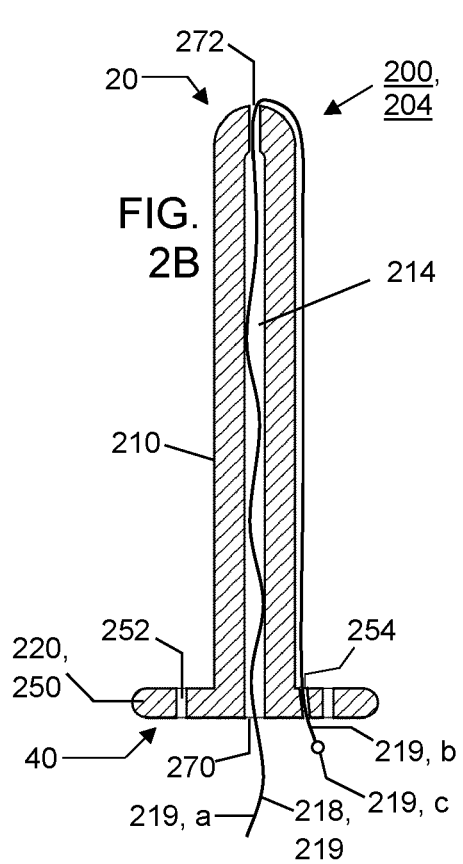
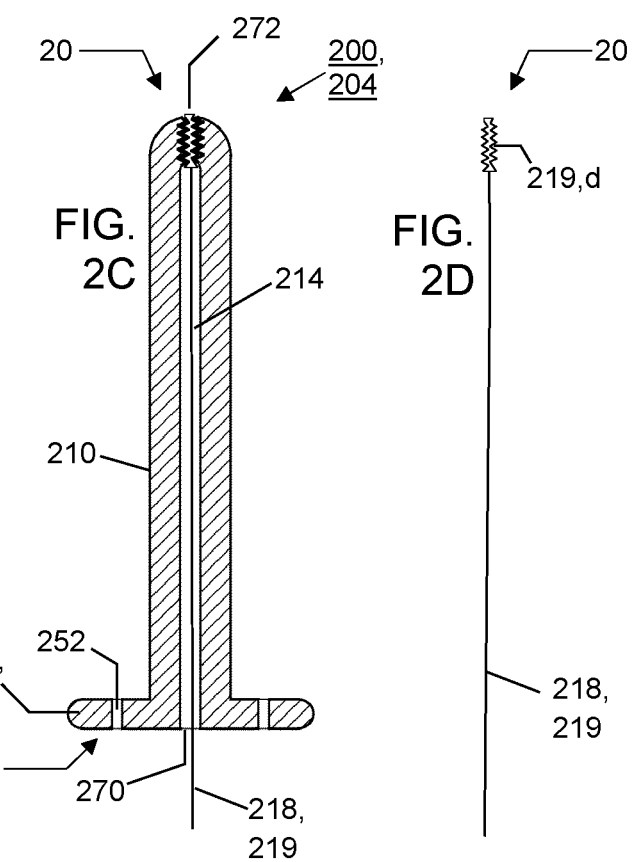
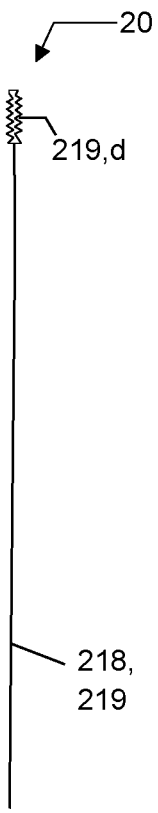

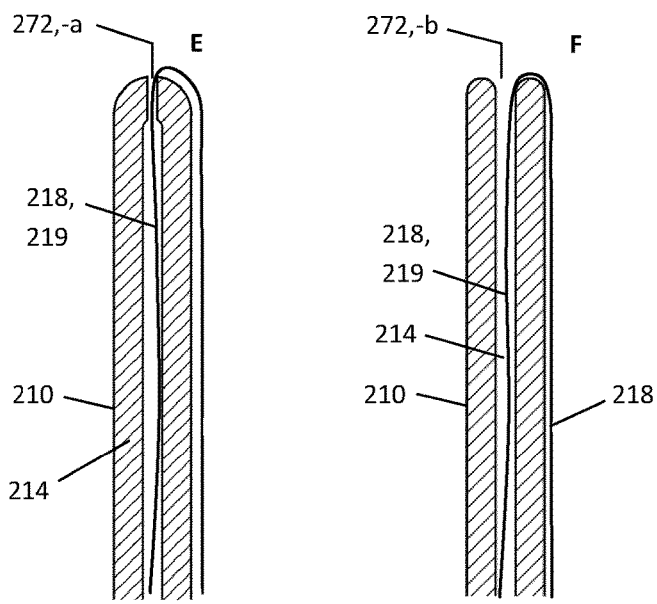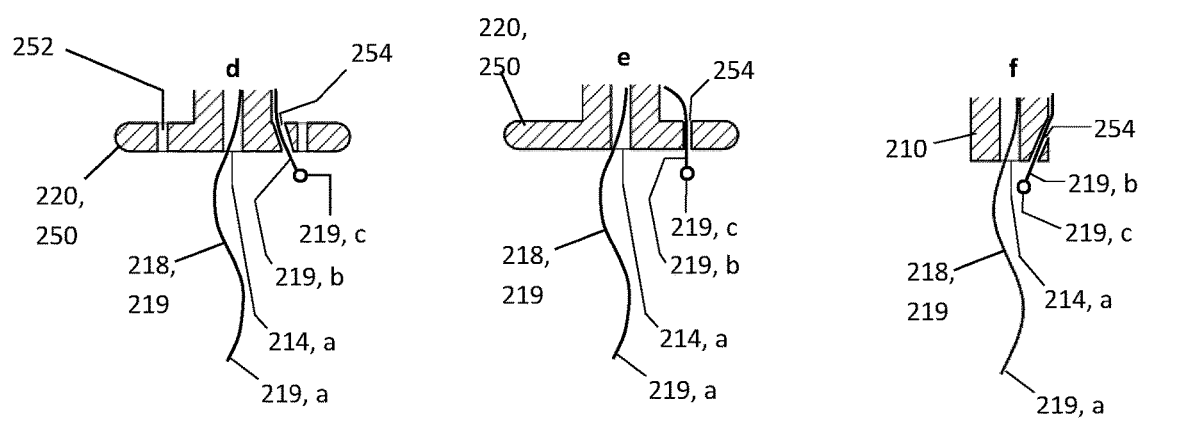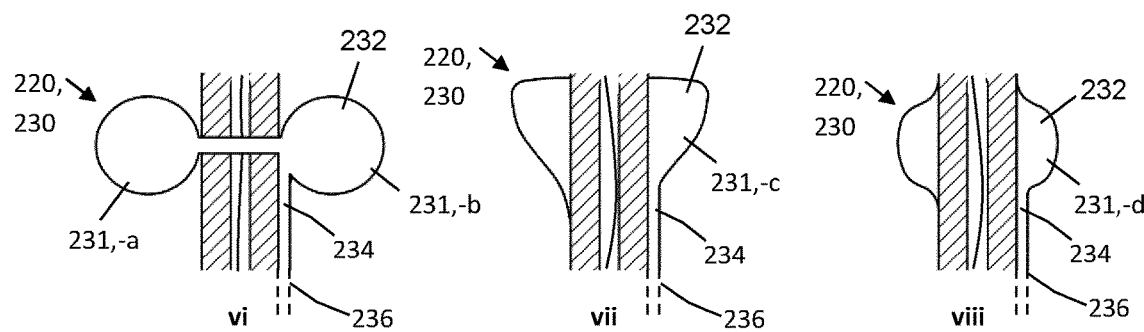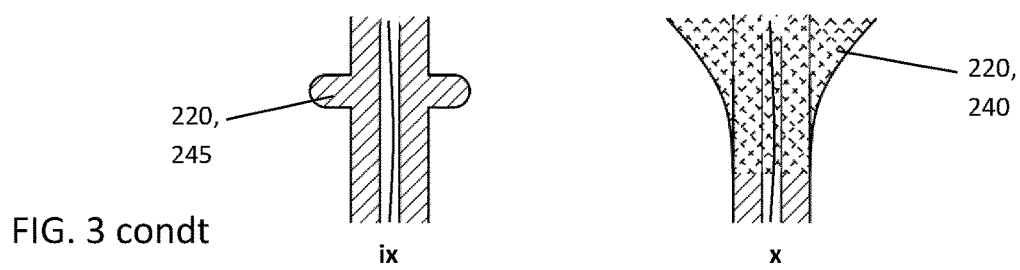
FIG. 3 condt

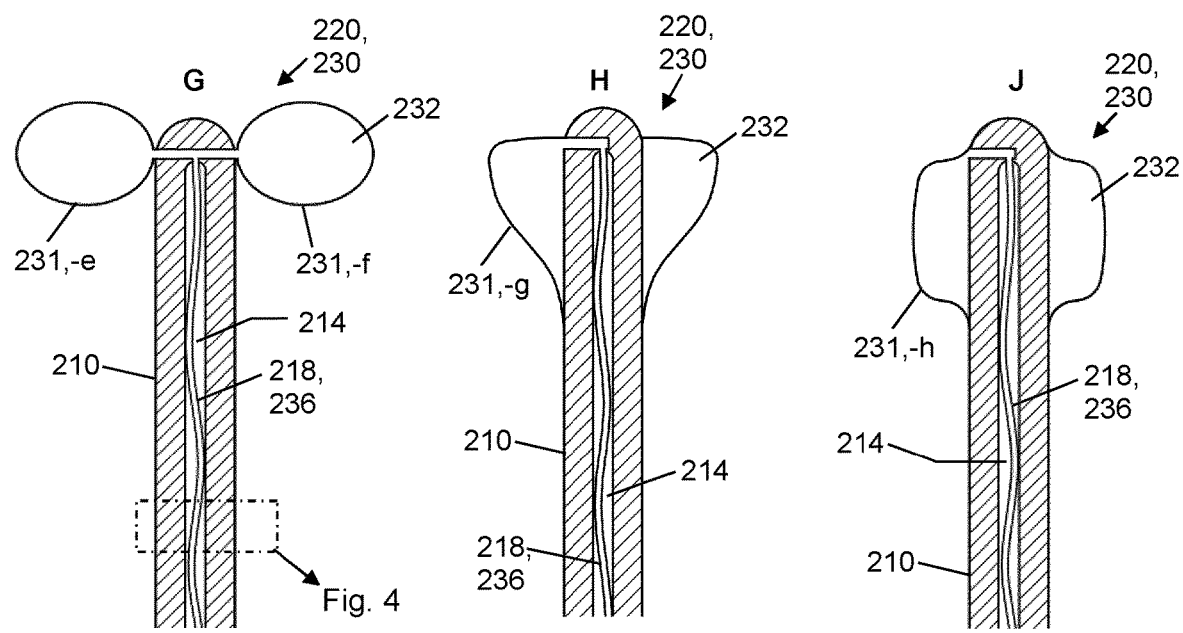
FIG. 3 condt
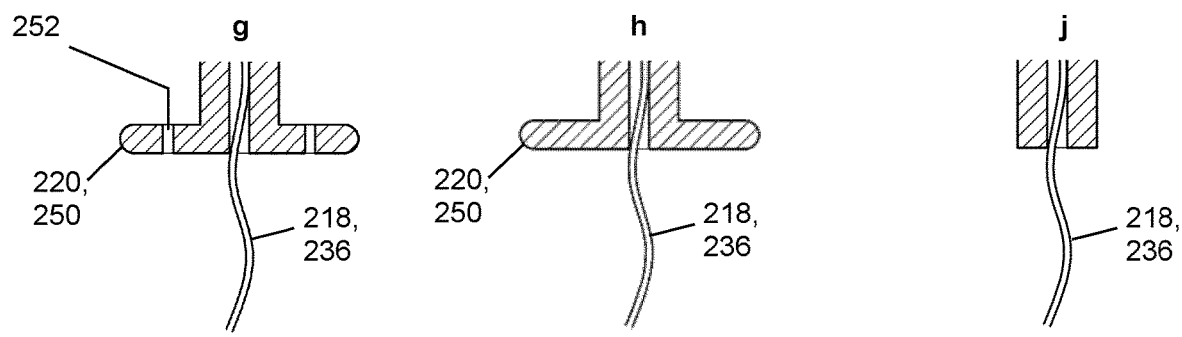
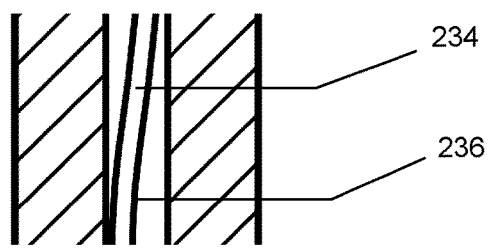
FIG. 4

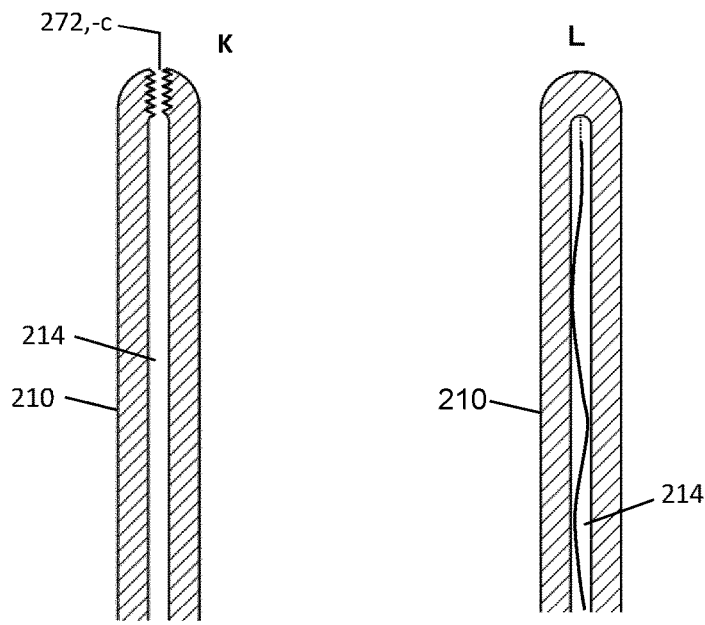
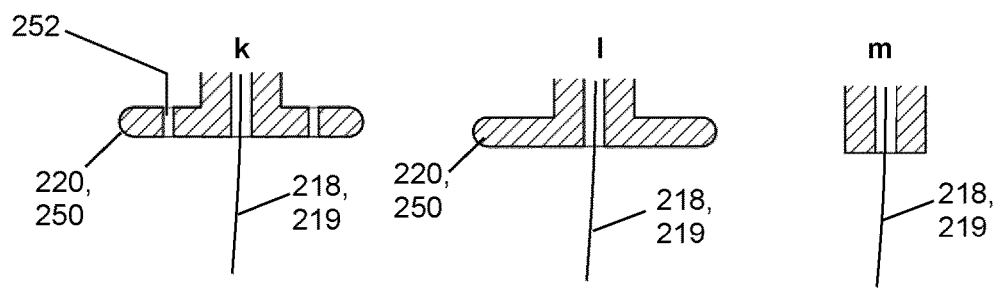
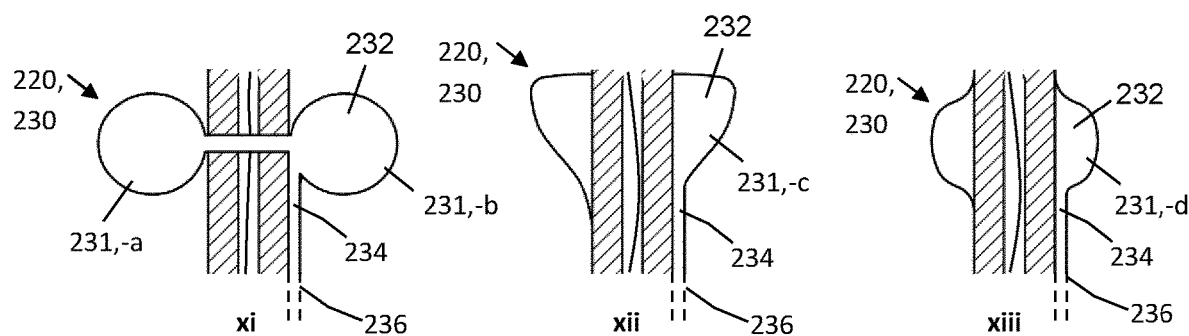
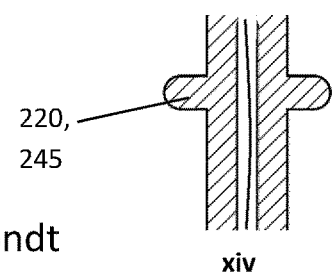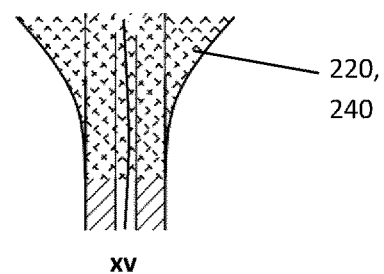
FIG. 3 condt

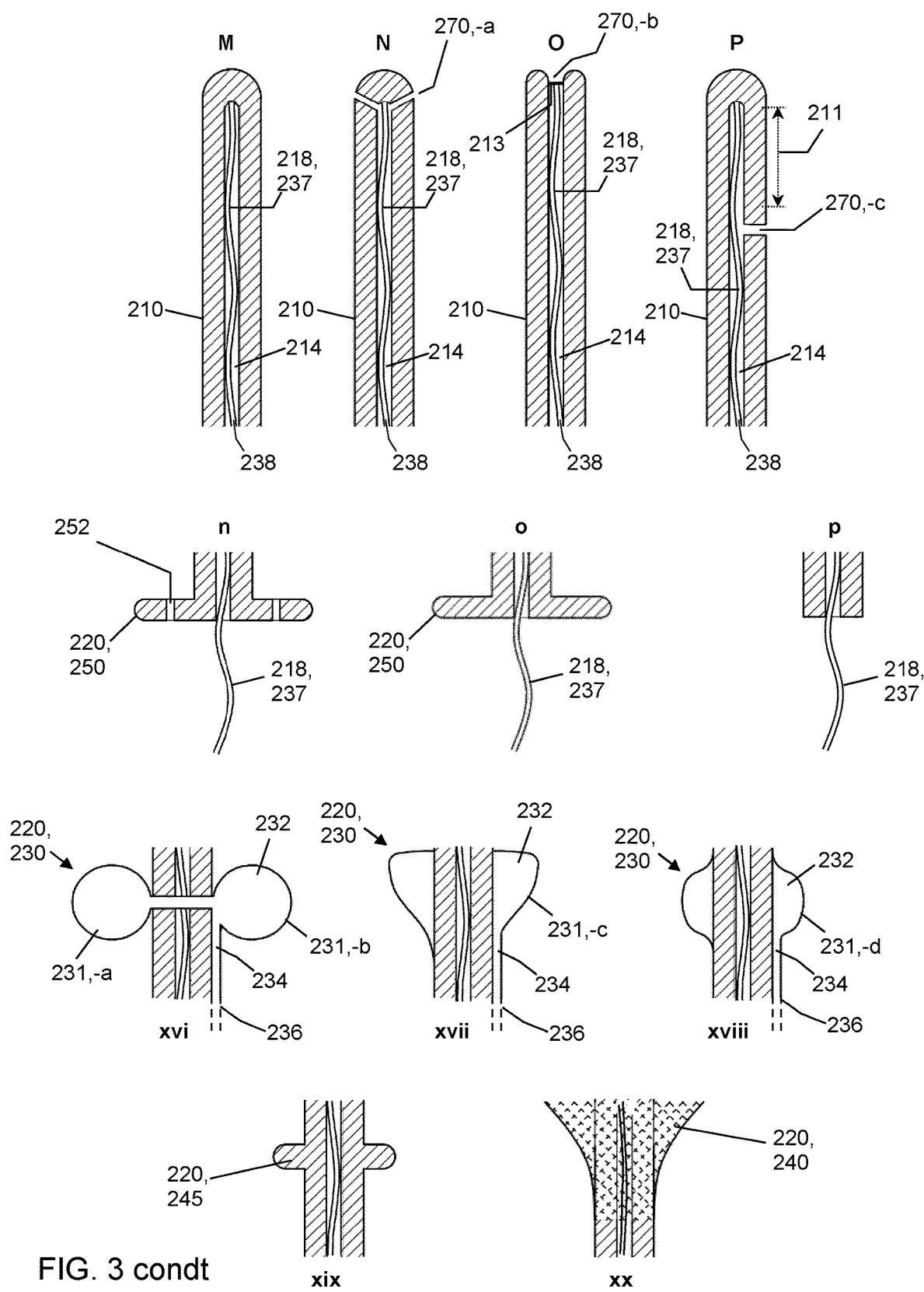
FIG. 3 condt

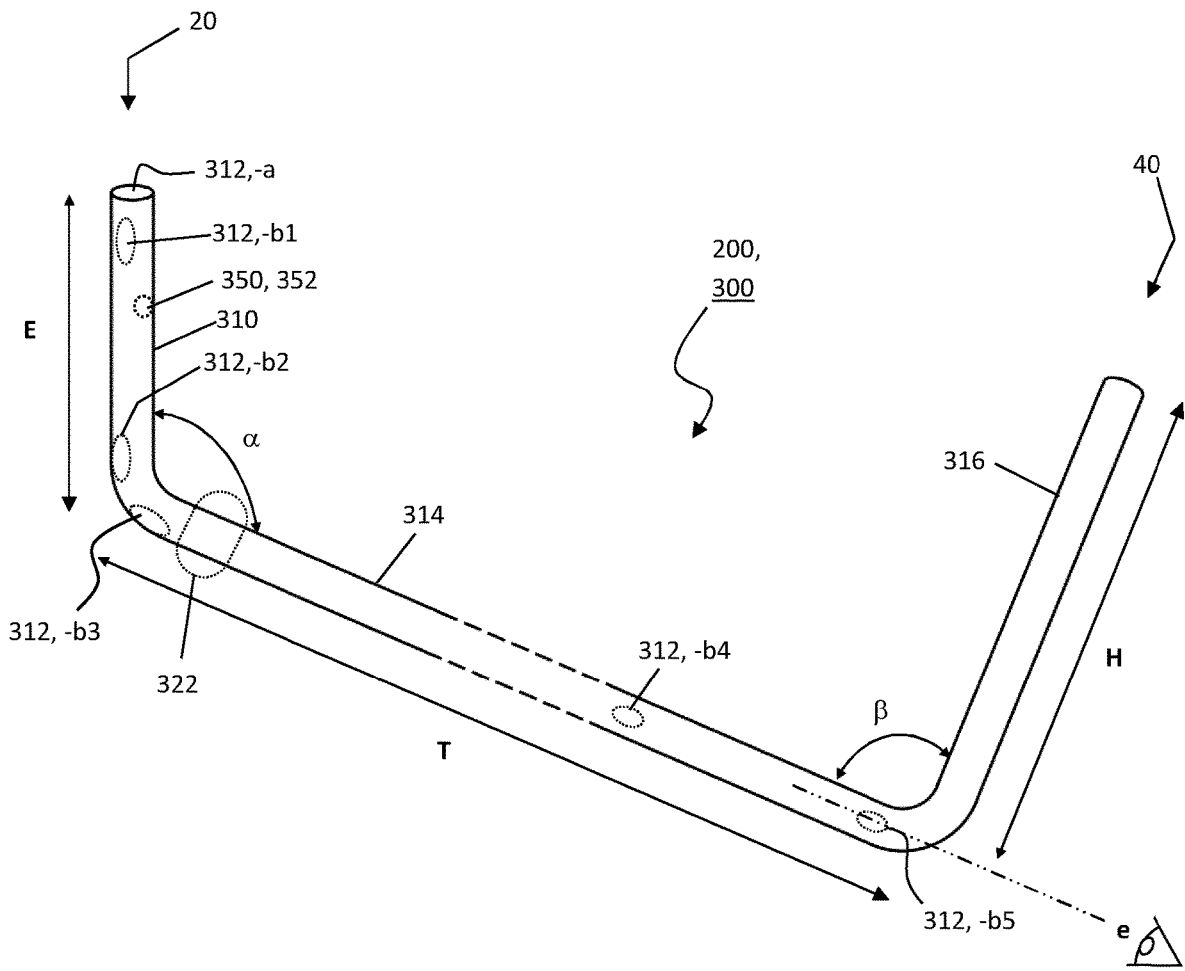
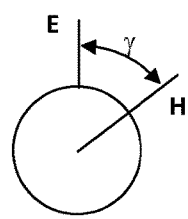
FIG. 6
FIG. 6A

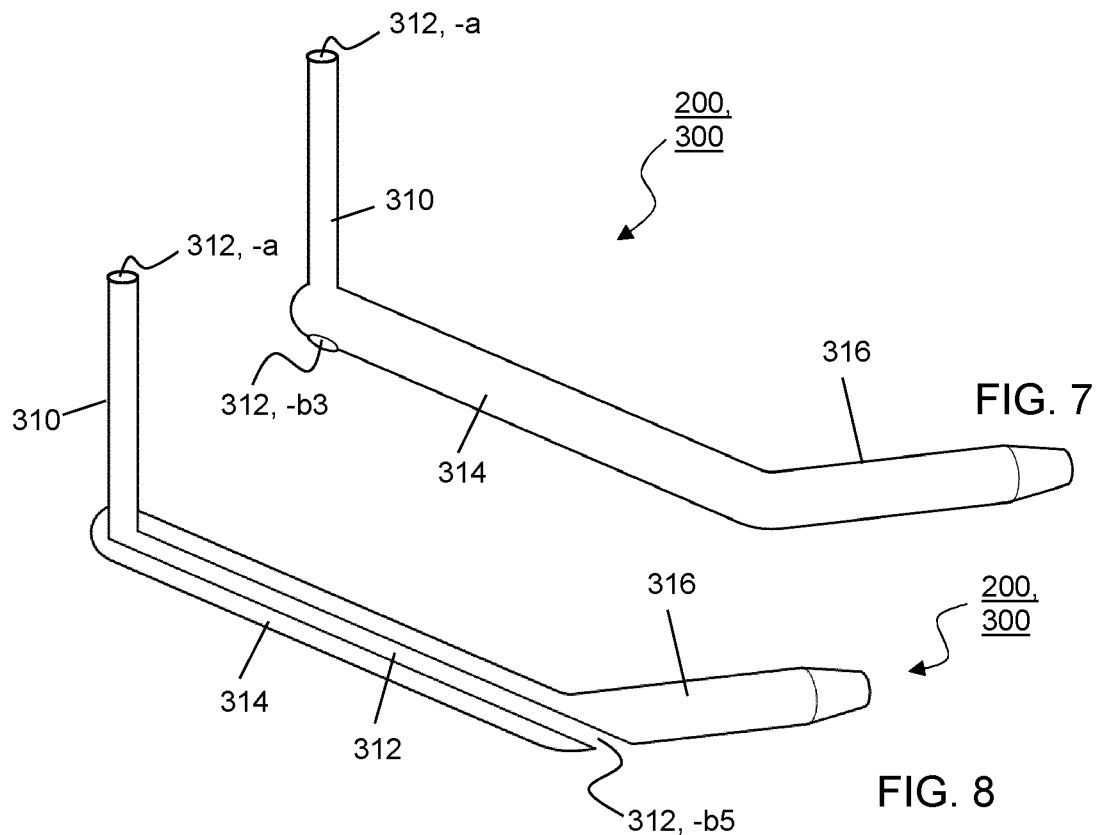
FIG. 7
FIG. 8
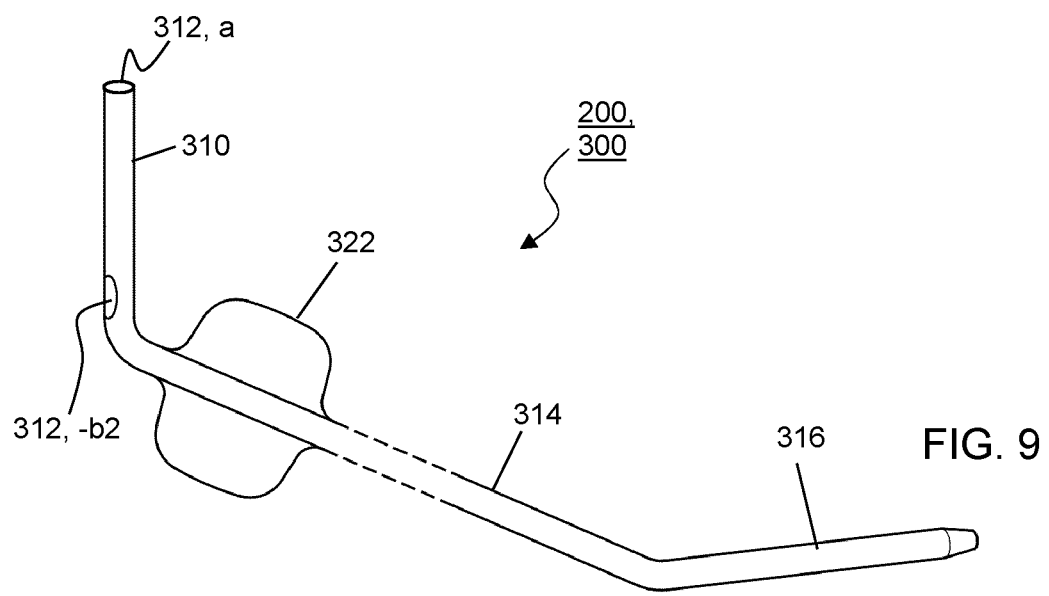
FIG. 9

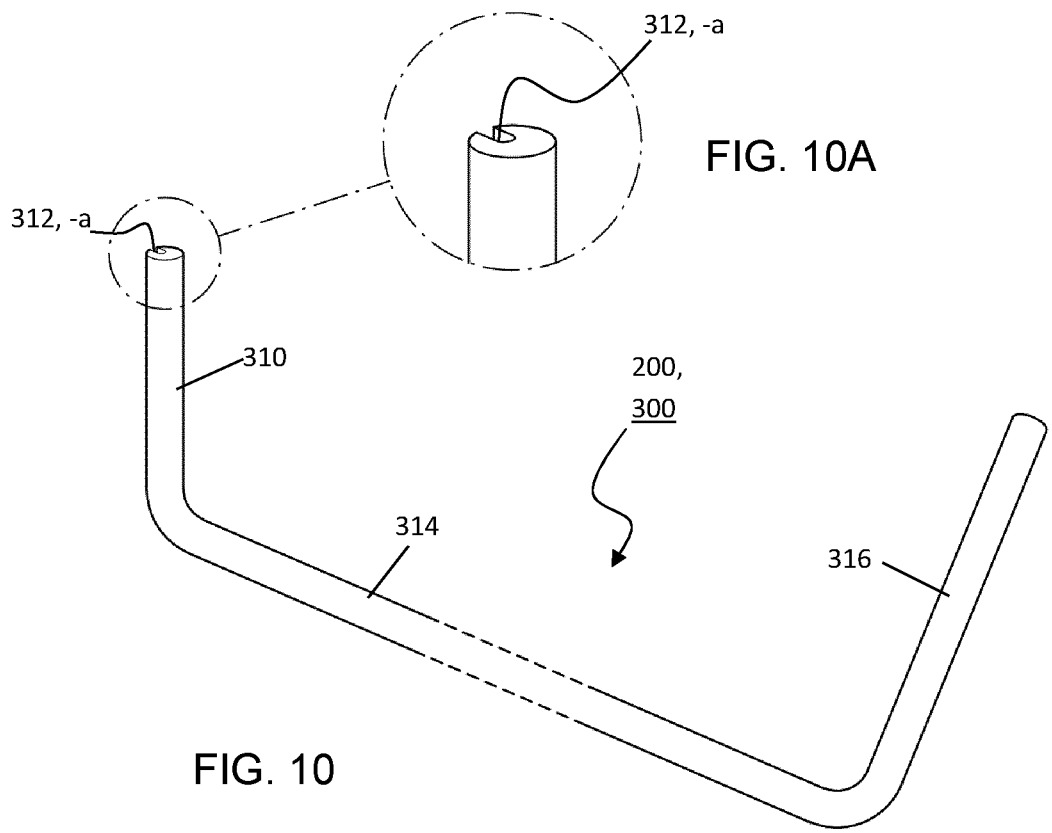
FIG. 10A
FIG. 10
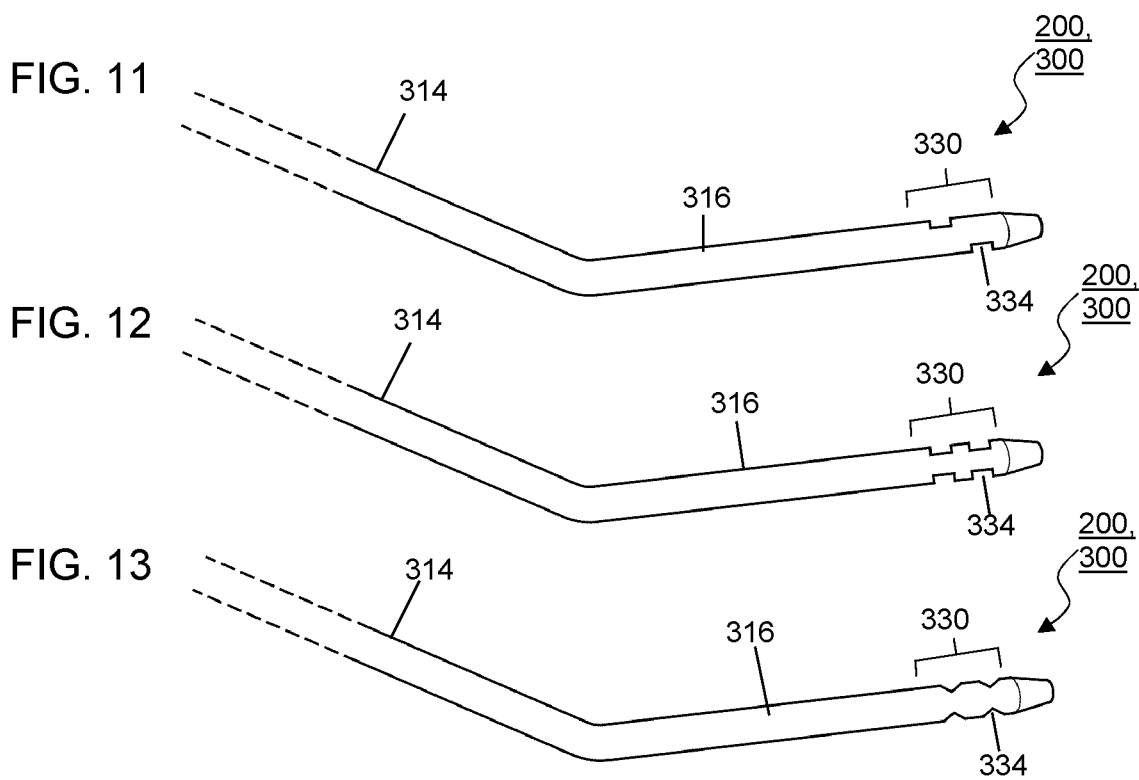
FIG. 11
FIG. 12
FIG. 13

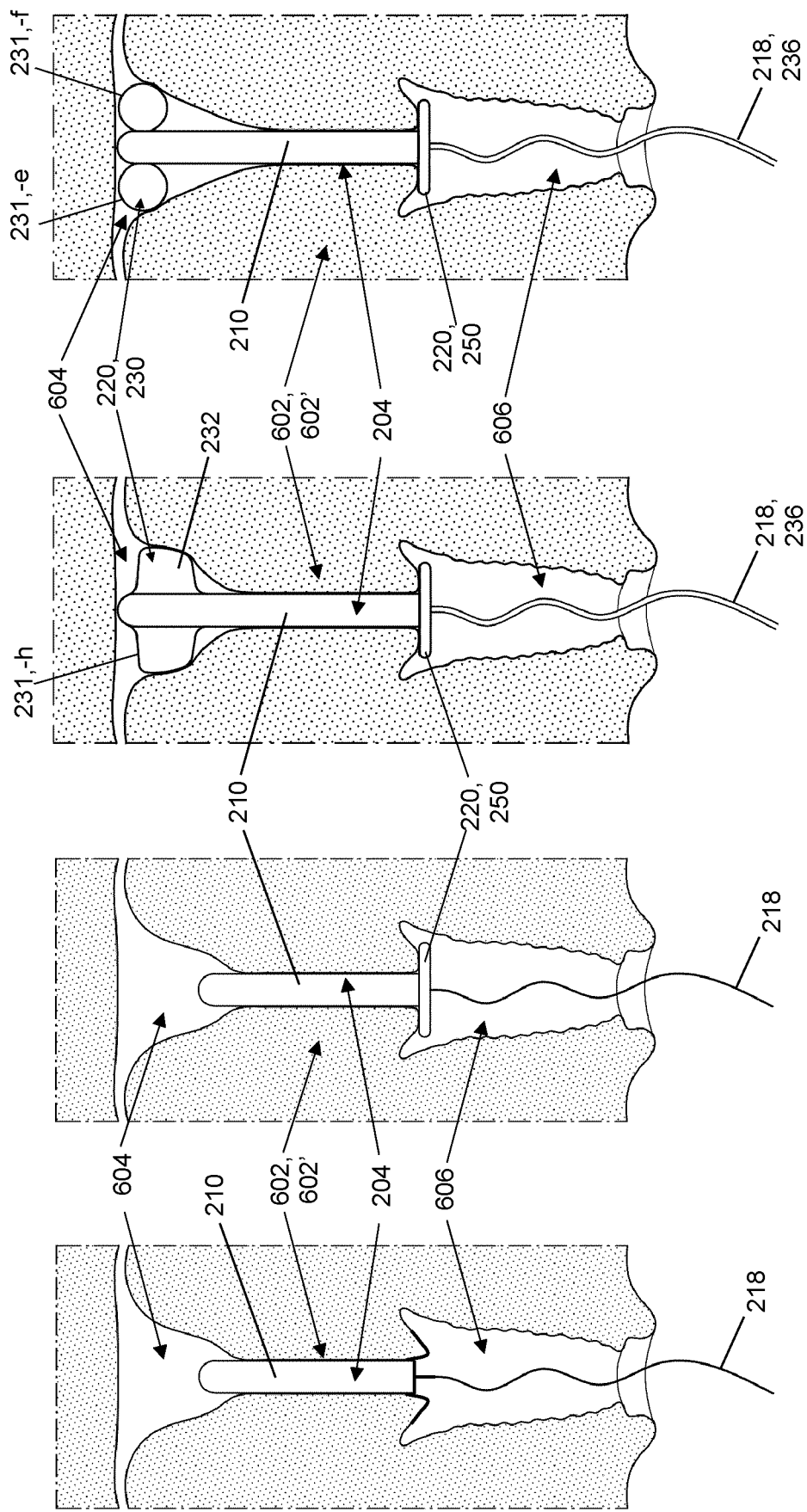

——— $a_{50/70}$: rectum dose, non-placed cervix at 50/70 Gy

·········· $a'_{50/70}$: rectum dose, placed cervix at 50/70 Gy

—·—·— $b_{50/70}$: bladder dose, non-placed cervix at 50/70 Gy

—··—··— $b'_{50/70}$: bladder dose, placed cervix at 50/70 Gy

—·—·—·— $c_{50/70}$: cervix dose, non-placed cervix at 50/70 Gy

—————— $c'_{50/70}$: cervix dose, placed cervix at 50/70 Gy

WEARABLE INSERTER FOR REPRODUCABLE ALIGNMENT OF BODILY TISSUE FOR PROGRAMME OF EXTERNAL RADIOTHERAPY TREATMENT

CROSS-REFERENCE TO RELATED APPLICATIONS

This application is a U.S. national stage entry under 35 U.S.C. § 371 of PCT International Patent Application No. PCT/EP2021/082759, filed Nov. 24, 2021, which claims priority to European Patent Application No. 20209522.0, filed Nov. 24, 2020, the contents of each of which are incorporated herein by reference in their entirety.

FIELD OF THE INVENTION

The present device and method concern the field of fractionated radiotherapy. In particular, it concerns a wearable device that can move and fix bodily tissue with respect to an ionising radiotherapy beam, so that the position of the tissue is accurately reproduced at each session of external radiotherapy treatment programme.

BACKGROUND

Radiation therapy is a standard treatment for many patients presenting with various cancers around the pelvic region. The majority of tissue structures lying around the pelvic region—bladder, rectum, cervix, uterus, vagina—are not affixed to pelvic walls and may move significantly from day when medical images of the treatment region are taken for treatment planning (treatment simulation), to the day when the first treatment by external radiotherapy is delivered, and optionally the subsequent days that form the duration of the whole radiotherapy programme. Where there has been a movement of such structures, the external radiotherapy is less effective because the ionising radiation is no longer aligned with the tumour target.

Often, external radiotherapy is fractionated meaning that lower radiation doses are delivered at frequent intervals (e.g. daily) to allow time for surrounding tissue to recover. The fractionated treatment may last for 6-7 weeks, and organ movements within the pelvis are unpredictable during this period of time. According to our own investigations, the cervix may move up to 2.2 cm in each direction, which requires an introduction of large volume margins around the original treatment zone (i.e. cervical cancer), increasing treated volume, which leads to higher rates of acute and late side effects. Movement of the uterine cervix between simulation and treatment, or between fractions may be caused by the filling or emptying of the bladder and the rectum and partially because of respiratory movements and bowel peristalsis. Therefore, patients are asked to empty their rectum and fill their bladder before each fraction. This allows a reduction in uterus displacements, but does not prevent them in a reproducible manner. Indeed, patients are often not able to keep the bladder filled to the same extent during the whole treatment duration (e.g. 28-30 fractions) because towards the end of radiotherapy, inflammation of the bladder prevents full filling. In addition, emptying the rectum brings both anterior and posterior rectal walls together inside the high dose isodose volumes surrounding the cervix with its 16-22 mm treatment margin, which induces the inclusion of the whole rectum inside the high isodose volume.

For a few years, treatment techniques using conformal radiotherapy (multileaf collimators, 360° radiotherapy, Cyberknife, Tomotherapy) allow the delivery of very high doses focally, while sparing healthy organs located around the tumor with a great accuracy. These technologies offer the greatest benefit provided the movements of the targets to be irradiated are reduced to the minimum. Nonetheless, they do not overcome the problem of movement of tissue structures from simulation to treatment and/or between fractionated treatment sessions.

US 2017/312546 A1 describes an immobilisation system for a rectal body cavity that monitors doses from an ionizing radiation source to a region-of-interest such as the prostate gland, however, the immobilisation system is not suitable to be worn by the subject for the period of the treatment programme (6-7 weeks), nor for reproducible. US 2008/293994 A1 describes a brachytherapy applicator and method, however, the devices and methods are directed to a different field of radiotherapy treatment—brachytherapy—where the source of radiation is disposed within the body and not externally. US 2008/097471 A1 describes systems, methods, apparatus and devices for performing improved gynecologic and urologic procedures, in particular, permitting simultaneous tissue cutting and removal from a target site. It is not related to external radiotherapy treatments.

Therefore, there is a need to create a system allowing repeatable fixing tissue structures in the pelvic region in order to benefit from high treatment accuracy.

SUMMARY

Provided is a positioning tool (200) for assisting treatment of a subject in an external radiotherapy programme comprising one or more external radiotherapy treatment sessions comprising:
  an inserter (204) having a proximal (40) and distal (20) end which inserter comprises:
    an elongated member (210) configured for insertion through an entrance to a canal (602) in connection with bodily tissue (610) of the subject, and provided with an elongated member lumen (214) configured for receiving an effector shaft (310) of a steering guide (300); and
    a guiding strand (218) for guiding the effector shaft (310) into the lumen (214) from outside the entrance to the canal, wherein the guiding strand (218) is disposed at least partially within the lumen (214) and is restrained at or towards a distal end (20) of the guiding strand (218) to limit or prevent sliding of the guiding strand (218) in a proximal direction relative to the lumen (214),
  a removable steering guide (300) having a proximal (40) and distal (20) end comprising:
    an effector shaft (310) disposed at the distal end (20) configured for repeatable removable insertion into the elongated member lumen (214) along the guiding strand (218), and
    a handle portion (316) disposed at the proximal end (40) in fixed relation to the effector shaft (310) for controlling the position and/or direction of the effector shaft (310),
  wherein the effector shaft (310) comprises a body provided with a guiding strand passage (312) for slidable movement along the guiding strand (218), the guiding strand passage (312) provided at least partially along a length of the body, wherein the positioning tool (200) is configured to move and/or fix the canal (602) and the bodily tissue (610) of the subject for the external radiotherapy treatment session.

Provided is a positioning tool (200) for assisting treatment of a subject in an external radiotherapy programme comprising one or more external radiotherapy treatment sessions comprising:
- an inserter (204) having a proximal (40) and distal (20) end which inserter comprises:
  - an elongated member (210) configured for insertion through an entrance to a canal (602) in connection with bodily tissue (610) of the subject, and provided with an elongated member lumen (214) configured for receiving an effector shaft (310) of a steering guide (300); and
  - a guiding strand (218) for guiding the effector shaft (310) into the lumen (214) from outside the entrance to the canal, wherein the guiding strand (218) is disposed at least partially within the lumen (214) and is restrained at or towards a distal end (20) of the guiding strand (218) to limit or prevent sliding of the guiding strand (218) in a proximal direction relative to the lumen (214), wherein the positioning tool (200) is configured to move and/or fix the canal (602) and the bodily tissue (610) of the subject relative to an ionising radiotherapy beam for the external radiotherapy treatment session.

The canal may be a cervix and/or uterus and/or vaginal vault mass of the subject and the bodily tissue may be tissue comprised in the pelvic region, and the entrance to the canal may be the entrance to the cervix or a canal inside a vaginal vault mass.

The elongated member (210) may be provided with at least one slide restrictor (220) configured to reduce or prevent sliding of the elongated member (210) relative to the canal.

At least one slide restrictor (220) may be an inflatable balloon assembly (230) comprising one or more inflatable balloon(s) (231,-a to -h), or an expandable stent (240), a distal protrusion (245) or a stop member (250).

The inflatable balloon assembly (230) may comprise one or more inflatable balloon(s) (231,-a to -h) each having an inflatable balloon lumen (232) in fluid connection with an inflation lumen (234) extending via an inflation tube (236) in a proximal (40) direction. The guiding strand (218) may be the inflation tube (236).

The positioning tool (200) may be provided with at least two slide restrictors (220):
- a first slide restrictor comprising the stop member (250) provided at a proximal end (40) of the elongated member (210) and is configured to abut with the canal entrance, optionally wherein the stop member (250) is provided with one or more suture channels (252) for suturing the entrance to the canal, and
- a second slide restrictor comprising:
  - the inflatable balloon assembly (230), or
  - the distal protrusion (245), or
  - the expandable stent (240),
  provided at a distal end (20) of the elongated member (210).

The guiding strand (218) may be non-dismountably or dismountably attached in relation to the lumen (214).

The guiding strand (218) may be a flaccid tube (237) configured to receive a stiffening stylet.

At least a part of the inserter (204) or one or more imaging markers borne thereby, may be visible by medical imaging, in particular by X-ray medical imaging and/or by MR medical imaging, and/or
 at least a part of the elongated member (210) or one or more imaging markers borne thereby, may be visible by medical imaging, in particular by X-ray medical imaging and/or by MR medical imaging, and/or
 the inserter (204) or elongated member (210) may be disposed with one or more radio transponders for determining a position and/or orientation of the inserter (204) and/or elongated member (210) in real-time by a spatial transponder detector, or
 the elongated member (210) may be not visible by X-ray imaging.

The positioning tool (200) may further comprise a removable steering guide (300) having a proximal (40) and distal (20) end comprising:
 n effector shaft (310) disposed at the distal end (20) configured for repeatable removable insertion into the elongated member lumen (214) along the guiding strand (218), and
 a handle portion (316) disposed at the proximal end (40) in fixed relation to the effector shaft (310) for controlling the position and/or direction of the effector shaft (310).

The effector shaft (310) may comprise a body provided with a guiding strand passage (312) for slidable movement along the guiding strand (218), the guiding strand passage (312) provided at least partially along a length of the body. The guiding strand passage (312) may be a groove or lumen in the body effector shaft (310).

The effector shaft (310) body may be rigid, the elongated member (210) may be flexible and become stiffened by insertion into the elongated member lumen (214) of the effector shaft (310).

The handle portion (316) may be configured for attachment to a positioning device, which positioning device is configured to adjust and fix the position and/or orientation of the effector shaft (310),
 optionally wherein
  the handle portion (316) is provided with a grip locator (330) configured to co-operate with an end effector fitting of the positioning device for dismountable, repeatable, and reproducible attachment of the handle portion (316) to the positioning device.

The removable steering guide (300) further may comprise:
 a transmission (314) joining the handle portion (316) to the effector shaft (310)
 optionally, an inflatable transmission balloon (322) provided towards a distal (20) end of the transmission (314), wherein:
  optionally the inflatable transmission balloon (322) has a fixed maximum inflation diameter, and/or
  optionally, the inflatable transmission balloon (322) bears one or more imaging markers visible by medical imaging, and/or
  optionally, the inflatable transmission balloon (322) bears one or more radio transponders for determining a position and/or orientation of the transmission (314) and/or of the effector shaft (310) in real time by a spatial transponder detector.

At least a part of the effector shaft (310) and/or one or more imaging markers borne by the effector shaft (310) is visible by medical imaging, in particular by X-ray medical imaging and/or magnetic resonance, MR, medical imaging; and/or
 at least a distal part the transmission (314) and/or or one or more imaging markers borne by the effector shaft (310), is visible by medical imaging, in particular by X-ray medical imaging or MR medical imaging;

and/or
  the transmission (314) and/or the effector shaft (310) is disposed with one or more radio transponders for determining a position and/or orientation of the transmission (314) and/or of the effector shaft (310) in real-time by a spatial transponder detector.

The handle portion (316) of the steering guide (300) may be disposed with a docking beacon (340) configured to provide real-time information as to the position and optionally orientation of the steering guide (300) to allow manual, semi-automatic or automatic docking guidance of the positioning device with the handle portion (316).

The movement of the canal (602) by the positioning tool (200):
  may bring bodily tissue (608) connected to the canal (602) into the ionising radiation beam emitted by an ionising-radiation treatment head (518) during the external radiotherapy treatment session,
or
  may move bodily tissue (608) connected to the canal (602) away from ionising radiation beam emitted by an ionising-radiation treatment head (518) during the external radiotherapy treatment session.

Further provided is a system comprising:
  the positioning tool (200) as described herein;
  the positioning device for adjusting and fixing a position and/or orientation the handle portion (316) and of the effector shaft (310) of the positioning tool (200);
wherein
  the handle portion (316) is configured for dismountable attachment to the positioning device; and
  the positioning device is a robotic arm.

FIGURE LEGENDS

FIG. 1 depicts an isometric view of inserter provided herein.

FIG. 2A depicts a longitudinal cross-sectional view of an inserter provided herein disposed with a guiding strand for dismountable attachment to a steering guide.

FIG. 2B depicts a longitudinal cross-sectional view of an inserter provided herein disposed with a removable (dismountable) guiding strand with ball-stop, the inserter provided for dismountable attachment to a steering guide.

FIG. 2C depicts a longitudinal cross-sectional view of an inserter provided herein disposed with a removable (dismountable) guiding strand with threaded distal end, the inserter provided for dismountable attachment to a steering guide.

FIG. 2D depicts the removable (dismountable) guiding strand of FIG. 2C with threaded distal end.

Figure 3:
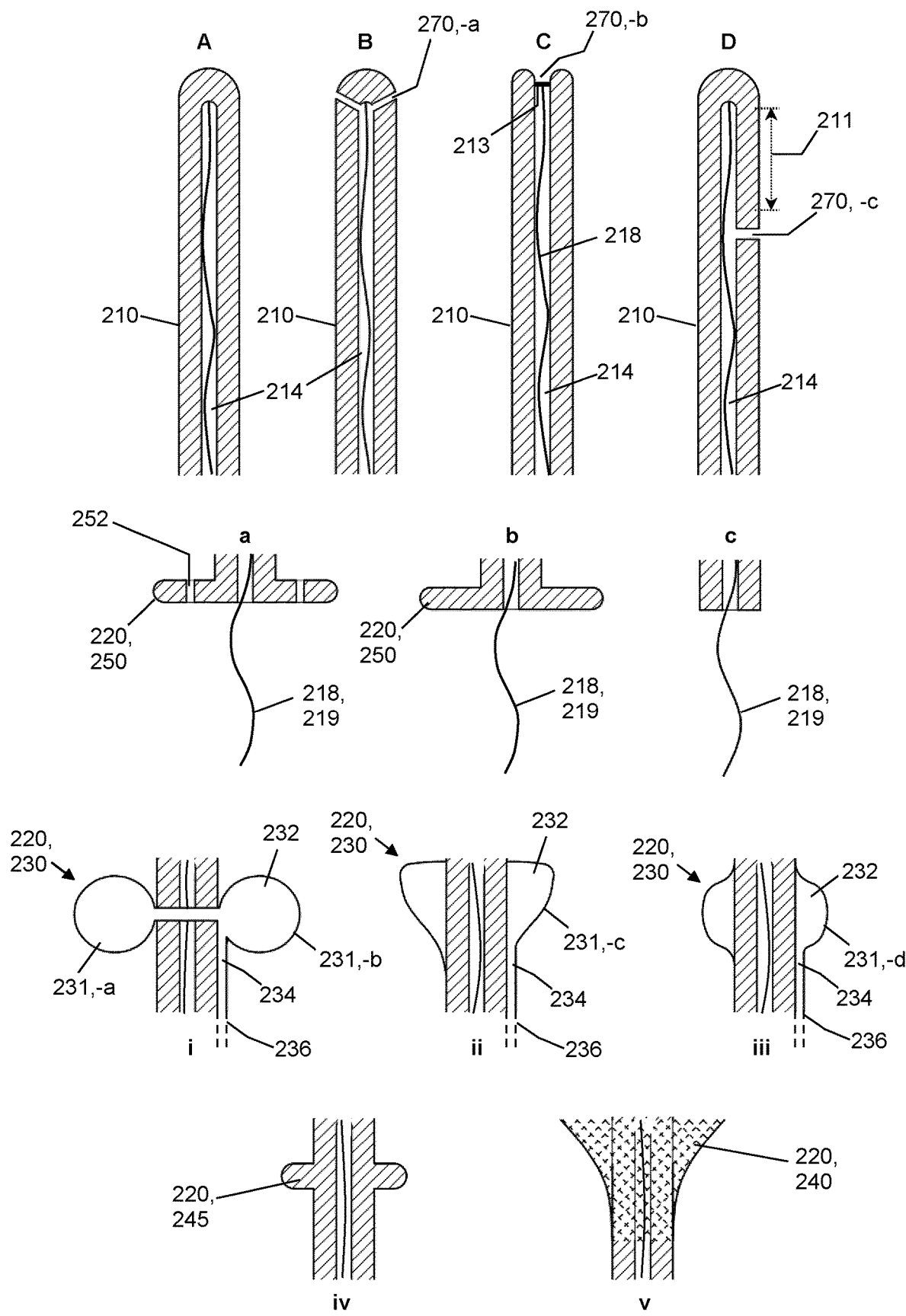

FIG. 3 depicts different elements of an inserter that are combinable including elongated member (A to D), proximal slide restrictor (a to b) or none (c), distal slide restrictor (i to v), wherein the guiding strand is a flexible cord; elongated member (G to J), proximal slide restrictor (g to j), wherein the guiding strand is an inflation tube; elongated member (K to L), proximal slide restrictor (k to l) or none (m), distal slide restrictor (xi to xv), wherein the guiding strand is dismountably attached to the elongated member; elongated member (M to 0), proximal slide restrictor (n to o) or none (p), distal slide restrictor (xvi to xx), wherein the guiding strand is a flaccid tube.

FIG. 4 shows an enlarged view of an inflation tube (236) within an inflation lumen (234).

Figure 5:
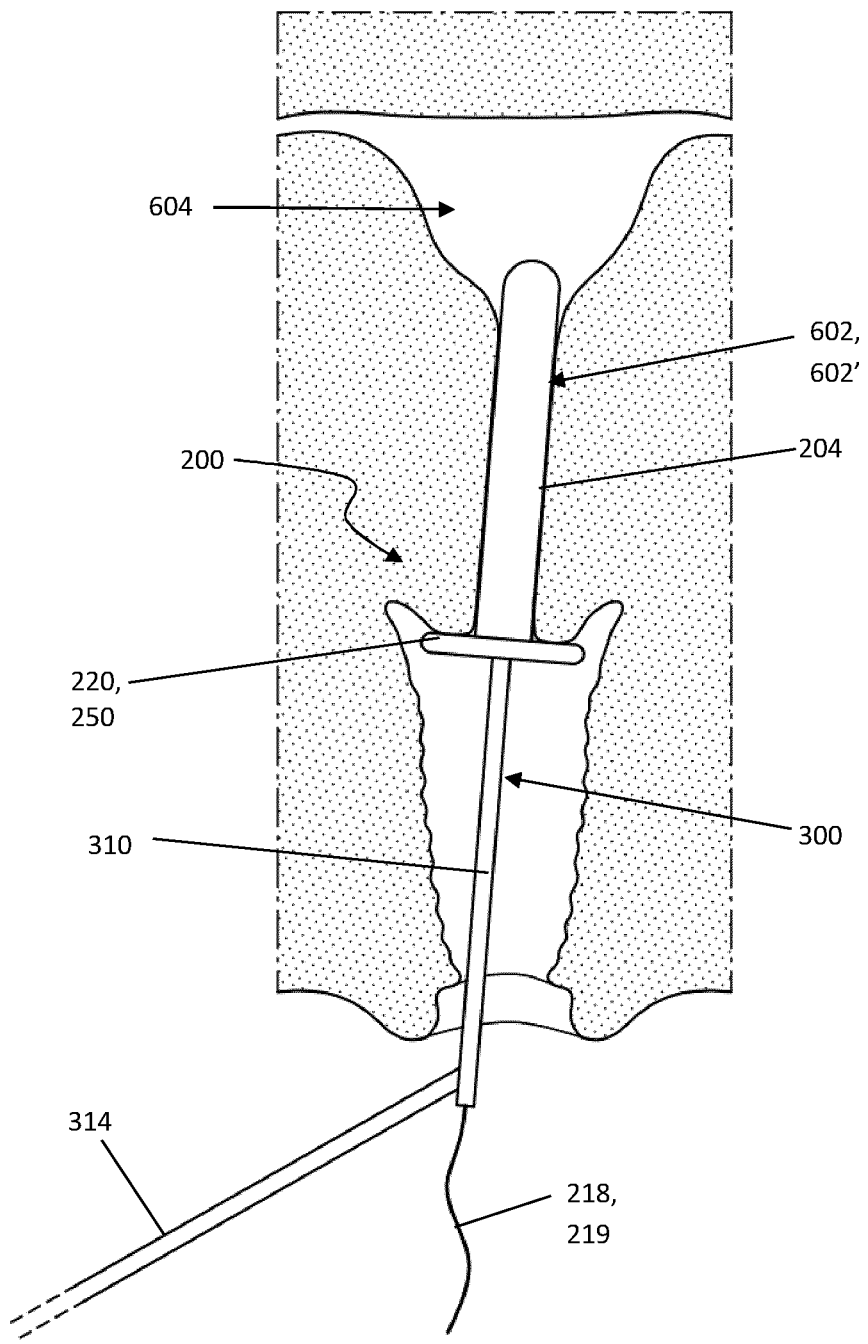
Figure 14:
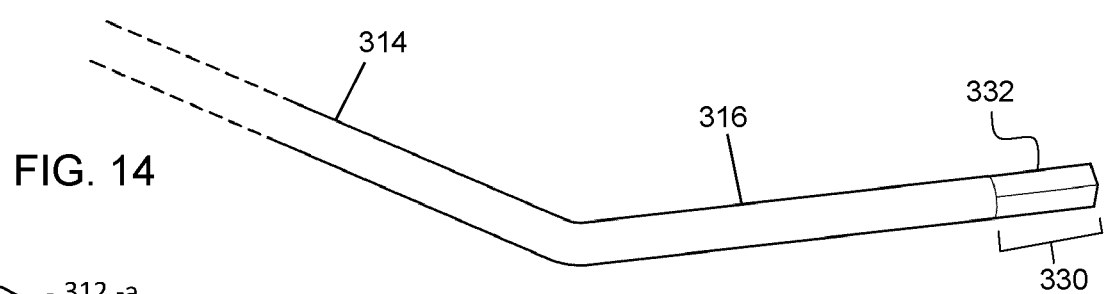

FIG. 5 shows a positioning tool (200) described herein with an inserter (200) and steering guide (300); the inserter located in the cervical canal.

FIG. 6 depicts an exemplary steering guide provided herein, with alternative placements of guiding strand passage exit.

FIG. 6A depicts angle gamma viewed along eyeline (e) in FIG. 6

FIGS. 7 and 8 each depict a configuration of a steering guide with a one-piece polymeric handle and transmission, and each having a different configuration of guiding strand passage exit of the steering guide.

FIG. 9 depicts a steering guide provided with an inflatable transmission balloon.

FIG. 10 depicts a steering guide where the guiding strand passage is a slot; detail of an entrance to the slot is shown in FIG. 10A.

FIGS. 11 to 14 depict an alternative configuration handle portion (316) notches of the steering guide.

Figure 15:
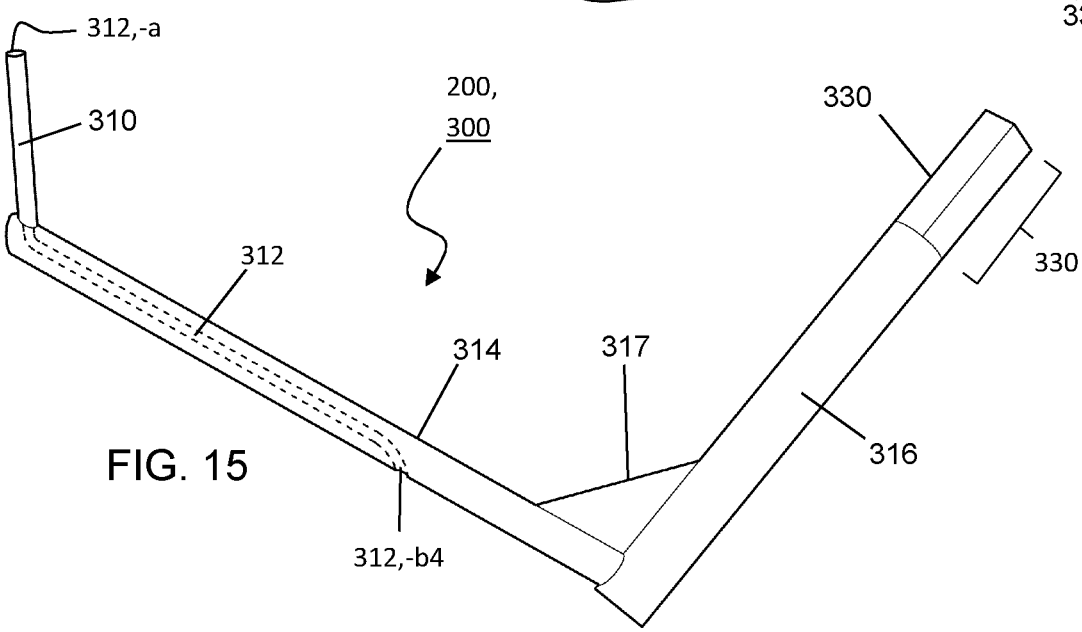

FIGS. 15, A to C shows a configuration of a steering guide with a one-piece polymeric handle and transmission, and with a handle portion (316) containing a notch and corner.

Figure 16:
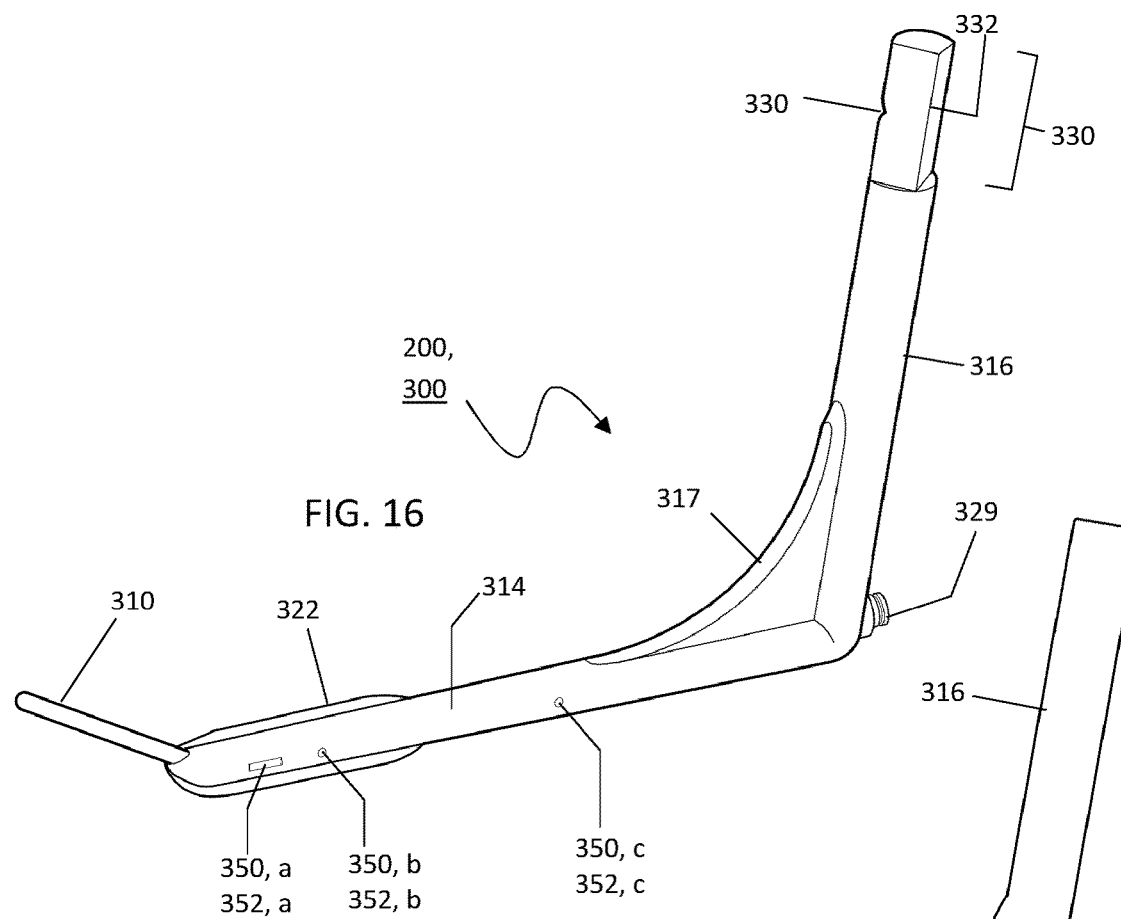

FIG. 16 shows a configuration of a steering guide as similar to that of FIG. 15, additionally provided with a transmission balloon.

Figure 17:
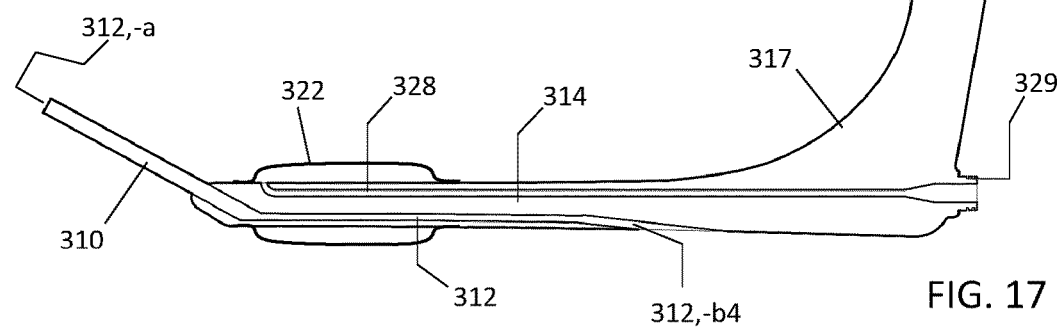

FIG. 17 shows a longitudinal cross-section of the steering guide of FIG. 16.

Figure 18:
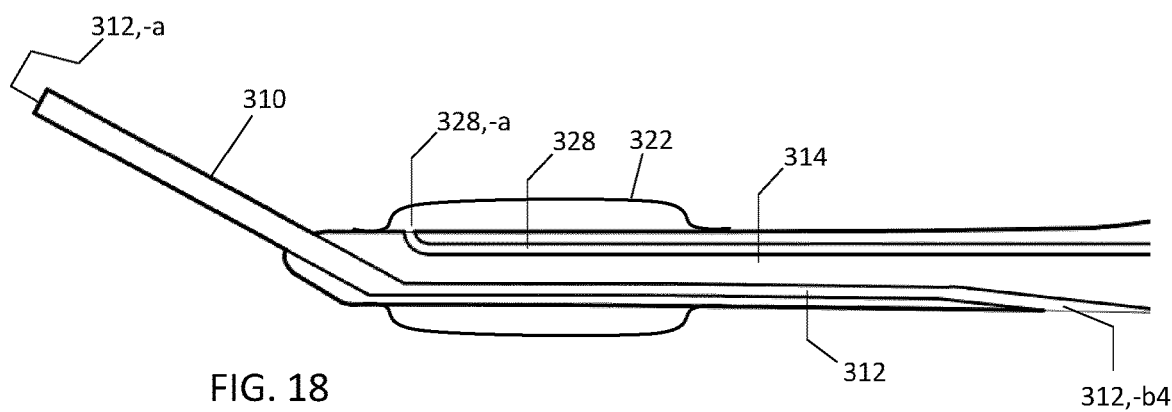

FIG. 18 shows an enlargement of the lumens of FIG. 17.

Figure 19:
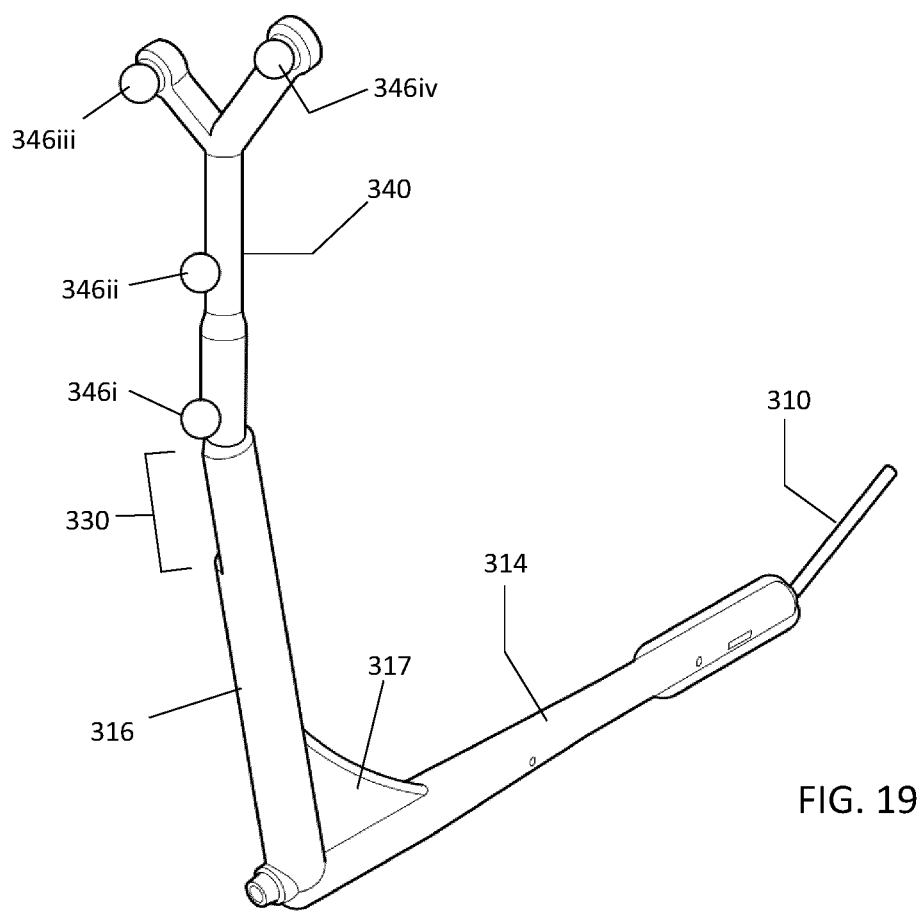
Figure 20:
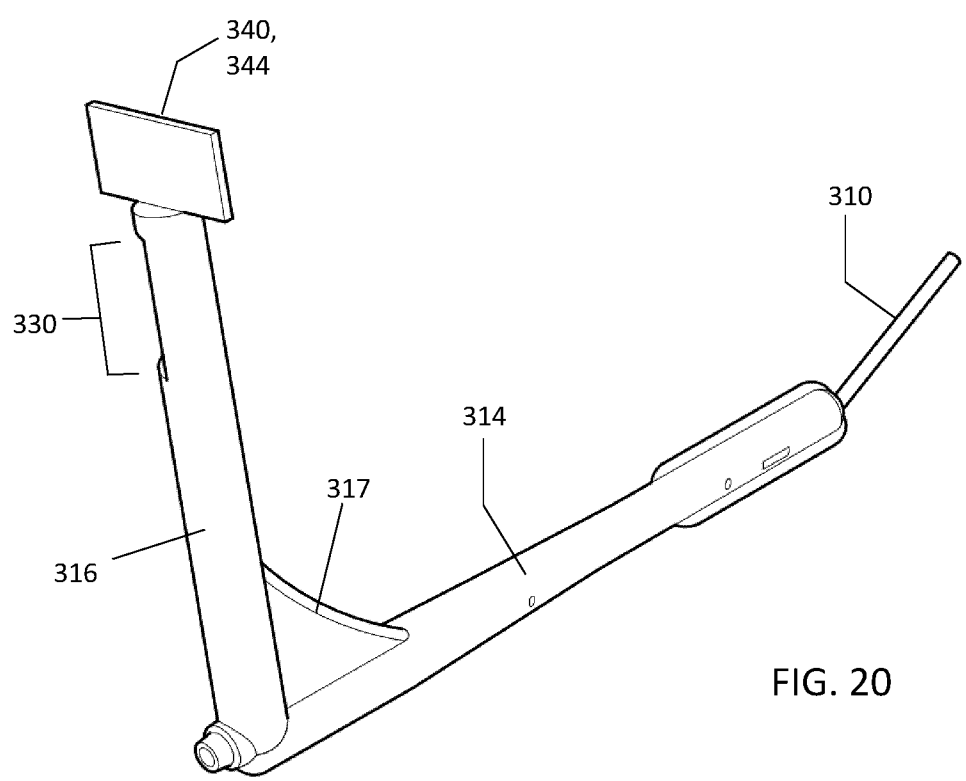
Figure 21:
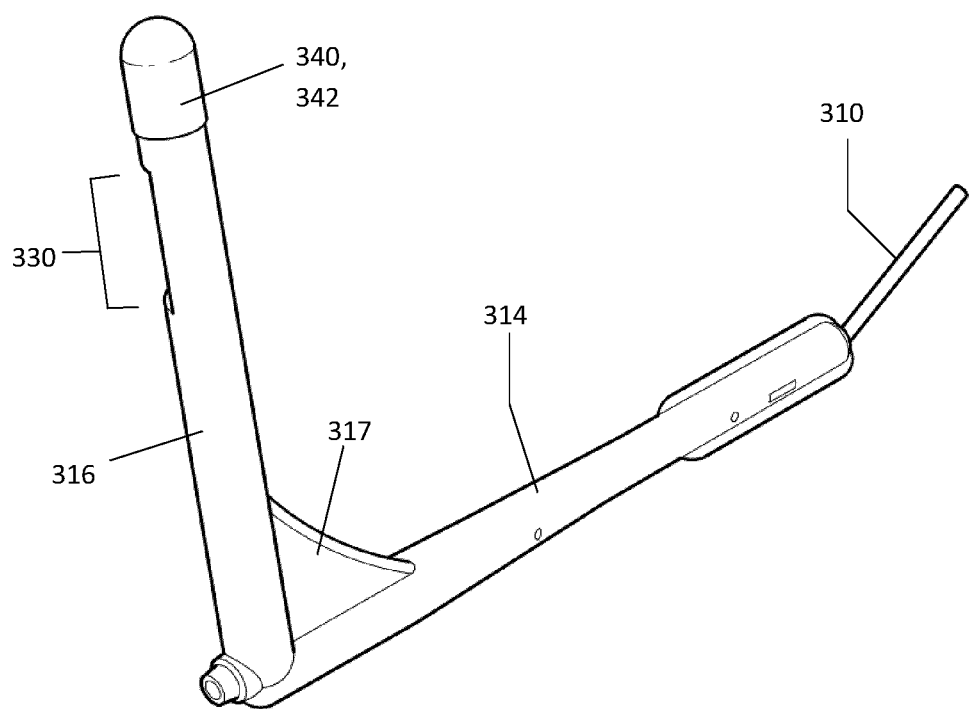

FIGS. 19 to 21 each show a steering guide provided with a different docking beacon.

FIGS. 22 to 25 show different inserters located in the cervical canal.

Figure 26:
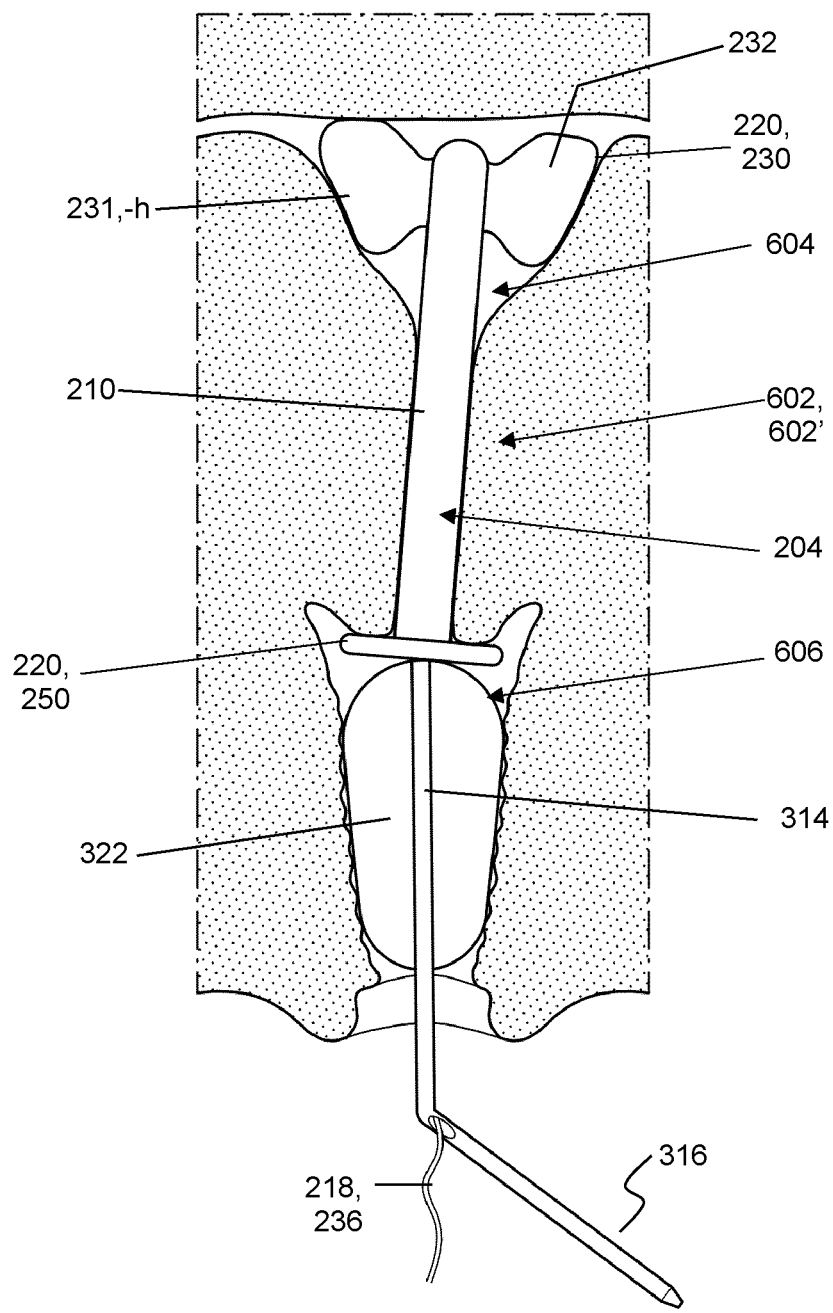

FIG. 26 shows a positioning tool comprising an inserter provided herein located in the cervical canal, and mounted on the steering guide, and movement of the steering guide changing the position of the cervix and uterus.

Figure 27:
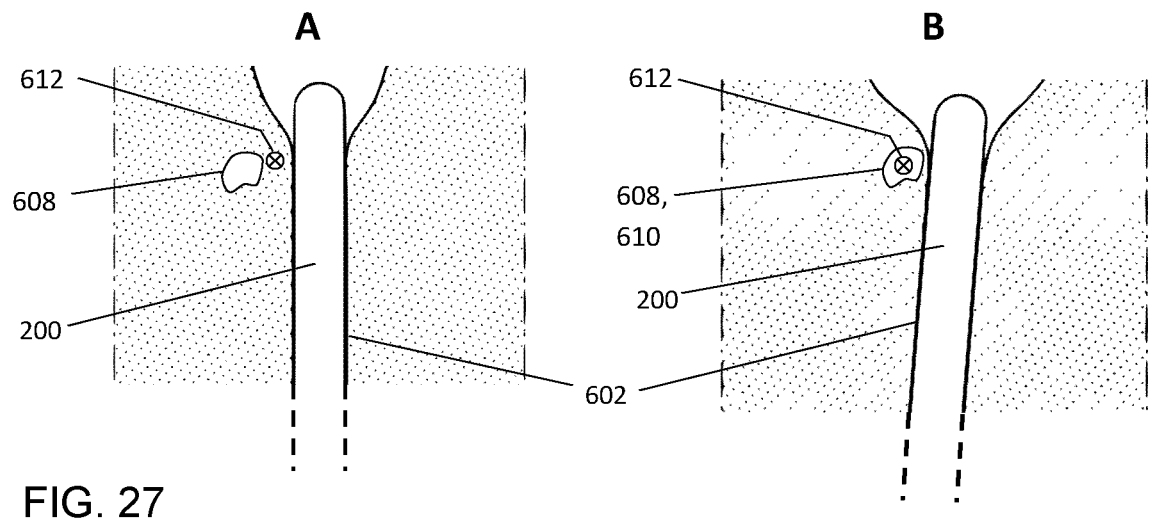
Figure 28:
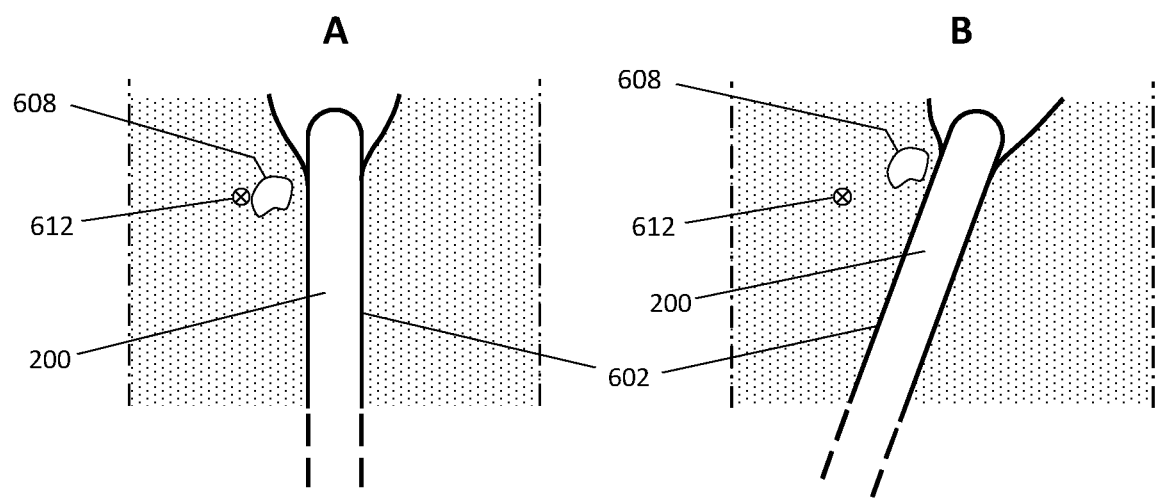

FIGS. 27 and 28—illustrations of a positioning tool inserted into the canal, where the different poses (A and B) of the positioning tool change the position of bodily tissue.

Figure 29A:
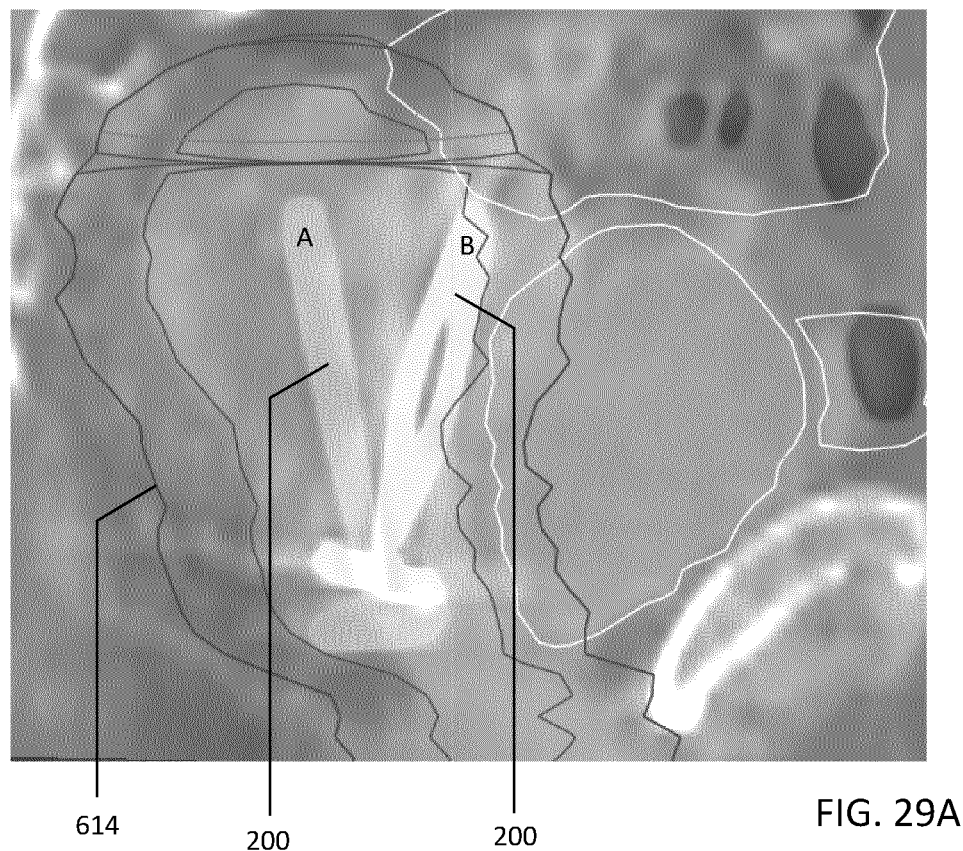
Figure 29B:
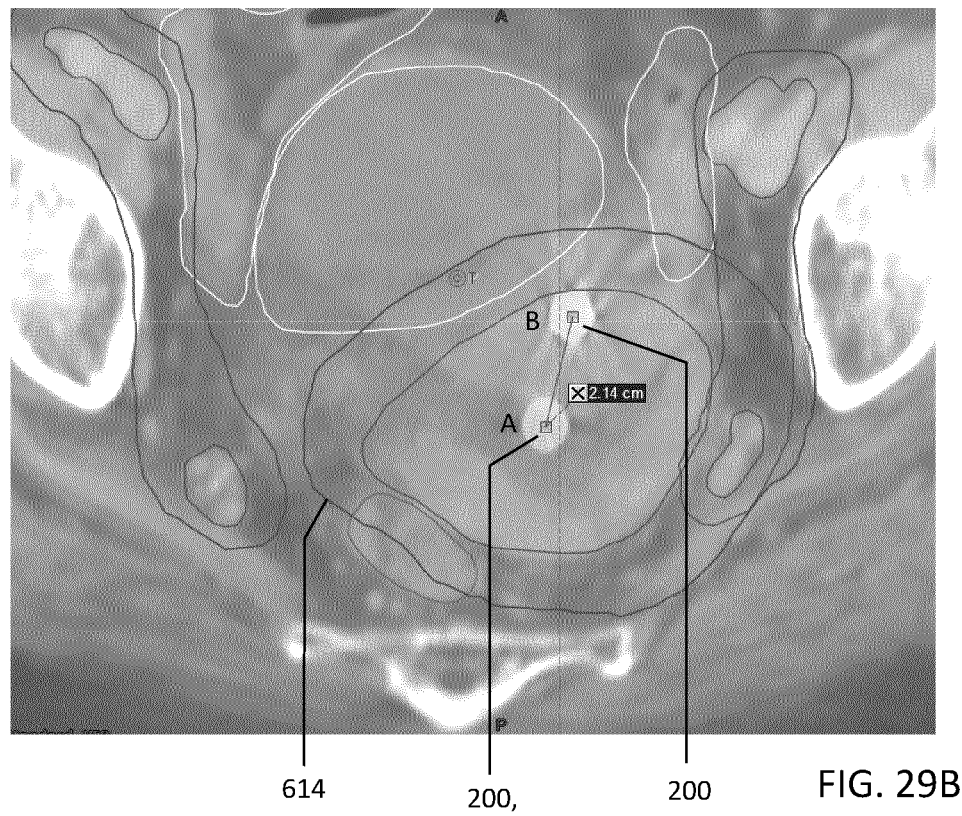

FIGS. 29A and 29B each show a composite medical image illustrating a change inserter pose recorded during simulation and during a treatment session and prior to commencement of exposure. FIG. 29A is a side view of inserter, FIG. 29B is an axial view of inserter.

Figure 30:
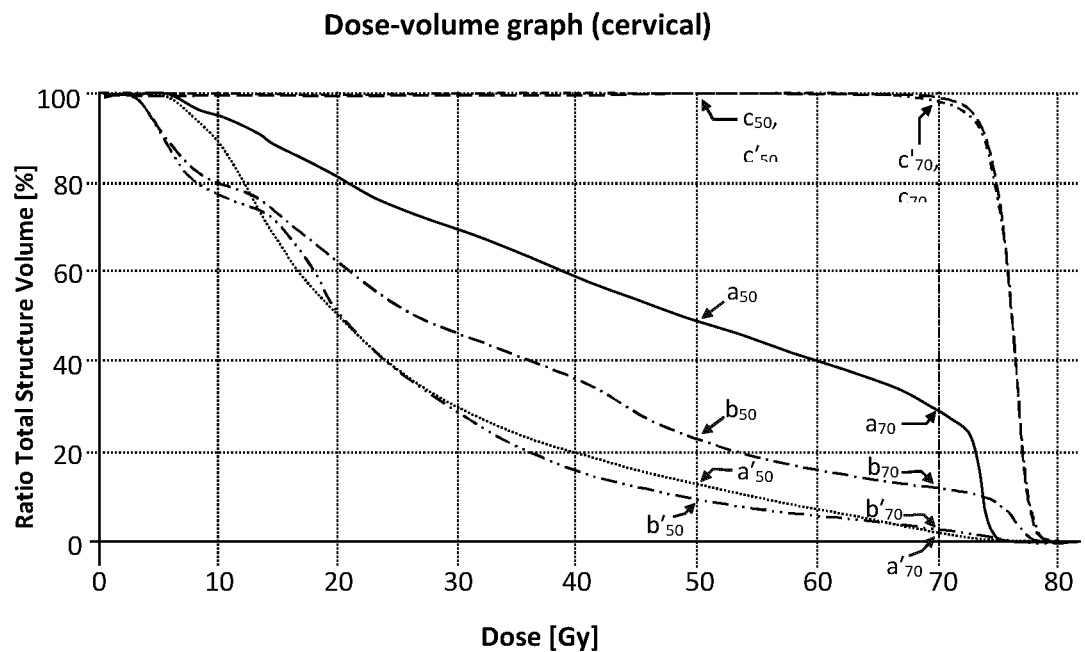

FIG. 30 is a Dose-Volume graph indicating dose/volume distribution received by a structure for rectum, bladder and cervix when the cervix is not immobilised (a, b, c respectively) or when the cervix is immobilised (a', b', c').

DETAILED DESCRIPTION

Before the present tool and method of the invention are described, it is to be understood that this invention is not limited to particular systems and methods or combinations described, since such tools and methods and combinations may, of course, vary. It is also to be understood that the terminology used herein is not intended to be limiting, since the scope of the present invention will be limited only by the appended claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of".

The recitation of numerical ranges by endpoints includes all numbers and fractions subsumed within the respective ranges, as well as the recited endpoints.

The term "about" or "approximately" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" or "approximately" refers is itself also specifically, and preferably, disclosed.

Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members.

All references cited in the present specification are hereby incorporated by reference in their entirety. In particular, the teachings of all references herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

In the present description of the invention, reference is made to the accompanying drawings that form a part hereof, and in which are shown by way of illustration only of specific embodiments in which the invention may be practiced. Parenthesized or emboldened reference numerals affixed to respective elements merely exemplify the elements by way of example, with which it is not intended to limit the respective elements. It is to be understood that other embodiments may be utilised and structural or logical changes may be made without departing from the scope of the present invention. The following detailed description, therefore, is not to be taken in a limiting sense, and the scope of the present invention is defined by the appended claims.

The terms "distal", or "distal side", or "distal to" and "proximal", or "proximal side", or "proximal to" are used through the specification, and are terms generally understood in the field to mean towards (proximal) or away (distal) from the practitioner's side of the apparatus. Thus, "proximal" means towards the practitioner's side and, therefore, away from the subject's side. Conversely, "distal" means towards the subject's side and, therefore, away from the practitioner's side.

The term "longitudinal" is generally understood in the field to mean along the longer length of the treatment or simulation table. It may be used to refer to the radiotherapy treatment or simulation table itself, or to a device attachable to the radiotherapy treatment or simulation table, or to a subject lying on the radiotherapy treatment or simulation table.

The term "lateral" is generally understood in the field to mean along a shorter length of the treatment or simulation table i.e. from side-to-side or left to right. It may be used to refer to the radiotherapy treatment or simulation table itself, or to a device attachable to the radiotherapy treatment or simulation table, or to a subject lying on the radiotherapy treatment or simulation table.

The term "superior" is understood to mean towards a head of a subject. It may be used to refer to the radiotherapy treatment or simulation table, or to a device attachable to the radiotherapy treatment or simulation table, or to a subject lying on the radiotherapy treatment or simulation table. The term "inferior" is understood to mean towards the feet of a subject. It may be used to refer to the radiotherapy treatment or simulation table, or to a device attachable to the radiotherapy treatment or simulation table, or to a subject lying on the radiotherapy treatment or simulation table.

Provided herein, is a positioning tool for assisting in treatment of a subject for an external radiotherapy programme. The external radiotherapy programme comprises a least one session or fraction of external radiotherapy treatment and/or a simulation of treatment. The positioning tool (200) comprises an inserter (204) (e.g. FIGS. 1, 2A to 2D) having a proximal (40) and distal (20) end. The inserter (204) comprises an elongated member (210) configured for insertion through an entrance to a canal in connection with the bodily tissue. The elongated member (210) may be dimensioned for engaging with the wall of the canal so that movement of the positioning tool (200) causes movement of the canal. The elongated member (210) is provided with an elongated member lumen (214) configured for receiving an effector shaft (310) of a steering guide (300) (e.g. FIG. 6). The effector shaft (310) may be configured to co-operate with the elongated member (210) such that movements of the steering guide are transferred to the elongated member (210). The effector shaft (310) may be further configured to stiffen at least a substantial part of the elongated member (210) when elongated member (210) is flexible. The inserter (204) elongated member lumen (214) may be configured for repeatable dismountable attachment to the steering guide (300) effector shaft (310). The inserter (204) further comprises a guiding strand (218) for guiding the effector shaft (310) into the lumen (214) from outside the entrance to the canal. A distal end (20) of the guiding strand (218) is attached in fixed relation to the lumen (214).

Movement of the canal by the positioning tool (200) causes movement of bodily tissue of the subject in relation to the external ionising radiotherapy beam, in particular in relation to a beam intersection volume of an external ionising radiotherapy beam. A position and/or orientation (pose) of the positioning tool is adjustable and fixable for a duration of at least a part of the treatment session. The fixed pose of the positioning tool stably fixes the position of the bodily tissue relative to the ionising radiotherapy beam. FIGS. 27 and 28 exemplify the invention. Movement of the canal by the positioning tool (200) may bring the bodily tissue of a subject into alignment with an ionising radiotherapy beam, e.g. with an ionising radiotherapy isodose volume, as it has been defined during patient simulation under CT scan or MR. Alternatively, movement of the canal by the positioning tool (200) may move and/or fix the bodily tissue of a subject away from an ionising radiotherapy beam, e.g. to protect that structure.

FIG. 27, Panel A depicts a positioning tool (200) inserted in a canal (602) of the subject and bodily tissue (608) connected to the canal (602). By adjusting the pose of the positioning tool (200) (Panel B), the position of bodily tissue (608) can be stabilised, adjusted and fixed relative to the ionising-radiation beam emitted by an ionising radiation head, in particular to a beam intersection volume (612) (e.g. isocentre). The beam intersection volume (612) has a constant position in Panels A and B. In the case of FIG. 27 Panel B, bodily tissue (608) is also a treatment target (610) that is brought into the beam intersection volume (612) for exposure to ionising-radiation. The pose of the positioning tool (200) can be recorded and re-applied in subsequent sessions of fractionated treatment.

FIG. 28 Panel A depicts a positioning tool (200) inserted in a canal (602) of the subject and bodily tissue (608) connected to the canal (602). By adjusting the pose of the positioning tool (200) (FIG. 28 Panel B), the position of bodily tissue (608) can be stabilised, adjusted and fixed relative to the ionising-radiation beam emitted by an ionising radiation head, in particular to a beam intersection volume (612) (e.g. isocentre). The beam intersection volume (612) has a constant position in Panels A and B. In the case of FIG. 28 Panel B, bodily tissue (608) is not a treatment target (610) and it is brought outside the beam intersection volume (612) for avoiding exposure to ionising-radiation. The pose of the positioning tool (200) can be recorded and re-applied in subsequent sessions of fractionated treatment.

The extent of movement of internal organs or tissue in a subject between simulation and treatment, or between treatment sessions is illustrated in FIGS. 29A to 29B. Each figure is a fused X-ray image of a subject undergoing simulation and treatment for a cervical tumour in which the positioning tool (200) inserter (204) presently described has been inserted into the cervical canal, wherein the images taken during simulation and the subsequent $1^{st}$ treatment session were superimposed. The external margin (614) of the irradiated volume is indicated.

A first pose (A) of the positioning tool (200) inserter (204) adopted in simulation corresponded to a natural placement of tissues and organs and there was minimum of active pose adjustment by the robotic arm. A second positioning tool (200) inserter (204) pose (B) was recorded in a subsequent $1^{st}$ treatment session prior to adjustment by the robotic arm. There was a significant difference between the first (A) and second (B) poses due to the internal movements of the tissues and organs between the sessions that caused displacement of the inserter (204) tip by around 2.1 cm, and a corresponding shift in the position of the treatment target.

The new pose (B) was on the external margin of the irradiated volume, and would have received a much lower dose than calculated. The internal movement was corrected by the present systems and methods by an adjustment to the pose of the positioning tool (200) inserter (204) by the robotic arm during the treatment session to correspond with the pose recorded during simulation, leading to a significant reduction in toxicity.

The effect of the positioning tool on toxicity reduction in adjacent structures is illustrated in FIG. 30 which is a dose-volume histogram chart illustrating the relationship between the percentage of irradiated volume of each organ (rectum, bladder, cervix) and the dose received by said irradiated volume for the rectum (a, a'), bladder (b, b') and cervix (c, c') that was calculated for an external radiotherapy treatment of the cervix when the cervix was not placed (natural position) (a, b, c) and when the cervix was placed (a', b', c') using the positioning tool. The rectum (a, a') and bladder (b, b') are recipients of radiation toxicity when the cervix is the treatment target. The margins in the present calculation were 16 mm when the cervix was not placed (large margins) and 5 mm when the cervix was placed using the positioning tool.

For the rectum (a, a'), when the cervix was not placed using the positioning tool, 50% of the rectum volume received a dose of 50 Gy ($a_{50}$); when the cervix was placed with the positioning tool 13% of the rectum volume received a dose of 50 Gy ($a'_{50}$). When the cervix was not placed, % of the rectum volume received a dose of 70 Gy ($a_{70}$); when the cervix was placed with the positioning tool 2.5% of the rectum volume received a dose of 70 Gy ($a'_{70}$). Hence, with the positioning tool placement of the cervix, the dose volume received by the rectum was reduced from 50% to 13% at 50 Gy (3.9 fold reduction) and from 30% to 2.5% at 70 Gy (12 fold reduction).

For the bladder (b, b'), when the cervix was not placed 22% of the bladder volume received a dose of 50 Gy ($b_{50}$); when the cervix was placed with the positioning tool 10% of the bladder volume received a dose of 50 Gy ($b'_{50}$). When the cervix was not placed 12% of the bladder volume received a dose of 70 Gy ($b_{70}$); when the cervix was placed with the positioning tool 3% of the bladder volume received a dose of 70 Gy ($b'_{70}$). Hence, with the positioning tool placement of the cervix, the dose volume received by the bladder was reduced from 22% to 10% at 50 Gy (2.2 fold difference) and from 12% to 3% at 70 Gy (4 fold reduction).

For the cervix (c, c'), 100% of the cervix volume received a dose of 50 Gy ($c_{50}$) when the cervix was not placed; when the cervix was placed with the positioning tool 100% of the cervix volume also received a dose of 50 Gy ($c'_{50}$). When the cervix was not placed ~98% of the cervix volume received a dose of 70 Gy ($c_{70}$); when the cervix was placed with the positioning tool, ~99.5% of the cervix volume received a dose of 70 Gy ($c'_{70}$). Hence, the positioning tool did not affect the cervix volume/dose, and lead to a slight increase in volume of cervix receiving the higher 70 Gy dose.

The results in FIG. 30 demonstrate that high doses can be delivered externally to the cervix while reducing complications caused by irradiation of the rectum and bladder. Conventionally, such higher doses would be need delivered by brachytherapy (internal radiation source) which is more targeted for internal structures but is more complex and a highly uncomfortable procedure due to the need for complex intervention. Indeed, the majority of patients with cervical cancer, who are not operable because of vaginal or parametrial invasion, will need an implant of invaded structures with brachytherapy needles, with the need of anaesthesia and hospitalization. This is feasible in only a limited number of radiotherapy centers and this makes this treatment not accessible in all patients. This complex brachytherapy intervention could be avoided by immobilising and placing the cervix using the present positioning tool (200). The immobilization and placement of the cervix allows doses to the cervix to be boosted without excessive toxicity on surrounding tissues and would suppress the need for brachytherapy.

The canal (602) can be accurately moved and/or fixed by the positioning tool (200) in order to change and fix the position of canal and bodily tissue relative to the external ionising radiotherapy beam. The bodily tissue may be in the canal, or may be a structure that moves when the canal is moved (e.g. prostate that moves with the rectal canal or uterus that moves with cervical canal). The canal (602) of the subject is preferably a canal (passageway) of a natural bodily structure structure such as cervical canal (602') and/or uterus (604), vagina (606), a canal made inside a vaginal vault mass (tumor or tumor recurrence). In FIGS. 22 to 26, the positioning tool (200) is located within the cervical canal (602'). The canal may be a canal formed by surgery e.g. in the vaginal vault or in a tissue mass such as a breast.

The bodily tissue (608) of a subject in connection with the canal refers to tissue that is moveable by changing the spatial position and/or orientation of the canal i.e. by changing the spatial position and/or orientation (pose) of the positioning tool (200). In other words, the canal is in moveable connection with the bodily tissue. The bodily tissue may be part of a wall of the canal, or a different tissue structure whose position and/or orientation is affected by movement of the canal. For instance, the position and/or orientation of the bladder, vagina, uterus and rectum can be changed by changing the changing the spatial position and/or orientation (pose) of the inserter (204) or effector shaft (310) in the cervical canal.

The bodily tissue (608) may be tissue that is a target (610) of treatment (e.g. a tumour) and is to be brought into the external ionising radiotherapy beam for exposure to the beam; accordingly, the target(s) for receiving treatment is (are) highly accurately positioned, allowing receipt of maximal dose and reducing damage to healthy structures. Alternatively, the bodily tissue may be tissue that is to be moved out of the external ionising radiotherapy beam thereby avoiding exposure to the beam; accordingly, healthy tissue can be displaced away from a target, allowing a more isolated exposure.

The bodily tissue (608) may be a tissue or tissue of an organ. The bodily tissue may be a tissue structure in the pelvic region such the cervix uteri, corpus uteri, rectum, bladder, vagina that can be moved by changing the position and/or orientation of the cervix and/or uterus and/or vagina. The bodily tissue may be tissue structures in the region surrounding the uterus and vagina such as the rectum, lower colon, bladder that can be moved by changing the position and/or orientation of the uterus and the vagina. It is appreciated that positioning tool may be used in the treatment of multiple tissues that lie adjacent to the canal.

During simulation under medical imaging, the canal (602) can be accurately placed or moved by the positioning tool (200) in order to align the bodily tissue relative to an external ionising radiotherapy beam, in particular relative to a positional reference, and the pose of the positioning tool (200) recorded which pose is used for the subsequent treatment.

Radiotherapy is delivered to the subject while the canal is held at one or more of the treatment poses. At one or more subsequent sessions, the treatment pose(s) may be (are) reproduced. The system allows bodily structures that can change their shape or position between sessions to be brought into a known, well defined position and stabilised during each session.

For instance, when the cervical canal is placed in the same spatial position in relation to the bony pelvis or to the radiotherapy machine isocenter during each radiotherapy session, the spontaneous movements of the cervix disappear totally and the volume to be irradiated around the cervix in order to take into account cervical spontaneous displacements, can become significantly smaller, and safety margins around the cervix may be reduced from 2 cm to 3-4 mm.

The system, positioning tool and method describe herein may be used to treat one or more tumours present in the bodily tissue.

Typically the ionising radiation head moves such that different ionising-radiation beam directions intersect during a treatment session, thereby minimising damage to surrounding tissue. A beam intersection volume is the volume in which different ionising-radiation beam directions intersect during an external radiotherapy treatment session. A simulated beam intersection volume is the volume in which different simulated ionising-radiation beam directions intersect during a simulation of an external radiotherapy treatment session. The (simulated) beam intersection volume usually coincides with the tissue target (e.g. tumour) in the subject.

Where the radiotherapy device (510) is provided with a ionising-radiation treatment head (518) that rotates around a single axis, the beam intersection volume is also known as an isocenter that is a centre of rotation of the ionising-radiation beam emitted by the ionising-radiation treatment head (518) during the external radiotherapy treatment session. The isocentre is well known in the art, see for example, http://ozradonc.wikidot.com/isocentre-of-the-linac. Devices having an isocentre (linac) are manufactured for instance by Varian. A simulated isocentre is centre of rotation the ionising-radiation beam emitted by the ionising-radiation treatment head (518) during a simulation of an external radiotherapy treatment session.

In other systems (e.g. Cyberknife), the radiotherapy device (510) is provided with a ionising-radiation treatment head (518) mounted on a robotic arm having three or more degrees of freedom of movement that offers directional control of the ionising-radiation beam around more than one axis. The beam intersection volume is the volume in which the different directions of the ionising-radiation beam emitted by the ionising-radiation treatment head (518) during an external radiotherapy treatment session intersect. The simulated beam intersection volume is the volume in which the different directions of the ionising-radiation beam emitted by the ionising-radiation treatment head (518) during a simulation of external radiotherapy treatment session intersect.

By external radiotherapy treatment programme, it is meant one or more sessions of radiotherapy treatment provided to a treatment site of the subject by an external radiotherapy source (e.g. through a linear accelerator optionally equipped with a multileaf collimator, or a tomotherapy system, or by any ionising radiation source moving around the patient such as in the Cyberknife system). The treatment may be composed of one or more sessions or fractions. Where there is a plurality of fractions, the overall dose is divided into a plurality of smaller doses delivered at a number of intervals over time (fractionation). Typically duration is 28-32 fractions for treatment of a cervical tumour, each fraction delivering a dose of up to 2.6 Gy to the tumour. By fractioning treatment, healthy cells surrounding the site of treatment are given time to recover. It is also possible to use the system to deliver the treatment in a few fractions as a boost, or as a palliative therapy in case of bleeding, with high doses per fraction, for instance, 5 fractions of 6 Gy, or 5 fractions of 4 Gy delivered to the tumor as a boost or 5 fractions of 7 Gy as a palliative therapy.

A radiotherapy programme typically comprises a simulation part and a treatment part. The simulation part involves acquiring internal medical images (e.g. by CT, MRI) of the subject usually in three-dimensions while the subject is accurately aligned on a moveable treatment simulation table in relation to an imaging device. These medical images are used to plan the subsequent external radiotherapy treatment. The radiologist determines from the images which tissues structures are to receive higher doses, lower doses, sensitive structures, the number of sessions or fractions, and the like. The treatment part as mentioned above exposes the subject to ionising radiation.

The elongated member (210) of the inserter (204) has a proximal (40) and distal (20) end. The elongated member (210) may be rigid (non-flexible). The elongated member (210) may be flexible which allows for better tolerance of the body towards the elongated member (210) which can remain in place in the canal up to 2-3 months during the course of fractionated treatment.

The elongated member (210) is dimensioned for insertion into the canal, in particular into the cervix and/or uterus and/or a vaginal vault recurrence. The elongated member (210) may have a length of 1 to 10 cm. Where the elongated member (210) is configured for positioning in the cervix and/or uterus, it may have a length of 1-8 cm and a maximum outer diameter of 3-8 mm. Where the elongated member (210) is configured for positioning in a vaginal vault recurrence it may have a length of 1-5 cm and a maximum outer diameter of 3-8 mm. The diameter of elongated member (210) may be uniform from proximal to distal end or may vary. For instance, the diameter may be larger towards the proximal part and smaller towards the distal part. The change in diameter may be gradual. The change in diameter may be gradual across the length of the elongated member (210). The small distal diameter is more atraumatic when entering the vagina, and a larger diameter towards the proximal part improves rigidity of the elongated member (210). See Tables 2 and 2a for preferred dimensions for various medical applications.

The effector shaft (310) may be configured to co-operate with the elongated member (210) such that movements of the steering guide are transferred to the elongated member (210).

The elongated member (210) is disposed with an elongated member lumen (214). The elongated member lumen (214) is open at the proximal end (40) to allow slidable insertion of the effector shaft (310) of the steering guide (300) prior to treatment. The elongated member lumen (214) may be open or closed at or towards the distal end (20). Where it is open, it can provide a drainage channel (270), or exit port (272), or threaded passage (272,-c) for a dismountable guiding strand (218). The steering guide (300) attached to the inserter (204) or elongated member (210) is rigidly attached. The rigid attachment minimises play or backlash between the inserter (204) and handle portion (316) of the steering guide (300).

The distal tip of the elongated member (210) may be atraumatic (e.g. have rounded edges, dome shaped, does not create an incision). The elongated member (210) may have a circular profile perpendicular to its longitudinal axis. The elongated member (210) may comprise an essentially cylindrical form. The elongated member (210) may be disposed with one or more fins. A fin is a protrusion that extends outwards from a surface of the elongated member (210). The fin extends also in a longitudinal direction. It functions to better affix the elongated member (210) to the inner walls of the canal (e.g. cervix), to prevent it from rotating during the manipulation with the steering guide. Preferably the one or more fins are provided within a proximal (40) half of the elongated member (210), for instance within the 2-4 cm of the proximal (40) end.

The elongated member (210) may be a rigid tube. The elongated member (210) may be a flexible tube. An advantage of a flexible tube is greater comfort to the subject while it is worn for the treatment duration (e.g. weeks). A wall of the elongated member (210) may be made from any biocompatible material such as a polymer. Examples of suitable substances include polycarbonate, PEEK, carbon fiber, polyamide, polyimide, polyurethane, or silicone. Examples of substances used to form a rigid elongated member (210) include polycarbonate, PEEK, carbon fiber, polyacrylamide resin reinforced with fibres (e.g. Ixef (Solvay)). Examples of substances used to form a flexible elongated member (210) include polyamide, polyimide, polyurethane, or silicone.

Usually the treatment is first simulated under a CT scan, or a PET CT scan, or under MRI. Later the treatment may involve acquisition of one or more X-rays in the treatment room. It is preferred that the elongated member (210) is made from a material compatible with medical imaging, such as with CT or MRI. The material may or may not be visible on a medical image. Examples of materials invisible in CT or CT/PET scan include polycarbonate, PEEK, carbon fiber, polyamide, polyimide, polyurethane, or silicone. For visibility under CT, PET/CT, the material may be mixed with a low percentage of barium sulfate. Examples of materials visible in MRI scan include polycarbonate, PEEK, carbon fiber, polyamide, polyimide, polyurethane, or silicone. The pose (position and/or orientation) of the elongated member (210) may be determined directly from the medical image of the elongated member (210) under MRI or opacified with barium sulfate (under CT or PET-CT). Examples of materials not visible in CT, CT/PET scan include polycarbonate, PEEK, carbon fiber, polyamide, polyimide, silicone, when not mixed with barium sulfate. Where it is not visible or not sufficiently visible to determine the position and/or orientation of the inserter, the elongated member (210) may be disposed with one or more imaging markers. This is of assistance when performing images using the imaging tools of the linear accelerator.

The inserter (204), in particular the elongated member (210), may be provided with one or more imaging markers (206) that can be identified by a medical image. In FIG. 1 a pair of imaging markers (206) is provided fixed to an outer surface of the elongated member (210). An imaging marker (206) can be identified by a medical image. An imaging marker (206) may be provided in fixed relation to the elongated member (210), for instance on an inner surface, outer surface or within a body of the elongated member (210). An imaging marker (206) may be a protrusion or an indentation. It may be made from the same material as the elongated member (210), and may be visible on a medical image because of a size difference. An imaging marker (206) may be made from a material different from elongated member (210) for instance a heavy metal such as platinum, platinum iridium, tantalum, tungsten, or a low density metal such as titanium, coated aluminium, etc.

The inserter (204), in particular the elongated member (210) may be provided with one or more (e.g. 2, 3 or more) position-determining radio transponders (260) whose positions can be determined and optionally tracked using a spatial transponder detector. The terms position-determining radio transponder and transponder are used interchangeably herein. A transponder is sometimes known as beacon transponder. In FIG. 1 three transponders (260, a, b, c) are provided fixed to an outer surface of the elongated member (210) at different positions.

A transponder (260) is a device that emits electromagnetic pulses at a certain frequency that is detectable by the spatial transponder detector—typically comprising a number of spatially separated receivers (coils). The timing of the pulse as detected by a number of spatially separated receivers in the positional transponder reader allow the location of the transponder to be accurately determined. The transponder (260) may receive power inductively. Where more than one transponder is present, each transponder may emit a signal at a different frequency. When at least three separately-identifiable transponders (260, a, b, c) are disposed on the inserter (204) at different positions, the orientation of the inserter (204) may also be determined. Examples of such systems are described, for example, in U.S. Pat. No. 9,248,003 B2, and U.S. Pat. No. 9,072,895. The use of transponders reduces the need to align the inserter (204) prior to radiation treatment using medical imaging, which reduces exposure to imaging radiation.

According to one aspect:
at least a part of the inserter (204) or one or more imaging markers borne by the inserter (204), is visible by medical imaging, in particular by X-ray medical imaging and/or by MR medical imaging,
and/or
at least a part of the elongated member (210) or one or more imaging markers borne by the inserter (204), is visible by medical imaging, in particular by X-ray medical imaging and/or by MR medical imaging,
and/or
the inserter (204) and/or elongated member (210) is disposed with one or more radio transponders borne by the inserter (204) for determining a position and/or orientation of the inserter (204) and/or elongated member (210) by a spatial transponder detector.

A guiding strand (218) is disposed at least partially within the elongated member lumen (214), and exits at a proximal end therefrom. The effector shaft (310) of the steering guide (300) comprises a guiding strand passage (312) that receives the guiding strand (218). The guiding strand passage (312) may be a lumen within the effector shaft (310) or a longitudinal groove on the surface of the effector shaft (310). The guiding strand (218) is restrained at or towards a distal end (20) of the guiding strand (218) to limit or prevent sliding of the guiding strand (218) in a proximal direction relative to the lumen (214). This allows tension to be applied to the guiding strand (218) in a proximal direction without release or displacement of the guiding strand (218). The effector shaft (310) guiding strand passage can be threaded through a proximal end of the guiding strand trailing outside the body and guided reliably into the elongated member lumen (214). The guiding strand allows repeatable mounting and dismounting of the steering guide prior to and after simulation and/or radiation treatments. Access to the elongated member lumen (214) is made available despite the elongated member lumen (214) being located in situ, for instance, in the cervix.

The guiding strand (218) may be a flexible cord (219) (e.g. made up of one more strands) or an inflation tube (236) or a flaccid tube to be stiffened by a stiffening stylet. The external diameter of the guiding strand (218) is smaller than the internal diameter of the effector shaft (310). It is dimensioned to be threaded through the guiding strand passage (312). The guiding strand (218) has a narrow cross-sectional profile, for instance, 0.1 to 2.5 mm (flexible cord), or 1 to 5 mm (inflation tube), or 1 to 5 mm (flaccid tube). It has tensile strength to resist tension placed thereon while the effector shaft (310) of the steering guide (300) is inserted into the elongated member lumen (214). It may be non-expandable in a longitudinal direction. Examples of a guiding strand (218) that is a flexible cord (219) is shown in FIGS. 1, 2A, 2B, 2C, and in FIG. 3 panels A, B, C, D, E, F, K, L, a, b, c, d, e, f, k, l, m.

The guiding strand (218) may be non-dismountably (e.g. permanently) attached to the inserter (204) or may be dismountably attached to the inserter (204). Where the guiding strand (218) is dismountably attached, preferably such guiding strand is a flexible cord (219).

A non-dismountable attachment to the inserter (204) may be achieved, for instance, during a moulded production of the elongated member (210), by a knotted attachment to a strut (213), by adhesive. A distal end of the guiding strand (218) is preferably attached in fixed relation to the elongated member lumen (214), preferably to a distal-most end of the elongated member lumen (214). Examples of a guiding strand (218) that is non-dismountably attached is shown in FIG. 2A, and in FIG. 3 panels A, B, C, D, G, H, I.

A dismountable attachment of the guiding strand (218, 219) to the inserter (204) allows both
a reliable guidance of the effector shaft (310) into the elongated member lumen (214) when the guiding strand (218, 219) is present;
an insertion of a brachytherapy applicator into the elongated member lumen (214) when the guiding strand (218, 219) is removed (dismounted).

There are situations when a treatment starts with an external radiotherapy programme, and subsequently a brachytherapy treatment is needed. Brachytherapy is well known in the art, and is a process of treatment of a target using an internal ionising radiation source. The radiation source is disposed in a sealed capsule at the end of a flexible cable spooled in an afterloader safe. When required, the cable, having a certain pushability, is fed out from the afterloader into a transfer tube connected to brachytherapy applicator at the treatment target. The radiation source is held in position by or within the brachytherapy applicator for a duration of the treatment, and subsequently withdrawn into the afterloader safe. The elongated member (210) in situ may be utilised as a catheter allowing the introduction of a brachytherapy applicator. Where elongated member (210) is already placed adjacent to the target, the guiding strand (218) is dismounted and removed and the applicator introduced into the elongated member lumen (214) and maintained therein in order to irradiate the target.

Where the guiding strand (218, 219) is dismountably attached to the inserter (204), it is typically a flexible cord (219).

According to one example, the dismountable guiding strand (218, 219) is a flexible cord (219) that has an anchoring end (219, b) provided with a stop anchor (219, c).

The elongated member lumen (214) may be provided at a distal (20) end with an exit port (272, -a, -b). The guiding strand (218, 219) is disposed through a proximal entrance (214, a) to the elongated member lumen (214), along the elongated member lumen (214) in a distal direction, through the distal exit port (272, -a, -b), and returns in a proximal direction to a proximal end of the inserter (204). The guiding strand (218, 219) has an anchoring end (219, b) and a free end (219, a). The anchoring end (219, b) exits from the exit port (272, -a, -b). The anchoring end (219, b) is provided with a stop anchor (219, c). The stop anchor (219, c) is configured to engage with a reciprocating stop (254) on the inserter (204) for instance on the elongated member (210) or on the stop member (250). The reciprocating stop (254) may be a passageway. The reciprocating stop (254) is disposed at the proximal end of the inserter (204) that is accessible by the specialist when the inserter (204) is in situ. The free end (219, a) exits from the proximal entrance (214, a) to the elongated member lumen (214). The free end (219, a) is able to pass unrestricted through the proximal entrance (214, a) to the elongated member lumen (214), exit port (272, -a, -b) and reciprocating stop (254).

Tension applied to the free end (219, a) of the guiding strand (218) engages the stop anchor (219, c) with the reciprocating stop (254), preventing sliding movement of the guiding strand (219) within the elongated member lumen (214). Tension applied to the anchoring end (219, b) of the guiding strand (218) causes sliding movement the guiding strand (218) within the elongated member lumen (214); the free end (219, a) passes through the proximal entrance to the elongated member lumen (214), exit port (270, -a, -b, -c) and reciprocating stop (254) and ultimately dismounts the guiding strand (218) from the inserter (204). Examples of a guiding strand (218) that is dismountable with a stop anchor (219, c) is shown in FIG. 2B, and in FIG. 3 panels E, F, d, e, f.

According to another example, the dismountable guiding strand (218, 219) is a flexible cord (219) that has a threaded (219, d) distal end. The elongated member lumen (214) may be provided at a distal (20) end with a reciprocating threaded passage (272,-c). Axial rotation of the flexible cord (219) in one direction allows the threaded (219, d) distal end of the guiding strand (218, 219) to engage with the reciprocating threaded passage (272,-c) of the inserter (204) thereby attaching the elongated member (210). Rotation in the other direction releases the flexible cord (219) from the elongated member (210). Examples of a guiding strand (218) with a threaded portion (219, d) that is dismountable is shown in FIG. 2D, 2E, and in FIG. 3 panel K.

According to another example, the dismountable guiding strand (218, 219) is a flexible cord (219) that is removeable by exertion of a pulling force above a certain threshold. The pulling force may in the range of 1 to 3 kg. In one example, the flexible cord (219) has a breakable portion (219, e) at the distal end where it attaches to the inserter (204), in particular to the elongated member (210). In another example, the flexible cord (219) is attached to the inserter (204) by coupling that pulls apart from the inserter (204). An example of a guiding strand (218) with a breakable portion (219, e) is shown in FIG. 3 panel L.

The guiding strand (218) that is a flexible cord (219) may be made from any suitable material, preferably non-ferromagnetic, such as nylon, or other polymeric material, or metal such as nitinol. The guiding strand (218) that is an inflation tube may be made from any suitable material, preferably non-ferromagnetic, such as polymer such as polyamide, or metal, such as nitinol. The guiding strand (218) that is a flaccid tube may be made from any suitable material, preferably non-ferromagnetic, such as polymer such as polyamide. The guiding strand (218) may be contain or be coated with an antibacterial agent; examples of antibacterial agent include silver particles, erythromycin, or other antibiotics. Preferably guiding strand (218) is made from a radio-transparent material. Preferably guiding strand (218) is made from a MRI compatible and biocompatible material. A distal end of the guiding strand is preferably attached in fixed relation to the elongated member lumen (214), preferably to a distal-most end of the elongated member lumen (214).

The guiding strand (218) may be an inflation tube (236) that is a tube having a lumen in fluid connection with a distal slide restrictor (220) that is an inflatable balloon assembly (230)—see later below. A lumen of the inflation tube (236) may allow passage of fluid (e.g. liquid, saline) for inflating one or more balloons of the inflatable balloon assembly (230). Examples of a guiding strand (218) that is an inflation tube (236) is shown in FIG. 3 panels G, H, J, h, i, j, FIGS. 4, 24 to 26. The elongated member (200) may be provided with a crimpable or self-expandable cylindrical body (e.g. a metal mesh) (240) around an outside of a distal end. This allows the practitioner open this metallic mesh inside the canal (for instance inside the uterus (604)) by inflating a balloon (balloon expandable mesh) or by removing a slide member around the mesh (self-expanding stent). The inflatable balloon assembly (230) allows blocking movement of the elongated member inside the uterus. Stitches used to attach the inserter to the entrance to the cervix may become loose over time, when tumors shrink. The presence of distal slide restrictor (220) that is an inflatable balloon assembly (230) prevents the elongated member (210) slipping downwards out from the uterus (604).

The guiding strand (218) may be a flaccid tube (237) that is a tube having a lumen (238) configured to receive a stiffening stylet. The flaccid tube (237) is more flexible in the absence of the stiffening stylet, and is less flexible (more stiff, having more pushability) when the stiffening stylet in inserted in the lumen (238). Examples of a guiding strand (218) that is a flaccid tube (237) is shown in FIG. 3 panels M, N, O, P, n, o, p, xvi to xx]. The stiffening stylet is more flexible than the flaccid tube (237). The stiffening stylet may be a metallic or polymeric wire. While the inserter (204) is worn by the subject, the stiffening stylet is absent from the flaccid tube lumen (238). The flaccid tube (237) without stiffening stylet allows for a more comfortable wearing of the inserter as the flaccid tube (237) has increased flexibility, and is more conforming to the changes in shape of the subject during wearing. Prior to insertion of the steering guide, the stiffening stylet is inserter along the flaccid tube (237) lumen (238); this increases the stiffness, and allows the guiding strand passage (312) of the effector shaft (310) of the steering guide (300) to be pushed along the stiffened flaccid tube (237) with a reduction in buckling, and hence provides a faster and less uncomfortable experience for the subject. After the external radiotherapy treatment and/or a simulation of treatment at a certain pose of the inserter (204), the steering guide (300) is removed.

The stiffening stylet may be removed after steering guide (300) has been inserter, or may be removed after the steering guide (300) has been removed.

Where the inserter (204) is for the cervix (602), the guiding strand (218) is long enough to exit through the vagina (606). A trailing end of the guiding strand (218) may be fixed with an adhesive pad to the skin, for instance in the groin area of the subject between simulation and radiotherapy treatment and/or between radiotherapy treatment fractions.

The inserter (204) may comprise one or more slide restrictors (220). The elongated member (210) may be provided with one or more slide restrictors (220) configured to reduced or prevent sliding of the elongated member (210) relative to the canal as shown, for instance in FIGS. 1, 2A, 2B, 3, 5 and 23 to 26. The slide restrictor (220) may engage with a wall of the canal by friction, for instance, or abut with an entrance or exit to the canal. The slide restrictor (220) may be attached in fixed relation to the elongated member (210). The slide restrictor (220) may be disposed at a discrete longitudinal position on the elongated member (210). Examples of a slide restrictor include an inflatable balloon assembly (230), an expandable stent (240), and a stop member (250).

There may be two slide restrictors (220) each disposed at a different longitudinal position on the elongated member (210). One slide restrictor (220) may be disposed at the proximal end (40) of the elongated member (210) the other may be disposed at the distal end (20) of the elongated member (210). One slide restrictor (220) may be a stop member (250), the other slide restrictor may be an inflatable balloon assembly (230) or an expandable stent (240). Such arrangement allows the two slide restrictors (220) to flank tissue disposed between an entrance and exit of the canal effective clamp the elongated member (210) thereagainst. Two slide restrictors (220) are disposed at either end of the elongated member (210) in FIG. 3 (see combination of Tables 1a to e), 24 to 26. Preferably one of the two slide restrictors (220) is a proximal stop member (250). The arrangement of two slide restrictors (220) may contribute to increase the accuracy of uterus positioning, by reducing elongated member (210) freedom inside the uterine canal (604). In addition, it solves a problem observed when the proximal stop member (250) is sutured to the cervix; after a number of fractions, the cervical tumour begins to shrink and the sutures can become looser, allowing dislodgment of the elongated member; this may become important when the effector shaft (310) is withdrawn after a fraction. By inflating a distally placed the balloon assembly (230) or expandable stent (240), the elongated member (210) becomes fixed inside uterine canal (604) and resistant to tension applied for instance during withdrawal of the effector shaft (310).

A slide restrictor (220) may be an inflatable balloon assembly (230). The inflatable balloon assembly (230) may comprise one or more (e.g. 2, 3, 4) inflatable balloons (231,-a to -h) provided around at least a distal part (20) of the elongated member (210), as exemplified in FIG. 3 (panels i, ii, iii, vi, vii, viii, xi, xii, xiii, xvi, xvii, xviii, G, H, J), 24, 25 and 26. Two inflatable balloons (231,-a, 231,-b) may be provided at the distal end of the elongated member (210), optionally arranged diametrically (e.g. FIG. 3 (panel i, vi, xi, xvii, G), 24, 25 and 26). One inflatable balloon may be provided at the distal end of the elongated member (210), optionally having an annular form e.g. conical (FIG. 3, panel ii, vii, xii, xvii, 231,-c) or barrel (FIG. 3, panel iii, viii, xiii, xviii, 231,-d; FIG. 3, panel 1231,-h). A wall of the inflatable balloon (231,-a to -h) may be made from any suitable expandable or non-expandable material. Examples of expandable materials include polyurethane, any elastic polymer, thin film polymers (nylon, compliant polyamide or others) or other elastomers. The inflatable balloon (231,-a to -h) may have a limited maximum inflation size, whereby inflation at or above the maximum inflation size is resisted. Limited maximum inflation size may be achieved by forming the balloon wall from a non-expandable material such as PET, semi-compliant or non-compliant polyamide.

In fluid connection with an inflatable balloon (231,-a to -h) may be an inflation lumen (234). The inflation lumen (234) may extend via an inflation tube (236) such as a catheter or flexible tubing in a proximal (40) direction. The inflation lumen (234) may be formed within the guiding strand (218) as explained earlier; accordingly the guiding strand (218) may be an inflation tube (236) as shown, for instance, in FIG. 3 panels G, H, I. The inflation tube (236) may alternatively be provided outside the elongated member (210) as shown, for instance, in FIG. 3 panels i, ii, iii, vi, vii, viii, xi, xii, xiii. The inflation tube (236) may extend in a proximal direction outside the elongated member (210).

The inflation lumen (234) allows inflation of the inflatable balloon lumen (232) from outside the bodily canal after the elongated member (210) has been positioned. The inflatable balloon (231, -a to -h) may be deflated after treatment by release of inflation fluid (e.g. saline or sterile water) from the balloon lumen (232) via the inflation lumen (234). The inflation fluid may contain contrast agent. FIGS. 24 to 26 exemplify the positioning tool (200) provided with an inflatable balloon assembly (230) wherein the inflatable balloons (231-e, 231-f, 231-h) are located in the uterine canal (604), and inflated to prevent or reduce sliding movement of the elongated member (210). Also shown is an inflation tube (236) for controllable inflation and deflation of the balloon (231-e, 231-f, 231-h). The inflation tube (236) is the guiding strand (218), as described previously.

The inflatable balloon (231, -a to -h) may be used to prevent the elongated member being ejected from the uterine canal during the effector shaft retrieval and to improve the positioning of the uterus. In this case, once the effector shaft (310) of the steering guide (300) has been introduced inside the elongated member (210), the balloon (231-a to -h) may be inflated. This may contribute to increase the accuracy of uterus positioning, by reducing elongated member (210) freedom inside the uterine canal (604). In addition, once the cervical tumour begins to shrink, the stitches fixing the elongated member (210) on the cervix can become looser and allow possible elongated member dislodgment. By inflating the balloon, the elongated member will be automatically fixed inside uterine canal. The balloon (231-a to -h) may be inflated permanently, during the treatment duration (e.g. 1 to 8 weeks), in order to prevent elongated member (210) from dislodgment from uterine canal (604), even between fractions.

A slide restrictor (220) may be an expandable stent (240). The expandable stent (240) may be provided around at least a distal part of the elongated member (210), as exemplified in FIG. 3 panels v, x, xv, xx. It may be made from any suitable expandable material such as CoCr alloy, phynox, nitinol, a biodegradable metal such as magnesium alloy, zinc alloy, iron, biodegradable polymer. The expandable stent may be self-expanding or balloon expandable. The stent may be contracted after treatment by covering with a slidable sheath that restricts the outer profile. Expandable stents are well known in the art and typically have a tubular form, the walls having a mesh construction, cut from a tube or made from braided wire, that expand radially.

The stop member (250) may be provided at the proximal end of the elongated member (210), as exemplified in FIG. 3 panels a, b, d, e, g, h, k, l, n, o. The stop member acts as a distance limiter to prevent sliding of the elongated member (210) further into the canal as it abuts with the canal entrance. The stop member is disposed at the proximal end of the elongated member (210). The stop member protrudes from the outer surface of the elongated member (210). The stop member (250) is provided in fixed (non-moving) relation to the elongated member (210). The stop member (250) may be rigid. The stop member may comprise an annular structure. It may be formed from the same material as the member (210) or it may be formed from a different material. The stop member (250) may be provided with one or more suture channels (252). The suture channels allow the stop member to be sutured to the entrance to the canal e.g. to the banks of the cervix. FIGS. 5 and 23 to 25, 26 exemplify the inserter (204) provided with a stop member (250) at the proximal end of the elongated member (210). The positioning tool (200) is located in the cervix (602) or in the cervix (602) and uterine canal (604), and abutting of the stop member against the bank of the cervix (602) prevents or reduces sliding movement of the elongated member (210).

A slide restrictor (220) may be a region at a distal part of the elongated member (210) containing one or more distal protrusions. The protrusion may be a lateral protrusion (245), as exemplified in FIG. 3 panels iv, ix, xiv, xix. The protrusion may be an annular ring or segment. The distal protrusion (245) acts as a restrictor to prevent or reduce sliding of the elongated member (210) further into the canal as it abuts with the canal wall. The distal protrusion (245) is disposed at the distal end of the elongated member (210). The distal protrusion (245) protrudes from the outer surface of the elongated member (210). The distal protrusion (245) is provided in fixed (non-moving) relation to the elongated member (210). The distal protrusion (245) may be rigid. The distal protrusion (245) may comprise an annular structure. It may be formed from the same material as the member (210) or it may be formed from a different material.

The elongated member (210) may be provided with one or more drainage channels (270, -a, -b, -c) at the distal end (20) as shown for instance in FIG. 3 panels B, C, D, E, F, K, N, O, P. The drainage channel fluidly connects the elongated member lumen (214) with an exterior surface of the elongated member (210). A drainage channel (270, -a, -b) may be provided towards the distal end of the elongated member (210). The distal terminal end of the elongated member (210) may be open to the elongated member lumen (214), thereby forming a drainage channel (270, -b); the guiding strand (218) may be attached to a strut (213) attached to the elongated member lumen (214) that does not occlude the passage of fluid (e.g. FIG. 3 panel C, O). A drainage channel (270, -c) may be provided on a side wall of elongated member lumen (214). The drainage channel(s) (270) allow drainage of fluids that may arise inside the uterine canal to be safely removed. The fluids exit the proximal end of the elongated member lumen (214) e.g. into the vaginal passage (606) before or after simulation and/or radiotherapy treatment, when effector shaft is not inside the elongated member. A drainage channel allows draining of liquid from the canal, significantly reducing a risk of infection. A drainage channel may also function as an exit port for the guiding strand (218) and vice versa. A drainage channel may also function as threaded passage (272,-c) for a dismountable guiding strand (218) and vice versa. A drainage channel may also function as threaded passage (272,-c) for a dismountable guiding strand (218) and vice versa.

The inserter may be provided with any one of a number of different arrangements of drainage channels (270), side restrictors (220), exit ports (272), threaded passage (272,-c), and guiding strand (218). For instance, a distal slide restrictor, a proximal slide restrictor, an exit port, and one or more drainage channels may be provided or absent. Where both drainage channel and distal slide restrictor (i to v) are present, the drainage channels may flank one of both ends of the distal slide restrictor. In FIG. 3, any one the elongated members (A, B, C, D) may be combined with a proximal slide restrictor (a, b) or may not be combined with a proximal slide restrictor (c); the elongated members (A, B, C, D) may or may not contain a distal slide restrictor (i, ii, iii, iv, v). Further, in FIG. 3, any one the elongated members (E, F) may be combined with a proximal slide restrictor (d, e) or may not be combined with a proximal slide restrictor (f); the elongated members (E, F) may or may not contain a distal slide restrictor (vi, vii, viii, xiv, x); the guiding strand is detachable.

Further, in FIG. 3, any one the elongated members with distal slide restrictors (G, H, J) may be combined with a proximal slide restrictor (g, h), or may not be combined with a proximal slide restrictor (j); the guiding strand is an inflation tube.

Further, in FIG. 3, any one the elongated members (K, L) may be combined with a proximal slide restrictor (k, l) or may not be combined with a proximal slide restrictor (m); the elongated members (K, L) may or may not contain a distal slide restrictor (xi, xii, xiii, xiv, xv); the guiding strand is detachable.

Further, in FIG. 3, any one the elongated members (M, N, O, P) may be combined with a proximal slide restrictor (n, o) or may not be combined with a proximal slide restrictor (p); the elongated members (M, N, O, P) may or may not contain a distal slide restrictor (xvi, xvii, xviii, xiv, xv); the guiding strand is a flaccid tube. Where both a distal slide restrictor (i to xx) and drainage channels or exit ports are present, the distal slide restrictor (i to xx) may be disposed within a region (e.g. 211) of the elongated member (210) that does not block the drainage channels.

Examples of different combinations is provided in Tables 1a to 1e below. Exemplary elements referred to in Tables 1a to 1e are depicted in FIG. 3.

TABLE 1a exemplary combinations of an inserter (204) features when the guiding strand (218) is a flexible cord (219).

| (+) proximal slide restrictor, (+) suture channels (+) GS | | | | (+) proximal slide restrictor, (−) suture channels (+) GS | | | | (−) proximal slide Restrictor (+) GS | | | |
|---|---|---|---|---|---|---|---|---|---|---|---|
| Aa | Ba | Ca | Da | Ab | Bb | Cb | Db | Ac | Bc | Cc | Dc |
| Aa-i | Ba-i | Ca-i | Da-i | Ab-i | Bb-i | Cb-i | Db-i | Ac-i | Bc-i | Cc-i | Dc-i |
| Aa-ii | Ba-ii | Ca-ii | Da-ii | Ab-ii | Bb-ii | Cb-ii | Db-ii | Ac-ii | Bc-ii | Cc-ii | Dc-ii |
| Aa-iii | Ba-iii | Ca-iii | Da-iii | Ab-iii | Bb-iii | Cb-iii | Db-iii | Ac-iii | Bc-iii | Cc-iii | Dc-iii |
| Aa-iv | Ba-iv | Ca-iv | Da-iv | Ab-iv | Bb-iv | Cb-iv | Db-iv | Ac-iv | Bc-iv | Cc-iv | Dc-iv |
| Aa-v | Ba-v | Ca-v | Da-v | Ab-v | Bb-v | Cb-v | Db-v | Ac-v | Bc-v | Cc-v | Dc-v |

Key: A—Elongated member, no drainage channels, B—Elongated member drainage channels at distal end, C—Elongated member open at distal end, D—Elongated member drainage channels at distal end at side wall; a—proximal stop member (slide restrictor) with suture channels, b—proximal stop member (slide restrictor) without suture channels, c—no proximal stop member (slide restrictor); i—distal pair of balloons (slide restrictor), ii—distal conical balloon (slide restrictor), iii—distal barrel balloon (slide restrictor), iv—distal protrusion (slide restrictor), v—expandable stent (slide restrictor), GS guiding strand. FIG. 3 shows exemplary implementations of each feature (A, B, C, D, a, b, c, i, ii, iii, iv, v).

TABLE 1b exemplary combinations of inserter features when the guiding strand is dismountable.

| (+) proximal slide restrictor (+) reciprocating stop (+) suture channels (+) GS | | (+) proximal slide restrictor (+) reciprocating stop (−) suture channels (+) GS | | (−) proximal slide restrictor (+) reciprocating stop (+) GS | |
|---|---|---|---|---|---|
| Ed | Fd | Ee | Fe | Ef | Ff |
| Ed-vi | Fd-vi | Ee-vi | Fe-vi | Ef-vi | Ff-vi |
| Ed-vii | Fd-vii | Ee-vii | Fe-vii | Ef-vii | Ff-vii |
| Ed-viii | Fd-viii | Ee-viii | Fe-viii | Ef-viii | Ff-viii |
| Ed-ix | Fd-ix | Ee-ix | Fe-ix | Ef-ix | Ff-ix |
| Ed-x | Fd-x | Ee-x | Fe-x | Ef-x | Ff-x |

Key: E—Elongated member with exit port as passage, F—Elongated member with exit port open at distal end; d—proximal stop member (slide restrictor) with suture channels and reciprocating stop, e—proximal stop member (slide restrictor) without suture channels and with reciprocating stop, f—no proximal stop member (slide restrictor) and elongated member with reciprocating stop; vi—distal pair of balloons (slide restrictor), vii—distal conical balloon (slide restrictor), viii—distal barrel balloon (slide restrictor), ix—distal protrusion (slide restrictor), x—expandable stent (slide restrictor), GS guiding strand. FIG. 3 shows exemplary implementations of each feature (E, F, d, e, f, vi, vii, viii, ix, x).

TABLE 1c exemplary combinations of an inserter (204) features when the guiding strand (218) is a inflation tube (236).

| (+) proximal slide restrictor, (+) suture channels (+) GS inflation tube | (+) proximal slide restrictor, (−) suture channels (+) GS inflation tube | (−) proximal slide restrictor, (+) GS inflation tube |
|---|---|---|
| Gg | Gh | Gj |
| Hg | Hh | Hj |
| Jg | Jh | Jj |

Key: G—Elongated member with distal pair of balloons (slide restrictor), H—Elongated member with distal conical balloon (slide restrictor), J—Elongated member with distal barrel balloon (slide restrictor); g—proximal stop member (slide restrictor) with suture channels, h—proximal stop member (slide restrictor) without suture channels, j—no proximal stop member (slide restrictor). FIG. 3 shows exemplary implementations of each feature (G, H, J, g, h, j).

TABLE 1d exemplary combinations of inserter features when the guiding strand is dismountable.

| (+) proximal slide restrictor, (+) suture channels (+) GS detachable: threaded (K) or pullable (L) | | (+) proximal slide restrictor, (−) suture channels (+) GS detachable: threaded (K) or pullable (L) | | (−) proximal slide restrictor (+) GS detachable: threaded (K) or pullable (L) | |
|---|---|---|---|---|---|
| Kk | Lk | Kl | Ll | Km | Lm |
| Kk-xi | Lk-xi | Kl-xi | Ll-xi | Km-xi | Lm-xi |
| Kk-xii | Lk-xii | Kl-xii | Ll-xii | Km-xii | Lm-xii |
| Kk-xiii | Lk-xiii | Kl-xiii | Ll-xiii | Km-xiii | Lm-xiii |
| Kk-xiv | Lk-xiv | Kl-xiv | Ll-xiv | Km-xiv | Lm-xiv |
| Kk-xv | Lk-xv | Kl-xv | Ll-xv | Km-xv | Lm-xv |

Key: K—Elongated member with threaded passage (272,-c), L—Guiding strand attached to elongated member with breakable connection; k—proximal stop member (slide restrictor) with suture channels, l—proximal stop member (slide restrictor) without suture channels, m—no proximal stop member (slide restrictor); xi—distal pair of balloons (slide restrictor), xii—distal conical balloon (slide restrictor), xiii—distal barrel balloon (slide restrictor), xiv—distal protrusion (slide restrictor), xv—expandable stent (slide restrictor), GS guiding strand. FIG. 3 shows exemplary implementations of each feature (K, L, k, l, m, xi, xii, xiii, xiv, xv).

TABLE 1e exemplary combinations of an inserter (204) features when the guiding strand (218) is a flaccid tube (237).

| (+) proximal slide restrictor, (+) suture channels (+) GS flaccid tube | | | | (+) proximal slide restrictor, (−) suture channels (+) GS flaccid tube | | | | (−) proximal slide restrictor, (+) GS flaccid tube | | | |
|---|---|---|---|---|---|---|---|---|---|---|---|
| Mn | Nn | On | Pn | Mo | No | Oo | Po | Mp | Np | Op | Pp |
| Mn-xvi | Nn-xvi | On-xvi | Pn-xvi | Mo-xvi | No-xvi | Oo-xvi | Po-xvi | Mp-xvi | Np-xvi | Op-xvi | Pp-xvi |
| Mn-xvii | Nn-xvii | On-xvii | Pn-xvii | Mo-xvii | No-xvii | Oo-xvii | Po-xvii | Mp-xvii | Np-xvii | Op-xvii | Pp-xvii |
| Mn-xvii | Nn-xviii | On-xvii | Pn-xviii | Mo-xviii | No-xviii | Oo-xviii | Po-xviii | Mp-xviii | Np-xviii | Op-xvii | Pp-xviii |
| Mn-xix | Nn-xix | On-xix | Pn-xix | Mo-xix | No-xix | Oo-xix | Po-xix | Mp-xix | Np-xix | Op-xix | Pp-xix |
| Mn-xx | Nn-xx | On-xx | Pn-xx | Mo-xx | No-xx | Oo-xx | Po-xx | Mp-xx | Np-xx | Op-xx | Pp-xx |

Key: M—Elongated member, no drainage channels, N—Elongated member drainage channels at distal end, O—Elongated member open at distal end, P—Elongated member drainage channels at distal end at side wall; n—proximal stop member (slide restrictor) with suture channels, o—proximal stop member (slide restrictor) without suture channels, p—no proximal stop member (slide restrictor); xvi—distal pair of balloons (slide restrictor), xvii—distal conical balloon (slide restrictor), xviii—distal barrel balloon (slide restrictor), xix—distal protrusion (slide restrictor), xx—expandable stent (slide restrictor). FIG. 3 shows exemplary implementations of each feature (M, N, O, P, n, o, p, xvi, xvii, xviii, xix, xx).

The positioning tool (200) may further comprise a removable steering guide (300) as shown for instance in FIGS. 5 to 21 and 26 for steering the position and/or orientation of the inserter (204). The steering guide (300) has a proximal (40) and distal (20) end. The steering guide (300) may be dismountably attached to the inserter (204) or elongated member (210). The steering guide (300) may be provided with a guiding strand passage (312) for slidable movement thereof along the guiding strand (218). The guiding strand passage (312) may be provided at least partially along a length of the steering guide (300), for instance, along the effector shaft (310) and/or transmission (314) as described later below.

An effector shaft (310), disposed at the distal end (20) of the steering guide is configured for insertion into the elongated member lumen (214) along the guiding strand (218). The effector shaft (310) is configured for (repeatable) slidable and removable insertion into the elongated member lumen (214). The effector shaft (310) may have a circular cross-sectional outer profile perpendicular to its longitudinal axis. The outer profile may have the same size in an axial direction. The outer profile may be tapered in an axial direction; the small profile may be at the distal end.

The effector shaft (310) may be disposed with one or more indentations on the surface that co-operate with complementary protrusions in the inner surface of the elongated member lumen (214). The arrangement allows the effector shaft (310) to latch within the elongated member lumen (214). The effector shaft (310) may click into position in the inserter (204). Removal of the effector shaft (310) is by pulling to overcome the force of the latch.

The effector shaft (310) is preferably rigid. It is preferably non-flexible. It may be substantially formed of a rigid rod. It may have a straight form for instance for use with the cervix and/or uterus. It may have a curved form.

The effector shaft (310) may be made from biocompatible, radio-visible material such as titanium, coated aluminium. It is preferably made from a low density material to avoid artifacts under CT or PET/CT. The effector shaft (310) may be made from an MRI compatible material such as titanium, coated aluminium, It may be made from a biocompatible, high density material such as tantalum. However, tantalum will provoke more artefacts under CT and PET/CT. In order to reduce artefacts under CT, PET/CT, one may combine a radio invisible inserter (204), and an effector shaft which is radio-visible, made from a low density metal, such as from titanium or coated aluminium.

The effector shaft (310) may be provided with the guiding strand passage (312) for slidable movement thereof along the guiding strand (218). The guiding strand passage (312) may be a lumen within the effector shaft (310) or a longitudinal groove (e.g. FIG. 10, and detail FIG. 10A) on the surface of the effector shaft (310). The guiding strand passage (312) may be provided at least partially along a longitudinal length of the effector shaft (310). An entrance (312, -a) to the guiding strand passage is disposed at the distal end of the effector shaft (310), preferably at the distal tip. An exit (312, -b1 to -b5) from the guiding strand passage is disposed proximal to (i.e. at a proximal side of) the entrance (312, -a). FIG. 6 shows different possible positions for the guiding strand passage (312) entrance (312, -a) and exit (312, -b) where the guiding strand passage is a lumen. An exit (312,-b1) to the guiding strand passage (312) may be disposed at a distal end of the effector shaft (310). An exit (312,-b2) to the guiding strand passage (312) may be disposed at a proximal end of the effector shaft (310). An exit (312,-b3) to the guiding strand passage (312) may be disposed at a distal end of the transmission (314). An exit (312,-b4) to the guiding strand passage (312) may be disposed in a mid-portion of the transmission (314). An exit (312,-b5) to the guiding strand passage (312) may be disposed at a proximal end of the transmission (314).

In FIG. 7, the guiding strand passage (312) entrance (312, -a) is at the effector shaft (310) distal tip, and exit (312, -b3) provided towards a distal end of the transmission (314). In FIG. 8 the exit (312, -b5) is provided where the proximal end of the transmission (314) joins with a distal end of the handle portion (316). In FIG. 9, the guiding strand passage (312) entrance (312, -a) is at the effector shaft (310) distal tip, and exit (312, -b2) provided towards a proximal end of the effector shaft (310). The further the distance of the exit (b) from the entrance (a), the longer the guiding strand (218). In FIGS. 15, 17 and 18, the guiding strand passage (312) entrance (312, -a) is at the effector shaft (310) distal tip, and an exit (312, -b4) is provided towards on a mid-section the transmission (314).

The effector shaft (310) may be made from any suitable biocompatible material such as medical grade non-ferromagnetic stainless steel, tantalum, titanium, polycarbonate, PEEK, carbon fibre, fibreglass, polyarylamide resin reinforced with fibers (e.g. Ixef (Solvay)), aluminium (coated).

Usually the treatment is first simulated under a CT scan, or a PET CT scan, or under MRI. Later the treatment may involve acquisition of one or more X-rays in the treatment room. It is preferred that the effector shaft (310) is made from a material compatible with medical imaging, such as with CT or MRI or X-ray. The material may or may not be visible on a medical image.

Where the effector shaft (310) is visible on a medical image, the pose of the effector shaft (310) may be determined directly from the medical image of the effector shaft (310). When the treatment is simulated under MRI, the effector shaft (310) may be manufactured from a low density material, such as PEEK or polycarbonate, polyarylamide resin reinforced with fibers (e.g. Ixef (Solvay)) or from a MR compatible (non-magnetic) material, such as aluminium coated with a layer of biocompatible metal (titanium) or from titanium. For the CT scan simulation, coated aluminium or titanium, PEEK, polycarbonate or polyarylamide resin reinforced with fibers (e.g. Ixef (Solvay)) (mixed with barium sulfate) would also be an advantage, because it allows for less artefacts compared with using a high density metal such as stainless steel. It is an aspect that a coated aluminium, PEEK, polycarbonate, polyarylamide resin reinforced with fibers (e.g. Ixef (Solvay)) steering guide (300) (mixed with barium sulfate) is used for simulation and the stainless steel for the treatment. It is as aspect that an aluminium steering guide (300) or PEEK, polycarbonate or polyarylamide resin reinforced with fibers (e.g. Ixef (Solvay)) (mixed or not with barium sulfate) is used for simulation and for treatment. Most modern imaging devices that are combined with radiotherapy treatment devices allow a good visibility of any metal structure or radio-visible polymer such as the effector shaft (310). In this case, the effector shaft may be visible by itself and could not necessarily need the presence of imaging markers to be seen by the imaging device.

Where the effector shaft (310) is not visible or not sufficiently visible to determine the position and/or orientation of the inserter, the effector shaft (310) may be disposed with one or more imaging markers (350, a, b). This is of assistance when performing images using the imaging tools of the linear accelerator. The steering guide (300), in particular the effector shaft (310) may be provided with one or more imaging markers that can be identified by a medical image. An imaging marker may be provided in fixed relation to the effector shaft (310), for instance on an inner surface, outer surface, or within a body of the effector shaft (310). An imaging marker may be made from a material different from the effector shaft (310) for instance a heavy metal such as platinum, platinum iridium, tantalum, tungsten, etc.

The effector shaft (310) may have a length (E) of 1-10 cm, preferably of 4-10 cm for cervical/uterus insertion. The maximum outer diameter may be 0.3-0.7 cm. The diameter of effector shaft (310) may be uniform from proximal to distal end or may vary. For instance, the diameter may be larger towards the proximal part and smaller towards the distal part. The change in diameter may be gradual. The change in diameter may be gradual across the length of the effector shaft (310). The effector shaft may adopt and angle alpha with respect to the transmission (e.g. FIG. 6). The angle alpha is measured in a plane formed between the transmission and effector. The angle alpha is less than 180 deg when the handle and effector shaft are on the same side (cis) of the transmission; the angle alpha is greater than 180 deg when the handle and effector shaft are on opposite sides of the transmission (trans). The angle alpha is 180 deg when the handle and effector shaft mutually coaxial or linear. See Table 2 and 2a for preferred dimensions, angles for various medical applications.

A handle portion (316), disposed at the proximal end (40) of the steering guide (300) is provided in fixed relation (position and orientation) to the effector shaft (310). Accordingly directional and/or positional movements of the handle portion (316) cause corresponding directional and/or positional movements of the effector shaft (310). The handle portion (316) is preferably rigid. It is preferably non-flexible. It may be substantially formed of a rigid rod.

The handle portion (316) may have a length (H) of 2-50 cm, preferably of 15 to 25 cm for cervix/uterus application. In very obese subjects, the handle portion (316) may have a length of up to 40 or 50 cm. The diameter may be 0.3-3 cm, preferably of 0.5-2 cm.

The handle portion may adopt an angle beta with respect to the transmission (e.g. FIG. 6). The angle beta is measured in a plane formed between the transmission and handle portion. The angle beta is less than 180 deg when the handle and effector shaft are on the same side (cis) of the transmission; the angle beta is greater than 180 deg when the handle and effector shaft are on opposite sides of the transmission (trans). See Tables 2 and 2a for preferred dimensions, angles for various medical applications.

The handle portion (316) may be made from any suitable biocompatible material such as medical grade non-ferromagnetic stainless steel, tantalum, titanium, polycarbonate, PEEK, carbon fibre, fibreglass, polyarylamide resin reinforced with fibers (e.g. Ixef (Solvay)), polyphenylsulfone (PPSU), aluminium (coated), bioceramics such as aluminosilicates, styrene acrylonitrile, bioceramic-polymer materials. The handle portion (316) may be made from the same material as the transmission (314). The handle portion (316) may have the same diameter as the proximal (40) end of the transmission (314).

The handle portion (316) may be formed from an imaging-transparent material such as a polymeric rod or tube. The same material may be used to form the transmission (314), for ease of manufacture; this can reduce imaging artefacts caused by the transmission (314) in the vaginal regional (606)—this is described in more detail below. Examples of suitable polymers include polycarbonate. Other materials that may be used for the handle portion are fiberglass, carbon fiber, polyarylamide resin reinforced with fibers (e.g. Ixef (Solvay)), polyphenylsulfone (PPSU), bioceramics such as aluminosilicates, styrene acrylonitrile, bioceramic-polymer materials, etc. FIGS. 7, 8 and 15 to 18 depict examples of a steering guide (300) formed from a polymeric handle portion (316) and transmission (314) and both having a larger diameter (e.g. 0.8-2.5 cm) compared with the effector shaft (310) which may be formed from a rigid metal such as titanium or a hard polymer (polycarbonate, PEEK, polyarylamide resin reinforced with fibers).

The steering guide (300), in particular the handle portion (316) and/or transmission (314) may be provided with one or more (e.g. 2, 3 or more) radiofrequency identification (RFID) tags. The RFID tag allows identification of the steering guide (300). The system may be provided with an RFID tag reading unit comprising an RFID tag reader and processor or interface to a processor configured to prevent operation of the robotic arm when the RFID tag does not match an expected RFID tag stored in the system. As a radiation oncology department may have a plurality of steering guides of different sizes (see e.g. Table 2 herein) for use with different subjects, the provision of an RFID tag prevents a subject from being provided with the incorrect steering guide (300). The RFID tag may be disposed within a body of the steering guide (300). In particular, it may be provided within a slot provided in the strengthening strut (317) (see e.g. FIGS. 15, 16, 17, 19 to 21). For instance, it may be placed within a slot provided in the lateral side of the handle (316). The RFID tag may be rewritable or non-rewritable. The non-writable RFID chip allows the steering guide to be attributed only to one single patient with a reduction in work-flow errors. A system would not allow a steering guide RFID chip to be rewritten and be used in another patient.

The handle portion (316) may be configured for attachment to a positioning device; the attachment is preferably dismountable. The positioning device is configured to adjust and fix the position and/or orientation of the handle portion (316) and hence of the effector shaft (310). A positioning device typically has an end effector fitting (e.g. a set of jaws, chuck) for dismountable attachment to the handle portion. It has a base that is fixed e.g. to the floor, the ceiling or simulation or treatment table. Preferably, the base of the positioning device is fixed or fixable to the simulation or treatment table between the legs of the subject. The end effector has a number of degrees of freedom of movement (e.g. 3, 4, 5, 6, 7, 8), and the position and/or orientation of the end effector. The positioning device may comprise a number of links connected in a kinematic chain by revolute joints also known as axes. It has a number of axes (e.g. 3, 4, 5, 6, 7, 8) to allow the end effector to adopt a large variety of controllable positions and orientations.

The joints of the positioning device may be passive (non-motorised). In a passive system, the joints may be manually adjustable, releasable and lockable. Once the pose (position and/or orientation) of the end effector has been manually, the joints are locked and the pose of the end effector fitting is fixed.

The joints of the positioning device may be motorised. The positioning device may be a robotic arm (RA). In a robotic arm, the joint positions and hence pose (position and/or orientation) of the end effector fitting are controllable by electronic signals. The robotic arm may have a "zero gravity mode", in which the weight of the arm is supported by the motorised joints, but the pose (position and/or orientation) of the end effector can be manually set and then locked. Hence a robotic arm can operate in under manual or electronic control.

The RA may have a switchable zero gravity mode. In zero-gravity-on (weightless) mode, the joints of the robotic arm may or may not be supported (e.g. by the servos) to prevent collapse of the arm. The pose of the RA fitting may be guided manually e.g. by the medical staff. This allows ease of connection between the positioning tool (200) and the RA fitting when the positioning tool (200) has already been inserted into the subject. It also allows a manual fine-tuning of the pose of the steering guide (300) for simulation and treatment. Once the connection between RA fitting and handle portion (316) has been made, the zero-gravity mode may be deactivated and the actions performed as described elsewhere herein. The RA operating in zero-gravity-on mode may continue to register the pose of the RA fitting, so that when zero gravity mode is deactivated (zero-gravity-off mode), the RA can continue to be controlled by the controller processing unit (440) and the steering guide (300) to the treatment or simulation pose without an intervening calibration manoeuvre. Thus, upon entering the zero-gravity-off mode, the pose of the RA fitting is initially determined from a last registration of the pose of the RA fitting upon exiting the zero-gravity-on mode.

Robotic arms are known in the art, for instance, those manufactured by Universal Robots (Denmark), or by Kuka (Germany).

The positioning device (e.g. a robotic arm) is typically positioned such that the end effector fitting is between the legs of the patient.

To facilitate attachment to the positioning device, handle portion (316) may be provided with a grip locator (300) comprising one or more notches (334) and/or one or more protrusions and/or one or more corners (332) that co-operate with the end effector fitting where the end effector fitting comprises a gripper e.g. a set of jaws, chuck. The grip locator (300) becomes seated firmly within the closed gripper, restricting and preventing rotations and/or movements between the gripper and handle portion (316). Exemplary grip locators are illustrated in FIGS. 11 to 16, 19 to 21. The grip locator (300) may be disposed at the proximal end of the handle portion (316). The base of the notch (334) may be pointed, flat or linear (e.g. a long apex). The notch (334) may have straight (e.g. radial) or bevelled sides. The grip locator (330) allows very accurate and reproducible mountable-dismountable attachment of the end effector fitting to the handle portion (316). The grip locator allows gripping by the gripper of the handle portion (316) with high positional repeatability and reduced play or backlash. The end effector fitting coupled to the grip location (300) attaches the positioning end effector fitting in fixed relation with the grip location (300).

The gripper jaws may be provided with one or more protrusions that engage with the grip locator (e.g. one or more notches) on the handle portion (316) when the gripper is closed. When the notch has bevelled sides, bevelled protrusions on the gripper bring the steering guide (300) into alignment upon closing.

Figures 15A, 15B, 15C:
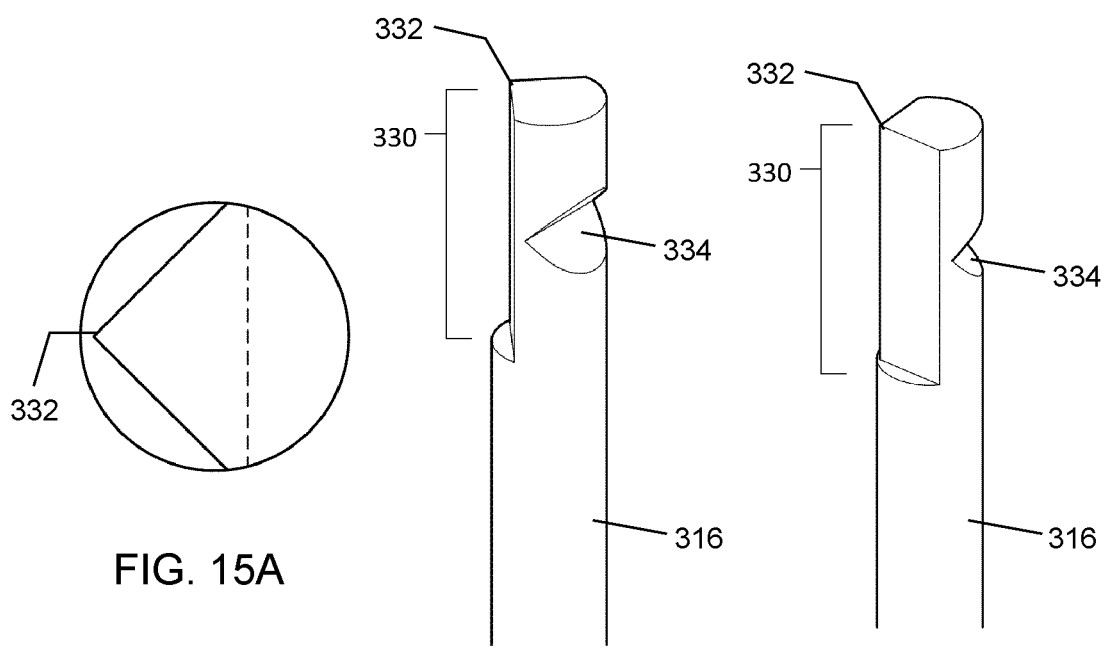

Examples of notches (334) of a grip locator (330) are given in FIGS. 11 to 13, 15A to 15C, 16, 19 to 21. In FIG. 11 straight-sided notches (334) each with a flat base are provided separated longitudinally and at different radial positions, in FIG. 12 a proximal set of straight-sided notches each with a flat base is provided having the same longitudinal position but different radial positions and a distal set of notches is provided having a different longitudinal position from the proximal set bit the same different radial positions, and in FIG. 13 the notches are arranged similarly to FIG. 12 but they have bevelled sides (V-shaped) and a linear base. In FIGS. 15B and C, 16 a bevelled-side (V-shaped) notch (334) is provided having a linear base.

One or more corners (332) of a grip locator (330) may be disposed along an axial direction of the proximal end of the handle portion (316). The corner (332) may be square. There may only be one corner. A grip locator (330) that is a combination of the notch (334) and corner (332) allows for a stable grip by the end effector fitting when it is a gripper having a pair of jaws. At least one notch and the corner may have different mutual directions, preferably perpendicular directions. At least one notch may be provided within the longitudinal span of the corner. For instance, the corner may run in an axial direction at proximal end of the handle portion (316) while the base of a notch may run perpendicular to the axial direction; this ensures an absolutely reproducible fixation of the steering guide to the end effector fitting and removes an additional uncertainty of steering guide position in relation to positioning device base end.

FIGS. 15A, B and C, 16 the proximal end of the handle portion (316) is disposed with grip locator (330) comprising a single corner (332) along an axial direction of the proximal end of the handle portion (316), and a bevelled-side (V-shaped) notch (334) having a linear base is provided within the longitudinal span of the corner. FIG. 15A shows an end view of the handle portion (316) depicting the corner (332).

The gripper jaws may close to form a profile similar in profile to a transverse cross-section of the grip locator (330); the profile in particular may complement the corner (332) of the grip locator (330). When the jaws close, the corner (332) seated in the jaw profile ensures that the steering guide (300) is correctly and stably aligned with the positioning device.

The handle portion (316) may be provided with a docking beacon (340) configured to provide information as to the position and optionally orientation of the steering guide (300) relative to the end effector fitting. The docking beacon (340) allows manual, semi-automatic or automatic guidance of the end effector fitting that comprises a gripper (e.g. a set of jaws, chuck) to the handle portion (316) in particular to the grip locator (330). The position and optionally orientation of the steering guide (300) relative to the end effector fitting can be determined and tracked in real-time.

Exemplary docking beacons (340) are illustrated in FIGS. 19 to 21. The pose of the end effector fitting can be adjusted in real-time as it approaches the handle portion (316) based on the relative pose of the docking beacon (340) to the end effector fitting, thereby allowing coupling without disturbing the pose of steering guide (300) already inserted in the subject canal. A closed feedback loop may be used to guide the end effector fitting towards the target docking beacon (340); where the approaching end effector fitting deviates from the target handle portion (316) a correction to the approach direction is applied until the approach is on target. The closed feedback loop continuously checks and corrects the approach direction. The docking beacon (340) may be provided at the proximal tip of the handle portion (316). The docking beacon may be disposed on the handle portion (316) proximal to the grip locator (330). The docking beacon (340) may be passive or active, or a combination of passive and active. The docking beacon (340) may be detachable from the handle portion (316). The docking beacon (340) may be non-detachable from the handle portion (316).

A passive docking beacon comprises a body of a pre-defined geometric shape that is recognisable by a vision guided robotic system (e.g. one or more cameras, laser scanner). Vision-guided robotic systems are well known in the art. The shape of the body and its orientation allows identification of the pose of the handle portion (316). The body of the passive docking beacon may be positioned at the proximal end of the handle portion (316), preferably at the proximal tip. It may be positioned proximal of the grip locator (330). The optical recognition system may be provided attached to the end effector fitting.

The body of the passive docking beacon may comprise a plurality of spheres (361i to iv) as shown, for instance, in FIG. 19. The number of sphere may be at least 3. The positions and spacing of the spheres are pre-defined. The orientation of the handle portion (316) can be determined from a two-dimensional image of the spheres and their mutual distances. The distance of the end effector fitting from the handle portion can be determined from a two-dimensional image of the spheres and their diameter which will appear the same in any orientation.

The body of the passive docking beacon may comprise a two-dimensional shape (344) (e.g. rectangular form) as shown, for instance, in FIG. 20. The rectangular form is of a pre-defined size and shape. The orientation of the handle portion (316) can be determined from a two-dimensional image of the rectangular form which exhibits a sheered structure depending on the orientation. The distance of the end effector fitting from the handle portion can be determined from a non-contact distance measurement device (e.g. laser or ultrasonic range finder); where the optical recognition system is a laser scanner, it may incorporate a laser range finder.

An active docking beacon wirelessly emits information that allows the position and/or orientation of the handle portion (316) to be determined. It may comprise a solid-state gyroscope (3-axis), wireless transmitter (e.g. Bluetooth), a controller and a replaceable or rechargeable power source. The angle of approach of the end effector fitting may be adapted according to the pose of the handle portion (316) as transmitted by the active docking beacon. Distance between the end effector fitting and the handle portion (316) may be determined by a non-contact distance measurement device (e.g. laser or ultrasonic range finder). An exemplary active docking beacon (342) is shown, for instance, in FIG. 21.

Another example of an active docking beacon is an array of position-determining radio transponder as described elsewhere herein. The positions of the transponders are trackable in real-time a spatial transponder detector that can typically delivers sub-millimetric, sub-degree accuracy. The transponder may receive power inductively or from a built-in power source, for instance, by a battery located on the handle of the steering guide.

The handle portion (316) may be connected or connectable to the end effector fitting by manual guidance. Where the positioning device is a robotic arm (RA), manual docking may be realized in a RA zero gravity mode. The RA may have a switchable zero gravity mode. In zero-gravity-on (weightless) mode, the joints of the robotic arm may or may not be supported (e.g. by the servos) to prevent collapse of the arm. The pose of the RA fitting may be guided manually e.g. by the medical staff. This allows ease of connection between the positioning tool (200) and the RA fitting when the positioning tool (200) has already been inserted into the subject. It also allows a manual fine-tuning of the pose of the steering guide (300) for simulation and treatment. Once the connection between RA fitting and handle portion (316) has been made, the zero-gravity mode may be deactivated and the actions performed as described elsewhere herein. The RA operating in zero-gravity-on mode may continue to register the pose of the RA fitting, so that when zero gravity mode is deactivated (zero-gravity-off mode), the RA can continue to be controlled by the controller processing unit (440) and the steering guide (300) to the treatment or simulation pose without an intervening calibration manoeuvre. Thus, upon entering the zero-gravity-off mode, the pose of the RA fitting is initially determined from a last registration of the pose of the RA fitting upon exiting the zero-gravity-on mode.

Where the positioning device is a robotic arm (RA), docking may realized by setting the pose of the RA fitting on the radiotherapy treatment table to one of the treatment poses, and attaching the RA fitting to the handle portion (316) of the steering guide (300) that is in the patient. The steering guide (300) is introduced inside the patient, placed in the same position as during simulation using laser lights and imaging, then, adjusting the pose of the robotic arm to the same pose as the one reached during simulation (treatment pose). The treatment pose is maintained while the steering guide is connected manually to the effector end (gripper) of the robotic arm. The steering guide would thus have the same pose inside the patient as during simulation.

The effector shaft (310) and the handle portion (316) may be connected by a transmission (314). The transmission (314) is typically a rigid rod. The transmission may be provided in fixed connection and relation (i.e. directional and/or positional) with both the effector shaft (310) and the handle portion (316). It may be a straight, curved, or contain a one or more angular bends. It may be substantially formed of a rigid rod. The rod may be hollow or solid.

The transmission (314) may have a length (T) of 1-30 cm, preferably of 10-25 cm, preferably of 8-20 cm (e.g. FIG. 6) depending on tumour type. The transmission (314) may have a diameter of 0.3-3 cm, preferably of 0.3-1.5 cm. The handle portion and plane formed between transmission and effector shaft may adopt an angle gamma with respect to each other (e.g. FIG. 6A). See Tables 2 and 2a for preferred dimensions, angles for various medical applications.

The diameter may be uniform from proximal to distal end or may vary. For instance, the diameter may be larger towards the proximal part and smaller towards the distal part of the transmission. The change in diameter may be gradual. The small distal diameter is more atraumatic when entering the vagina, and a larger diameter towards the proximal part improves rigidity of the steering guide (300).

The handle portion (316) may be in continuation with the transmission (314). The transmission (314) may have the same diameter (e.g. 0.3-3 cm, preferably 0.5-2 cm) as the handle portion (316) for a part of its proximal length, for instance for 2.5-3 cm of the proximal length of the transmission (314). Having the larger diameter of the handle portion (316) continued into a proximal part of the transmission (314) allows stiffening of the steering guide (300). A strengthening strut (317) may be disposed in a corner between the handle portion (316) and transmission (314) (e.g. FIG. 15, 16, 17).

The distal part (20) of the transmission (314) may have a smaller diameter (0.3-1 cm) in order to be atraumatic by its diameter (atraumatic when entering the vagina).

The guiding strand passage (312) may continue from the effector shaft (310) into the transmission (314). The guiding strand passage (312, a-b) may be a lumen within the transmission (314) or a longitudinal groove on the surface of the transmission (314). The guiding strand passage (312) may continue at least partially along a longitudinal length of the transmission (314). In FIG. 6 possible guiding strand passage (312) exits on the transmission are at the distal end (312,-b3), mid-section (312,-b4), or proximal end (312,-b5). In FIG. 7 a guiding strand passage (312) exits on the transmission at the distal end (312,-b3). In FIG. 8 a guiding strand passage (312) exits on the transmission are at the proximal end (312,-b5). In FIGS. 15, 17 and 18 a possible guiding strand passage (312) exits on the transmission are at the mid-section (312,-b4).

An inflatable transmission balloon (322) may be provided towards a distal (20) end of the transmission (314), for example as shown in FIG. 6, 9, 16, 17, 18, 26. The inflatable transmission balloon (322) may be used to dilate the vagina, preferably to a known or fixed diameter, for radiation treatment. It may further centre the transmission (314) e.g. within the vaginal passage (606). In the inflated condition, it assists in placing the vaginal passage (606) in a defined position and/or orientation and/or diameter for radiotherapy treatment. The diameter of the transmission (314) may be small at a distal end (20), the inflatable transmission balloon (322) allows entry into the vaginal passage (606) with a narrower transmission (314) which is less painful. Inflation of the inflatable transmission balloon (322) dilates the vagina wall so that the wall becomes positioned. A wall of the inflatable transmission balloon (322) may be made from any suitable expandable or non-expandable material. Examples of expandable materials include latex, any elastic polymer, thin film polymers (polyurethane or others) or other elastomers. The inflatable transmission balloon (322) may have a limited inflation size (maximum), whereby inflation at or above the maximum inflation size is resisted (semi-compliant or non compliant balloon). In other words, the inflatable transmission balloon (322) may be expansion limiting, wherein expansion reproducibly stops at the limited inflation size. Continued inflation by application of hydraulic pressure at or above the limited inflation size will not result in further expansion. The limited inflation size is reproducible, for instance, in one or more further treatment sessions. The reproducible limited inflation size, ensures that the target is in the correction position for a given treatment pose, since expansion will stop once the limited size has been reached. The distance between the inflated balloon wall and the effector shaft is known and/or reproducible. In particular for repeated treatments in a fractionated treatment programme, the limited inflation size reduces placement errors in subsequent treatment sessions. Limited maximum inflation size may be achieved by forming the balloon wall from a non-expandable material such as PET, non-compliant or semi-compliant polyamide. The inflatable transmission balloon (322) may have a maximum inflation diameter of 2.0 to 5 cm. Examples of transmission balloon (322) dimensions and medical applications are provided in Tables 2 and 2a.

In fluid connection with the inflatable transmission balloon (322) may be an inflation lumen that extends via an inflation tube such as a catheter or flexible tubing in a proximal (40) direction. This structure may be inside the transmission portion (314) or lie parallel to transmission portion (314). The inflatable transmission balloon (322) may be deflated after simulation and/or after each session or fraction of radiotherapy treatment by release of inflation fluid (e.g. saline) thereby allowing the steering guide (300) to be withdrawn.

In fluid connection with the inflatable transmission balloon (322) may be an inflation lumen (328) that extends in a proximal (40) direction of the steering guide (300) (e.g. FIG. 17, 18). This inflation lumen (328) may be within a body of at least a part of the transmission portion (314). This inflation lumen (328) may be outside and lie parallel to at least a part of the transmission portion (314). A fitting (329) (e.g. Luer fitting) may be disposed at the proximal end of the inflation lumen (328) for connection to a pump. The inflatable transmission balloon (322) may be deflated after simulation and/or after each session or fraction of radiotherapy treatment by release of inflation fluid (e.g. saline or sterile water) thereby allowing the steering guide (300) to be withdrawn.

The transmission balloon (322) may be inflated with saline or sterile water. It may optionally contain 0.5-4% of contrast medium which allows transmission balloon to be visible on CT simulation images and/or on images made before the radiotherapy session or fractions. Alternatively, the transmission balloon (322) may be provided with one or more imaging markers (e.g. imaging visible wires (longitudinal, helicoidal, circular)). One or more radio position-determining transponders may be located on the inflatable transmission balloon (322).

An inflatable transmission balloon (322) may provided towards a distal (20) end of the transmission (314), wherein:
  optionally the inflatable transmission balloon (322) has a fixed maximum inflation diameter, and/or
  optionally, the inflatable transmission balloon (322) bears one or more imaging markers visible by medical imaging, and/or optionally, the inflatable transmission balloon (322) bears one or more radio transponders for determining a position and/or orientation of the transmission (314) and/or of the effector shaft (310) by a spatial transponder detector.

The transmission (314) may be made from any suitable biocompatible material such as medical grade non-ferromagnetic stainless steel, tantalum, titanium, polycarbonate, PEEK, carbon fibre, polyarylamide resin reinforced with fibers (e.g. Ixef (Solvay)), polyphenylsulfone (PPSU) fibreglass, aluminium (coated), bioceramics such as aluminosilicates, styrene acrylonitrile, bioceramic-polymer materials. The transmission (314) may be made from the same material as the handle portion (316). The transmission (314) at the proximal end may have the same diameter as the distal end of the handle portion (316).

The transmission (314) may be formed from an imaging-transparent material such as a polymeric rod or tube. The same material may be used to form the handle portion (316), for ease of manufacture; this can reduce imaging artefacts caused by the transmission (314) in the vaginal regional (606)—this is described in more detail below. Examples of suitable polymers include polycarbonate, polyphenylsulfone (PPSU) and polyarylamide resin reinforced with fibers (e.g. Ixef (Solvay)). Other materials that may be used for the handle portion are fiberglass, carbon fiber, bioceramics such as aluminosilicates, styrene acrylonitrile, bioceramic-polymer materials, biocompatible polymeric hard materials, etc. FIGS. 7, 8, 15, 16, 19-21 depict examples of a steering guide (300) formed from a polymeric handle portion (316) and transmission (314) and both having a larger diameter (e.g. 0.8-2.5 cm) compared with the effector shaft (310) which may be formed from a rigid metal such as titanium.

Where the transmission (314) is not visible or not sufficiently visible to determine the position and/or orientation of the inserter, the transmission (314) may be disposed with one or more imaging markers (350, *a, b, c*). This is of assistance when performing images using the imaging tools of the linear accelerator. The steering guide (300), in particular the transmission (314) may be provided with one or more imaging markers that can be identified by a medical image. An imaging marker may be provided in fixed relation to the transmission (314), for instance on an inner surface, outer surface or within a body of the transmission (314). An imaging marker may be made from a material different from the transmission (314) for instance a heavy metal such as platinum, platinum iridium, tantalum, tungsten, etc. FIG. 16 shows one or more imaging markers (350, *a, b, c*) disposed on the transmission (314).

The polymeric rod or tube for a transmission (314) may have a larger diameter (e.g. 1 cm) compared with a transmission (314) made from a stronger material such as titanium or stainless steel. A polymeric transmission (314) may significantly contribute to reducing artifacts and obtaining superior images of the diseased structures. Some imaging artefact may arise from any imaging markers present on the transmission (314), from the effector shaft (310) which may be made from titanium which corresponds to the intracervical part, and from any imaging markers disposed on the inserter (204) but will be less important than if whole steering guide (300) is made from metal (titanium, non ferro-magnetic steel, coated aluminium, etc.).

When made from a polymeric or ceramic material, the transmission portion (314) material may be mixed with radio-visible material such as barium sulfate, in order to render it radio-visible on simulation images as well as on control images performed before each radiation therapy session. In order to render it radio-visible, the surface of the transmission portion may also be covered with radiovisible longitudinal, circular, helicoidal markers made from metal (e.g. thin titanium or tantalum wires) or from material mixed with barium sulfate for instance. When made from a polymeric material, the transmission portion may also contain radio-visible markers inside the structure.

An angle (alpha) (e.g. FIG. 6) may be formed between the effector shaft (310) and the transmission (314) of 90 deg to 240 deg, depending on the position of the canal e.g. the cervix or uterus and the ease of access. An angle (beta) (e.g. FIG. 6) may be formed between the handle portion (316) and the transmission (314) of 70 deg to 150 deg, depending on ease of access. An angle (gamma) (e.g. FIG. 6A) may be formed between the effector shaft (310) and a plane formed by the transmission (314) and handle portion (316) 0 or −90 to +90, depending on ease of access. See Tables 2 and 2a for preferred dimensions, angles for various medical applications.

TABLE 2

Exemplary dimensions of elongated member and parts of steering guide and transmission balloon. Dimensions may exceed ranges for some presenting subjects and are not intended to be limiting.

| Information | Type of tumor | | | |
| --- | --- | --- | --- | --- |
| | Primitive tumor of cervix uteri | Vaginal Vault recurrence (Uterus absent) | Primitive tumor of Vagina or recurrence located in the vagina (from cervical, uterine, rectal cancer) Uterus Present | Primitive tumor of corpus uteri if inoperable |
| Inserter position | Cervical canal | Vaginal vault | Cervical canal | Cervical/uterus canal |
| Length of elongated member (cm) | 1 to 8 | 1 to 5 | 1 to 8 | 1 to 10 |
| Length of effector shaft (E)(cm) | 1 to 8 | 1 to 5 | 1 to 8 | 1 to 10 |
| Length of transmission part (T)(cm) | 10 to 25 (up to 30 cm if obese) | 10 to 25 (up to 30 cm if obese) | 10 to 25 (up to 30 cm if obese) | 10 to 25 (up to 30 cm if obese) |

TABLE 2-continued

Exemplary dimensions of elongated member and parts of steering guide and transmission balloon. Dimensions may exceed ranges for some presenting subjects and are not intended to be limiting.

| Information | Type of tumor | | | |
|---|---|---|---|---|
| | Primitive tumor of cervix uteri | Vaginal Vault recurrence (Uterus absent) | Primitive tumor of Vagina or recurrence located in the vagina (from cervical, uterine, rectal cancer) Uterus Present | Primitive tumor of corpus uteri if inoperable |
| Length of handle part (H)(cm) | 15 to 25 40-50 in obese | 15 to 25 40-50 in obese | 15 to 25 40-50 in obese | 15 to 25 40-50 in obese |
| Angle E – T parts (°) Alpha | 90 to 240 | 90 to 210 | 90 to 240 | 90 to 240 |
| Angle T – H parts (°) Beta | 70 to 150 | 70 to 150 | 70 to 150 | 70 to 150 |
| Angle H wrt plane (T – E) (*) Gamma | 0 | −90 to +90 | 0 | 0 |

TABLE 2a

Exemplary dimensions of elongated member and parts of steering guide and transmission balloon. Dimensions may exceed ranges for some presenting subjects and are not intended to be limiting.

| Information | Type of tumor | | | |
|---|---|---|---|---|
| | Primitive tumor of cervix uteri | Vaginal Vault recurrence (Uterus absent) | Primitive tumor of Vagina or recurrence located in the vagina (from cervical, uterine, rectal cancer) Uterus Present | Primitive tumor of corpus uteri if inoperable |
| Insertion position | Cervical canal | Vaginal vault resection | Cervical canal | Cervical/uterus canal |
| Effector shaft (mm) max outer diameter when used with inserter | 0.05 to 2 | 0.05 to 2 | 0.05 to 2 | 0.05 to 2 |
| Inserter elongated member (cm) max outer diameter | 0.1 to 0.8 | 0.1 to 0.8 | 0.1 to 0.8 | 0.1 to 0.8 |
| Transmission balloon max diameter inflated (option) (cm) | 1-4, pref. 1.5-3.5 | 1-4, pref. 1.5-3.5 | 1-4, pref. 1.5-3.5 | 1-4, pref. 1.5-3.5 |
| Transmission balloon length inflated (option) (cm) | 3-12, pref. 6 to 8 | 3-12, pref. 6 to 8 | 3-12, pref. 6 to 8 | 3-12, pref. 6 to 8 |

As depicted in FIG. 26, the inserter (204) moves responsive to movements of the effector shaft (310), which in turn moves responsive to movements of the transmission (314) and ultimately of the handle (316). By positioning the inserter (204), the position of the cervix (602), of the tissue around the cervix and of the uterus (604) can be adjusted and maintained in a fixed position. By inflating the inflatable transmission balloon (322) the tissue around the vaginal passage (606) can also be adjusted and maintained in a fixed position The steering guide (300), in particular the effector shaft (310) and/or transmission (314) and/or handle portion (316) and/or transmission balloon where present may be provided with one or more (e.g. 2, 3 or more) position-determining radio transponders (352, a, b, c) whose positions can be determined and tracked using a spatial transponder detector.

The terms position-determining radio transponder and transponder are used interchangeably herein. A transponder is sometimes known as beacon transponder. In FIG. 16 three transponders (352, a, b, c) are provided fixed to an outer surface of or inside the transmission (314) at different positions. The same transponders (352 a-c) also act as imaging markers (350 a-c) because they are visible on a medical image.

A transponder is a device that emits electromagnetic pulses at a certain radio frequency that is detectable by the spatial transponder detector—typically comprising a number of spatially separated receivers (coils). The timing of the pulse as detected by a number of spatially separated receivers in the positional transponder reader allow the location of the transponder to be accurately determined. A transponder is sometimes known as beacon transponder. The transponder may receive power inductively. The transponder may be powered by built-in power source, for instance, by a battery located on the handle of the steering guide. Where more than one transponder is present, each transponder may emit a signal at a different radio frequency.

When at least three separately-identifiable transponders are disposed on the steering guide (300) at different positions, the orientation of the effector shaft (310) may also be determined. Examples of such systems are described, for example, in U.S. Pat. No. 9,248,003 B2, and U.S. Pat. No. 9,072,895.

The use of transponders reduces the need to align the effector shaft (310) and/or transmission (314) prior to radiotherapy treatment using medical imaging several times, which reduces exposure to imaging radiation.

The transponders allow realtime capture of the effector shaft (310) and/or transmission (314) position during simulation. The transponders also allow realtime and automated guidance (e.g. by a robotic arm) of the position and/or orientation of the effector shaft (310) and/or transmission (314) during treatment so that it aligns with a reference pose determined during simulation.

The transponders also allow the position and/or orientation of the effector shaft (310) to be guided, changed and fixed manually in real-time according to the position and orientation information captured by the spatial transponder detector. For instance, a closed feed-back loop, wherein continuous input is the pose of the steering guide (300) and hence of the effector shaft (310) as determined by from the one or more (e.g. 2, 3 or more) position-determining radio transponders, may provide guidance to the operator to manually bring the pose of the steering guide (300) and hence effector shaft (310) into agreement with the pose determined during simulation. In this scenario, the steering guide (300) may be attached by the handle portion (316) to a positioning device that is manually controllable (e.g. a manually adjustable positioning device having lockable passive joints, or a positioning device that is a robotic arm operating in a manual zero-gravity mode). The same transponders and manual control may also allow capture and storage of the pose of the steering guide (300) and hence of the effector shaft (310) during simulation.

According to one aspect:
at least a part of the effector shaft (310) and/or one or more imaging markers borne by the inserter (204) is visible by medical imaging, in particular by X-ray medical imaging and/or MR medical imaging
and/or
at least a distal part the transmission (314) and/or or one or more imaging markers borne by the inserter (204), is visible by medical imaging, in particular by X-ray medical imaging or MR medical imaging
and/or
the transmission (314) and/or the effector shaft (310) is disposed with one or more radio transponders borne by the inserter (204) for determining a position and/or orientation of the transmission (314) and/or of the effector shaft (310) by a spatial transponder detector.

Treatment is typically performed in a two stage protocol. A first stage is called simulation, which involves acquiring internal medical images (e.g. by CT, MRI) of the subject usually in three-dimensions while the subject is accurately aligned on a moveable treatment simulation table in relation to an imaging device. These medical images are used to plan the second stage which is treatment. The radiologist determines from the images which tissues structures are to receive higher doses, lower doses, sensitive structures and the like.

Treatment is usually performed using a linear accelerator that dispenses ionising radiation for radiotherapy. Information obtained during simulation is used to set a number of parameters of the linear accelerator including, the positioning of the patient, the angle of movement of the head, intensity of the beam, energy of the beam and a profile shape of a leaf-collimator where present.

The linear accelerator may incorporate low-resolution medical imaging device to acquire quickly medical images of the subject (e.g. by CT, MRI) to confirm position of tissue determined during simulation.

The medical imaging device (simulation) and linear accelerators are typically disposed in separate rooms.

The position of the patient relative to the medical imaging device is recorded by marking on the subject with a tattoo of one or more positions where projected laser reference lines intersect disposed in known positional relation to the medical imaging device. The treatment room containing the linear accelerator is disposed with equipment that projects a similar pattern of laser reference lines that intersect in known positions in relation to the linear accelerator; by aligning the tattoos with the laser lines the position of the subject relative to the linear accelerator is known. The three dimensional images recorded by a medical imaging device in one room can be transposed to a volume for radiation treatment by the linear accelerator in another room and later in time.

Prior to starting the radiotherapy, the patient is examined optionally under anesthesia and the inserter (204) elongated member (210) is typically inserted into the canal (e.g. cervix) of the subject when tumor is not operable. Once in position, the slide restrictor (220) where present is activated for instance by suturing of the proximal stop member (250) and/or by inflation of the balloon assembly (230), and/or by expanding the stent (240).

Before the simulation, once the patient is lying on the simulation table, the steering guide (300) effector shaft (310) is introduced along the trailing guiding strand (218) and is slidably inserted into the elongated member lumen (214); this step can be performed by the subject themselves. The transmission balloon (322) where present is inflated with water possibly mixed 0.5-4% of contrast medium. The subject is positioned on a body support (e.g. simulation couch or table) whose position and/or orientation are known are adjustable relative to the imaging device. The patient may be asked to lie in a comfortable position on the simulation table. This allows the patient to find for him/herself optimal position on the simulation table during all following treatment fractions. Usually contrast medium is injected intravenously in order to better visualise pelvic vascular structures, the tumor and lymphnodes. Once the position of the subject is validated by the radiation oncologist, the subject is provided with markings on the bare skin (e.g. tattoo, reflective markings) as described above which allow accurate positioning of the body in relation to the body support, using laser beams located in the axis of the patient and on lateral sides during radiotherapy treatment sessions.

Medical images obtained during simulation allow the position of the tissues for treatment to be determined. The direction and/or position of the elongated member (210) and/or of the effector shaft (310) and/or of the transmission part (314), may also monitored by the medical imaging, and can be adjusted by corresponding movements of the handle portion (316). A suitable direction and/or position of the elongated member (210) and/or of the effector shaft (310) and/or the transmission part—which places relevant tissues for treatment in an optimum position—may be determined which is then used as a reference pose. During simulation, which is performed using mainly CT-scan (less often MRI, or in 2 steps, fusing MRI images with simulation CT images) the optimal position of the positioning tool (200) may be determined. For example, where it is found that the cervix uteri may be located too posteriorly, which would induce the irradiation of the whole rectal volume to high doses, using the positioning device (e.g. manual or robotic arm), the uterus is able to be gently brought in a more anterior position during simulation. The same position will be repeatedly reproduced at each treatment session later on. After simulation, the tumour and all organs are drawn on each CT slice for the treatment phase. This will allow prescribing therapeutic doses to each tumor tissue (cervix, uterus, bladder, lymphnodes, etc.) and to prevent too high doses be delivered to healthy tissues (spinal cord, bowel, kidneys, etc.).

Calculations are performed usually by a computer to determine the direction, position, intensity, duration, and frequency of the radiotherapy treatment, and are optimised taking into account the fixed position of the elongated member (210) and/or of the effector shaft (310). After the simulation, the steering guide (300) effector shaft (310), and possibly transmission part are removed along the trailing guiding strand (218); this can be performed by the subject. The trailing guiding strand (218) may be taped to the subject's skin, for instance on one of patients groins. The inserter (204) remains in situ ready for the treatment phase e.g. on the subsequent day or week. The positions of the tissue structures will have expected to have moved prior to the actual treatment, because, for instance, they are not tethered to the pelvis or because the bladder is empty or full, or the colon is empty or full, which have an influence.

Just prior to radiotherapy treatment (e.g. hours, minutes), the subject mounts the body support (e.g. treatment couch or table) to receive therapeutic ionising-radiation, and is positioned relative to the ionising-radiation treatment head, for instance, using the aforementioned markings on the bare skin and axial and lateral laser beams. The steering guide (300) effector shaft (310) is introduced along the trailing guiding strand (218) and is slidably inserted into the elongated member lumen (214); this step can be performed by the subject themselves. Indeed, the patient will immediately feel discomfort when performing sudden movements. Aligning of the patient more correctly on the treatment table is usually performed with the assistance of medical imaging (provided for example by an X-ray imager disposed in relation to the ionising-radiation treatment head), by aligning pelvic bones with the position of pelvic bones that had been determined during simulation. The direction and/or position of the elongated member (210) and/or of the effector shaft (310) is monitored by medical imaging (usually X-ray) and/or by transponders, and may be adjusted by corresponding movements of the handle portion (316), for instance, using a positioning device (e.g. a manual device or a robot arm), to align it with the reference pose. Once the direction and/or position of the elongated member (210) and/or of the effector shaft (310) and/or transmission part has been set, the treatment fraction (one of several) by external radiotherapy can begin. The position of the inserter (204) is maintained fixed during the session or fraction. At the end of the treatment fraction, where present the transmission balloon (322) is deflated by the technician or the nurse, the steering guide (300) effector shaft (310) is removed along the trailing guiding strand (218); this can be performed by the subject. The inserter (100) remains in situ ready for the next radiotherapy treatment e.g. on the subsequent day or week. Such a radiotherapy treatment may have a duration of 1-35 fractions.

As mentioned earlier, the positioning tool (200) may be provided with transponders to allow realtime capture of the positioning tool (200) pose during simulation or treatment. The transponders may be provided on the inserter (204) and/or steering guide (300). On the steering guide, transponders may be provided on the effector shaft (310) and/or on or inside the transmission (314) and/or on or inside the handle portion (316) and/or on the inflatable transmission balloon (322) where present.

The transponders allow real-time guidance of the positioning tool (200) during treatment so that it aligns with a reference pose determined during simulation. The guidance provided may be manual, semi-automatic or automatic by a robotic arm. The transponders allow the position and/or orientation of the effector shaft (310) or inserter (204) to be guided, changed and fixed in real-time according to the position and orientation information captured by the spatial transponder detector.

For instance, a closed feed-back loop, wherein a continuous input is the pose of the effector shaft (310) or inserter (204) as determined by from the one or more (e.g. 2, 3 or more) position-determining radio transponders, may provide guidance to bring the pose of the effector shaft (310) or inserter (204) into agreement with the pose determined during simulation. This can allow a fine-tuning of the positioning tool (200) pose during simulation or treatment in situ.

The transponder real-time guidance may be manual, providing information (e.g. graphical, audible, force-feedback) to guide the operator to manually move and/or fix the positioning tool (200). In this scenario, the steering guide (300) may be attached by the handle portion (316) to a positioning device that is manually controllable (e.g. the robotic arm operating in a manual zero-gravity mode). The same transponders and manual control may also allow capture and storage of the pose of the steering guide (300) and hence of the effector shaft (310) during simulation.

The transponder real-time guidance may be automatic, providing information to the robotic arm, automatically moving the positioning tool (200) by activation of the joints of the robotic arm.

The real-time guidance may be semi-automatic, providing information to the robotic arm and to the operator, to allow partial automatically and partial manual moving of the positioning tool (200).

Transponders function well below the surface of the subject. All transponders do not need to be placed inside patient's body. The transponders located on or inside the positioning tool (200) do not need to be all located inside the body. For instance, 1 or 2 transponders may be located on or inside the positioning tool (200) on a part that will be inside the patient's body (e.g. on the inserter (204), effector shaft (310) or on or inside the distal part of the transmission (314) of the steering guide (300)), and 1 or 2 transponders may be located outside the patient's body (e.g. on or inside the proximal part of the transmission (314) of the steering guide (300)).

With certain prior art techniques, transponders may be implanted inside the body to track the position of an organ. The present positioning tool (200) avoids the need for implantation; transponders are located on or inside a part of the positioning tool (e.g. inserter (204), steering guide (300)) outside the body, and are introduced temporarily inside the body for only a few minutes during each fraction. These transponders track an object inside the body, they are located on the object, they are not implanted, and some of them, 1 or 2 may remain outside the body for tracking the said object. Hence, it avoids the need to implant transponders into the subject.

The wearable inserter facilitates a strictly reproducible positioning of the canal and surrounding tissues which reduces the need to introduce a widening of the radiation beam to account for tissues that would normally change position between treatment fractions. It also immobilises the canal and surrounding tissues during irradiation. In practice, the safety margin can be reduced to the millimetre scale as opposed to the centimetre scale, significantly reducing irradiation of neighbouring organs and tissues. For instance, where the cervix is treated, irritation to the bladder, the rectum, the bowel, the pelvic walls are reduced. Because the beam has a more focused (i.e. reduced) volume, radiation doses can be boosted during external radiation therapy procedure (conformal radiotherapy), avoiding the need for brachytherapy. For instance, with a cervix tumour having a height of 4 cm and a diameter of 5 cm, with a classical 16 mm safety margin, the volume to be treated at a high dose would be 380 cm$^3$. With the positioning tool (200) allowing immobilisation and repositioning that brings the cervix in the same position before each radiation fraction, a tighter margin (e.g. 4 mm) can be implemented, and the high dose volume may be reduced to 126 cm$^3$, a reduction of 3.3 times. This has a tremendously beneficial effect on toxicity reduction.

The wearable inserter obviates the need to sedate the patient prior to radiotherapy treatment. It reduces patient trauma, and repeating the trauma for each treatment fraction. The guiding strand allows the user (radiation oncologist, physician, radiology technician, subject) to easily locate and engage the steering guide from outside the subject. For gynaecological applications, the requirement to use a speculum is avoided. The patient can self-insert the steering guide also. The guiding strand allows repeatable mounting and dismounting of the steering guide prior to and after fractioned treatments. Access to the elongated member lumen (214) is made available despite the wearable inserter being located in situ, for instant, in the cervix.

Also provided herein is a computer implemented method for improving accuracy of site-specific radiotherapy of a bodily tissue of a subject that is a target for radiotherapy treatment, comprising:
  receiving data as to:
    a position and/or orientation of the positioning tool (200), wherein the inserter (204) is located within the canal of the subject,
  outputting instructions to a positioning device (e.g. a robot arm) to adjust using the position and/or orientation of the positioning tool (200) according to a reference pose of positioning tool (200), thereby adjusting the position and/or orientation of the canal and bodily tissue, wherein the reference pose was determined during a treatment simulation procedure.

Also provided herein is a computer implemented method for improving accuracy of site-specific radiotherapy of a bodily tissue of a subject that is a target for radiotherapy treatment, comprising:
  receiving data as to:
    a position and/or orientation of the inserter (204) located within the canal, and/or
    a position and/or orientation of the effector shaft (310) of the steering guide (300) located within the elongated member lumen (214) of the inserter (204),
  outputting instructions to a positioning device (e.g. a robot arm) to adjust using the steering guide (300) the position and/or orientation of the inserter (204) according to a reference pose of the inserter (204) and/or of the effector shaft (310) and/or transmission portion (314), thereby adjusting the position and/or orientation of the canal and bodily tissue, wherein the reference pose was determined during a treatment simulation procedure.

The position and/or orientation of the positioning tool (200) and/or inserter (204) and/or the effector shaft (310) may be determined from a medical image taken just prior to (e.g. minutes, hours) the radiotherapy treatment, or from the position of transponders attached to the positioning tool (200) and/or the inserter (204) and/or to the effector shaft (310) and/or the transmission or handle portion of the steering guide. The reference pose may be determined during the simulation of the treatment relative to patient structures (bones, pelvic bones). The radiotherapy treatment may be a fractionated treatment.

Also provided herein is a computer implemented method for improving accuracy of site-specific radiotherapy of a bodily tissue of a subject that is a target for radiotherapy treatment, comprising:
  (a) receiving by the computer data as to:
    a position and/or orientation of the positioning tool (200), wherein the inserter (204) is located within the canal of the subject, wherein the position and/or orientation of the positioning tool (200) is determined from:
      one or more transponders (260, a, b, c) attached to the inserter (204), and/or
      one or more transponders (352a,b,c) attached to the steering guide (300), and/or
      one or more optically-detectable landmarks (346i-iv, a, b, c) attached to the steering guide (300);
  (b) outputting to a computer graphical user interface a real-time indication of:
    the position and/or orientation of the positioning tool (200), compared with a reference pose of the positioning tool (200) determined during a simulation procedure.

Also provided herein is a computer implemented method for improving accuracy of site-specific radiotherapy of a bodily tissue of a subject that is a target for radiotherapy treatment, comprising:
  (a) receiving by the computer data as to:
    a position and/or orientation of the inserter (204) located within the canal, and/or
    a position and/or orientation of the effector shaft (310) of the steering guide (300) located within the elongated member lumen (214) of the inserter (204);
    wherein the position and/or orientation of the inserter (204) or of the effector shaft (310) is determined from:
      one or more transponders (260, a, b, c) attached to the inserter (204), and/or one or more transponders (352, a, b, c) attached to the steering guide (300), and/or
one or more optically-detectable landmarks (346 i to iv) attached to the steering guide (300);
(b) outputting to a computer graphical user interface a real-time indication of:
the position and/or orientation of the inserter (204), and/or
the position and/or orientation of the effector shaft (310)
compared with a reference pose of the inserter (204) and/or of effector shaft (310) determined during a simulation procedure.

Also provided is a computing device or system configured for performing the computer implemented method described herein.

Also provided is a computer program or computer program product having instructions which when executed by a computing device or system cause the computing device or system to perform the computer implemented method described herein.

Also provided is a computer readable medium having stored thereon the computer program as described herein.

Also provided is a computer readable medium having stored thereon instructions which when executed by a computing device or system cause the computing device or system to perform the computer implemented method described herein.

Also provided is a data stream which is representative of the computer program or computer program product described herein.

Further provided is a system comprising:
the positioning tool (200) as described herein,
a positioning device for adjusting and fixing a position and/or orientation the handle portion (316) and of the effector shaft (310) of the positioning tool (200),
wherein
the handle portion (316) is configured for dismountable attachment to the positioning device, and
the positioning device is a robotic arm.

Provided herein is also a method for treatment of a bodily tissue of a subject that is a target for radiotherapy treatment using site-specific fractionated radiotherapy, comprising:
(a) receiving by a computer data as to:
a position and/or orientation of the positioning tool (200) wherein the inserter (204) is located within the canal, and/or
(b) outputting by the computer instructions to a positioning device (e.g. a robot arm) to adjust using the positioning tool (200) according to a reference pose of the positioning tool (200) thereby adjusting the position and/or orientation of the canal and bodily tissue in order to reproduce the position of the positioning tool (200) as it was during the treatment simulation procedure;
(c) maintaining the position and/or orientation of the positioning tool (200) during a fraction of site-specific fractionated radiotherapy;
(d) removing the steering guide (300); and
(e) repeating steps (a) to (d) in one or more subsequent fractions of site-specific fractionated radiotherapy.

Provided herein is also a method for treatment of a bodily tissue of a subject that is a target for radiotherapy treatment using site-specific fractionated radiotherapy, comprising:
(a) receiving by a computer data as to:
a position and/or orientation of the inserter (204) located within the canal, and/or
a position and/or orientation of the effector shaft (310) of the steering guide (300) located within the elongated member lumen (214) of the inserter (204);
(b) outputting by the computer instructions to a positioning device (e.g. a robot arm) to adjust using the steering guide (300) the position and/or orientation of the inserter (204) according to a reference pose of the inserter (204) and/or effector shaft (310) and/or transmission portion (314), thereby adjusting the position and/or orientation of the canal and bodily tissue in order to reproduce the position of the inserter (204) and/or of the effector shaft (310) and/or transmission portion (314) as it was during the treatment simulation procedure;
(c) maintaining the position and/or orientation of the inserter (204) during a fraction of site-specific fractionated radiotherapy;
(d) removing the steering guide (300); and
(e) repeating steps (a) to (d) in one or more subsequent fractions of site-specific fractionated radiotherapy.

Provided herein is also a method for treatment of a bodily tissue of a subject that is a target for radiotherapy treatment using site-specific fractionated radiotherapy, comprising:
(a) determining:
a position and/or orientation of the positioning tool (200) wherein the inserter (204) located within the canal of the subject wherein the position and/or orientation of the positioning tool (200) is determined from one or more transponders (260, a, b, c) and/or one or more optically-detectable landmarks (346i-iv) attached to the positioning tool (200);
(b) outputting to a computer graphical user interface a real-time indication of the position and/or orientation of the positioning tool (200) compared with a reference pose of the positioning tool (200) determined during a simulation procedure
(c) manually adjusting the position and/or orientation of the positioning tool (200) until it matches the reference pose of the positioning tool (200)
(d) maintaining the position and/or orientation of the positioning tool (200) during a fraction of site-specific fractionated radiotherapy;
(e) removing the steering guide (300) from the positioning tool (200); and
(f) repeating steps (a) to (e) in one or more subsequent fractions of site-specific fractionated radiotherapy.

Provided herein is also a method for treatment of a bodily tissue of a subject that is a target for radiotherapy treatment using site-specific fractionated radiotherapy, comprising:
(a) determining:
a position and/or orientation of the inserter (204) located within the canal, and/or
a position and/or orientation of the effector shaft (310) of the steering guide (300) located within the elongated member lumen (214) of the inserter (204);
wherein the position and/or orientation of the inserter (204) or of the effector shaft (310) is determined from:
one or more transponders (260, a, b, c) attached to the inserter (204), and/or
one or more transponders (352, a, b, c) attached to the steering guide (204), and/or
one or more optically-detectable landmarks (346, i-iv) attached to the steering guide (300)
(b) outputting to a computer graphical user interface a real-time indication of:

the position and/or orientation of the inserter (204), and/or the position and/or orientation of the effector shaft (310)

compared with a reference pose of the inserter (204) and/or of effector shaft (310) determined during a simulation procedure (c) manually adjusting the position and/or orientation of the inserter (204) and/or of the effector shaft (310) until it matches the reference pose of the inserter (204) and/or of effector shaft (310)

(d) maintaining the position and/or orientation of the inserter (204) during a fraction of site-specific fractionated radiotherapy;

(e) removing the steering guide (300); and (f) repeating steps (a) to (e) in one or more subsequent fractions of site-specific fractionated radiotherapy.

The invention claimed is:

1. Positioning tool (200) for assisting treatment of a subject in an external radiotherapy programme comprising one or more external radiotherapy treatment sessions comprising:

an inserter (204) having a proximal (40) and distal (20) end which inserter comprises:

an elongated member (210) configured for insertion through an entrance to a canal (602) in connection with bodily tissue (610) of the subject, and provided with an elongated member lumen (214) configured for receiving an effector shaft (310) of a steering guide (300); and a guiding strand (218) for guiding the effector shaft (310) into the lumen (214) from outside the entrance to the canal, wherein the guiding strand (218) is disposed at least partially within the lumen (214) and is restrained at or towards a distal end (20) of the guiding strand (218) to limit or prevent sliding of the guiding strand (218) in a proximal direction relative to the lumen (214), a removable steering guide (300) having a proximal (40) and distal (20) end comprising:

an effector shaft (310) disposed at the distal end (20) configured for repeatable removable insertion into the elongated member lumen (214) along the guiding strand (218), and a handle portion (316) disposed at the proximal end (40) in fixed relation to the effector shaft (310) for controlling the position and/or direction of the effector shaft (310), wherein the effector shaft (310) comprises a body provided with a guiding strand passage (312) for slidable movement along the guiding strand (218), the guiding strand passage (312) provided at least partially along a length of the body, wherein the positioning tool (200) is configured to move and/or fix the canal (602) and the bodily tissue (610) of the subject for the external radiotherapy treatment session.

2. Positioning tool (200) according to claim 1 wherein the canal is a cervix and/or uterus and/or vaginal vault mass of the subject and the bodily tissue is tissue comprised in the pelvic region, and the entrance to the canal is the entrance to the cervix or a canal inside a vaginal vault mass.

3. Positioning tool (200) according to claim 1, wherein the elongated member (210) is provided with at least one slide restrictor (220) configured to reduce or prevent sliding of the elongated member (210) relative to the canal.

4. Positioning tool (200) according to claim 3, wherein at least one slide restrictor (220) is an inflatable balloon assembly (230) comprising one or more inflatable balloon(s) (231,-a to-h), or an expandable stent (240), a distal protrusion (245) or a stop member (250).

5. Positioning tool (200) according to claim 4, wherein the inflatable balloon assembly (230) comprises one or more inflatable balloon(s) (231,-a to-h) each having an inflatable balloon lumen (232) in fluid connection with an inflation lumen (234) extending via an inflation tube (236) in a proximal (40) direction.

6. Positioning tool (200) according to claim 5 wherein the guiding strand (218) is the inflation tube (236).

7. Positioning tool (200) according to claim 4, provided with at least two slide restrictors (220):

a first slide restrictor comprising the stop member (250) provided at a proximal end (40) of the elongated member (210) and is configured to abut with the canal entrance, optionally wherein the stop member (250) is provided with one or more suture channels (252) for suturing the entrance to the canal, and a second slide restrictor comprising:
-the inflatable balloon assembly (230), or
the distal protrusion (245), or
the expandable stent (240),
provided at a distal end (20) of the elongated member (210).

8. Positioning tool (200) according to claim 1, wherein the guiding strand (218) is non-dismountably or dismountably attached in relation to the lumen (214).

9. Positioning tool (200) according to any one of claim 1, wherein the guiding strand (218) is a flaccid tube (237) configured to receive a stiffening stylet.

10. Positioning tool (200) according to claim 1, wherein:

at least a part of the inserter (204) or one or more imaging markers borne thereby, is visible by medical imaging, in particular by X-ray medical imaging and/or by MR medical imaging, and/or at least a part of the elongated member (210) or one or more imaging markers borne thereby, is visible by medical imaging, in particular by X-ray medical imaging and/or by MR medical imaging, and/or the inserter (204) or elongated member (210) is disposed with one or more radio transponders for determining a position and/or orientation of the inserter (204) and/or elongated member (210) in real-time by a spatial transponder detector, or the elongated member (210) is not visible by X-ray imaging.

11. Positioning tool (200) according to claim 1, wherein the guiding strand passage (312) is a groove or lumen in the body effector shaft (310).

12. Positioning tool (200) according to claim 1, wherein the effector shaft (310) body is rigid, the elongated member (210) is flexible and is stiffened by insertion into the elongated member lumen (214) of the effector shaft (310).

13. Positioning tool (200) according to claim 1, wherein the handle portion (316) is configured for attachment to a positioning device, which positioning device is configured to adjust and fix the position and/or orientation of the effector shaft (310), optionally wherein the handle portion (316) is provided with a grip locator (330) configured to co-operate with an end effector fitting of the positioning device for dismountable, repeatable, and reproducible attachment of the handle portion (316) to the positioning device.

14. Positioning tool (200) according to claim 1, wherein the removable steering guide (300) further comprises:
a transmission (314) joining the handle portion (316) to the effector shaft (310)
optionally, an inflatable transmission balloon (322) provided towards a distal (20) end of the transmission (314), wherein:
optionally the inflatable transmission balloon (322) has a fixed maximum inflation diameter, and/or
optionally, the inflatable transmission balloon (322) bears one or more imaging markers visible by medical imaging, and/or
optionally, the inflatable transmission balloon (322) bears one or more radio transponders for determining a position and/or orientation of the transmission (314) and/or of the effector shaft (310) in real time by a spatial transponder detector.

15. Positioning tool (200) according to claim 1, wherein:
at least a part of the effector shaft (310) and/or one or more imaging markers borne by the effector shaft (310) is visible by medical imaging, in particular by X-ray medical imaging and/or magnetic resonance, MR, medical imaging;
and/or
at least a distal part the transmission (314) and/or or one or more imaging markers borne by the effector shaft (310), is visible by medical imaging, in particular by X-ray medical imaging or MR medical imaging;
and/or
the transmission (314) and/or the effector shaft (310) is disposed with one or more radio transponders for determining a position and/or orientation of the transmission (314) and/or of the effector shaft (310) in real-time by a spatial transponder detector.

16. Positioning tool (200) according to claim 1, wherein the handle portion (316) of the steering guide (300) is disposed with a docking beacon (340) configured to provide real-time information as to the position and optionally orientation of the steering guide (300) to allow manual, semi-automatic or automatic docking guidance of the positioning device with the handle portion (316).

17. Positioning tool (200) according to claim 1, wherein the movement of the canal (602) by the positioning tool (200):
brings bodily tissue (608) connected to the canal (602) into an ionising radiation beam emitted by an ionising-radiation treatment head (518) during the external radiotherapy treatment session,
or
moves bodily tissue (608) connected to the canal (602) away from an ionising radiation beam emitted by an ionising-radiation treatment head (518) during the external radiotherapy treatment session.

18. A system comprising:
the positioning tool (200) according to claim 1;
the positioning device for adjusting and fixing a position and/or orientation the handle portion (316) and of the effector shaft (310) of the positioning tool (200);
wherein
the handle portion (316) is configured for dismountable attachment to the positioning device; and
the positioning device is a robotic arm.

* * * * *